United States Patent
Heo et al.

(10) Patent No.: US 9,954,181 B2
(45) Date of Patent: Apr. 24, 2018

(54) HETERO-CYCLIC COMPOUND AND ORGANIC LIGHT EMITTING DEVICE COMPRISING THE SAME

(71) Applicant: LG CHEM, LTD., Seoul (KR)

(72) Inventors: Dong Uk Heo, Daejeon (KR); Dong Hoon Lee, Daejeon (KR); Sangbin Lee, Daejeon (KR); Jungi Jang, Daejeon (KR); Seong So Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 106 days.

(21) Appl. No.: 15/022,849

(22) PCT Filed: Sep. 22, 2014

(86) PCT No.: PCT/KR2014/008773
§ 371 (c)(1),
(2) Date: Mar. 17, 2016

(87) PCT Pub. No.: WO2015/046835
PCT Pub. Date: Apr. 2, 2015

(65) Prior Publication Data
US 2016/0233430 A1    Aug. 11, 2016

(30) Foreign Application Priority Data

Sep. 24, 2013 (KR) .................. 10-2013-0113112

(51) Int. Cl.
*H01L 51/00* (2006.01)
*C07D 401/10* (2006.01)
(Continued)

(52) U.S. Cl.
CPC ........ *H01L 51/0067* (2013.01); *C07D 401/10* (2013.01); *C07D 401/14* (2013.01); *C07D 403/10* (2013.01); *C07D 409/14* (2013.01); *C09K 11/025* (2013.01); *H01L 51/0052* (2013.01); *H01L 51/0058* (2013.01); *H01L 51/0068* (2013.01); *H01L 51/006* (2013.01); *H01L 51/0072* (2013.01);
(Continued)

(58) Field of Classification Search
CPC .. C07D 401/10; C07D 401/14; C07D 403/10; C07D 409/14
See application file for complete search history.

(56) References Cited

U.S. PATENT DOCUMENTS 6,057,048 A * 5/2000 Hu ................... C07D 251/24
313/504
2014/0014935 A1    1/2014 Fukushima et al.
(Continued)

FOREIGN PATENT DOCUMENTS

CN    101412907 A * 4/2009 ......... H01L 51/0052
EP    2749625 A1    7/2014
(Continued)

OTHER PUBLICATIONS

Machine-generated English-language translation of CN-101412907 A.*

*Primary Examiner* — Vu A Nguyen
(74) *Attorney, Agent, or Firm* — Dentons US LLP

(57) ABSTRACT

The present specification provides a hetero-cyclic compound and an organic light emitting device including the hetero-cyclic compound.

14 Claims, 1 Drawing Sheet

(51) Int. Cl.
  *C07D 403/10* (2006.01)
  *C07D 401/14* (2006.01)
  *C07D 409/14* (2006.01)
  *C09K 11/02* (2006.01)
  *H01L 51/50* (2006.01)

(52) U.S. Cl.
  CPC ...... *H01L 51/0077* (2013.01); *H01L 51/5012* (2013.01); *H01L 51/5056* (2013.01); *H01L 51/5072* (2013.01); *H01L 51/5076* (2013.01); *H01L 51/5088* (2013.01); *H01L 51/5092* (2013.01); *H01L 51/5096* (2013.01)

(56) References Cited

U.S. PATENT DOCUMENTS

| | | |
|---|---|---|
| 2014/0203272 A1 | 7/2014 | Hong et al. |
| 2016/0172598 A1 | 6/2016 | Lee et al. |

FOREIGN PATENT DOCUMENTS

| | | | |
|---|---|---|---|
| JP | 2006-225322 A | | 8/2006 |
| KR | 10-2013-0098225 A | | 9/2013 |
| KR | 10-2013-0098266 A | | 9/2013 |
| KR | 20130098226 A | * | 9/2013 |
| KR | 1020130098226 A | | 9/2013 |
| TW | 201512369 A | | 4/2015 |
| WO | 2012-133256 A1 | | 10/2012 |
| WO | 2013/129835 A1 | | 9/2013 |

\* cited by examiner

[Figure 1]
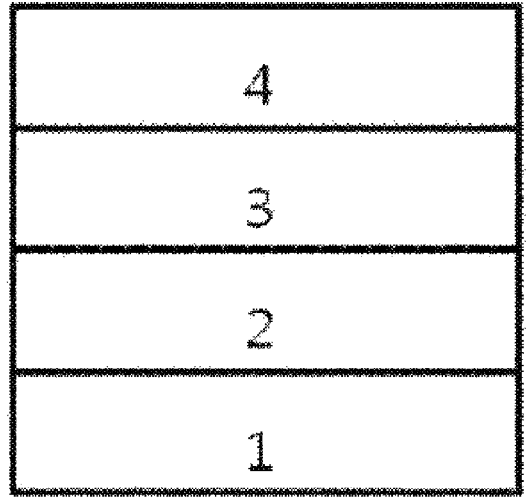
[Figure 2]
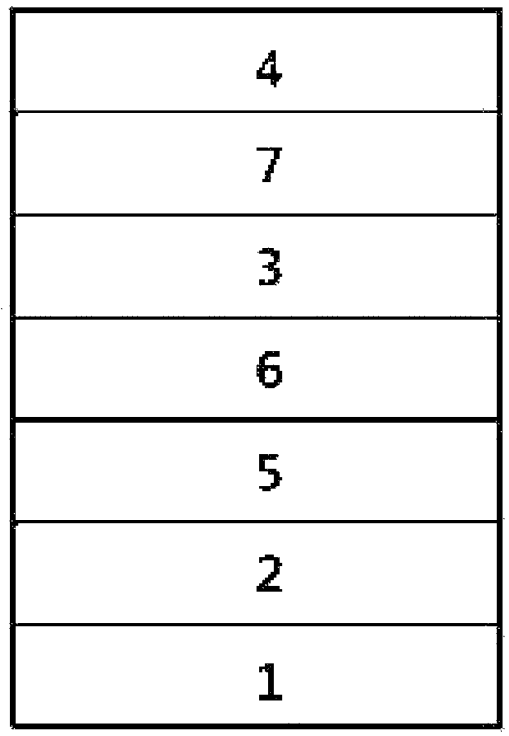

HETERO-CYCLIC COMPOUND AND ORGANIC LIGHT EMITTING DEVICE COMPRISING THE SAME

TECHNICAL FIELD

This application is a National Stage Entry of International Application No. PCT/KR2014/008773, filed Sep. 22, 2014, and claims the benefit of and priority to Korean Application No. 10-2013-0113112, filed on Sep. 24, 2013, all of which are hereby incorporated by reference in their entirety for all purposes as if fully set forth herein.

The present specification relates to a novel hetero-cyclic compound and an organic light emitting device including the same.

BACKGROUND ART

In general, an organic light emitting phenomenon means a phenomenon where electric energy is converted into light energy by using an organic material. An organic light emitting device using the organic light emitting phenomenon has a structure generally including an anode, a cathode, and an organic material layer interposed therebetween. Herein, in many cases, the organic material layer has a multilayered structure constituted by different materials in order to increase efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, holes are injected from the anode to the organic material layer and electrons are injected from the cathode to the organic material layer, and when the injected holes and electrons meet each other, an exciton is formed, and light is emitted when the exciton falls to a bottom state again.

There is a continuous demand for developing a novel material for the aforementioned organic light emitting device.

PRIOR ART DOCUMENT

Patent Document (Patent Document 1) Korean Patent Application Laid-Open No. 2005-0084912

DETAILED DESCRIPTION OF THE INVENTION

Technical Problem

Therefore, the present inventors aim to provide a hetero-cyclic compound having a chemical structure that can perform various roles required in an organic light emitting device according to a substituent group due to the aforementioned reason, and an organic light emitting device including the same.

Technical Solution

An exemplary embodiment of the present specification provides a compound represented by the following Chemical Formula 1.

[Chemical Formula 1]

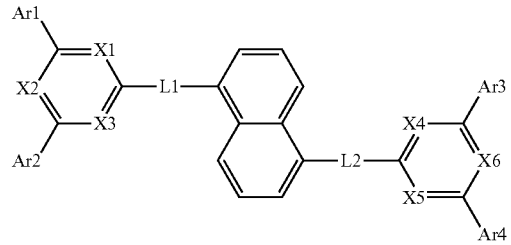

In Chemical Formula 1,

X1 to X6 are the same as or different from each other, and are each independently a trivalent hetero atom or CH, at least one of X1 to X3 is CH or at least one of X4 to X6 is CH, at least one of X1 to X3 is N or at least one of X4 to X6 is N, L1 and L2 are the same as each other, and are a direct bond; or a substituted or unsubstituted arylene group having 6 to 9 carbon atoms, Ar1 to Ar4 are the same as or different from each other, and are each independently a substituted or unsubstituted aryl group; or a substituted or unsubstituted hetero-cyclic group,

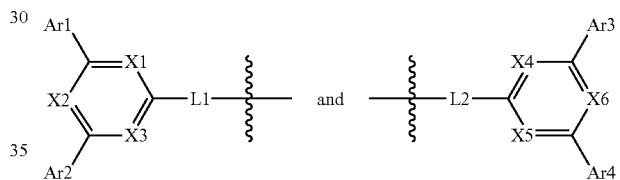

Ar2 and Ar4 are the same as each other, and in the case where both L1 and L2 are a direct bond, both of Ar1 or Ar2 and Ar3 or Ar4 are not a benzimidazole group.

Another exemplary embodiment of the present specification provides an organic light emitting device including: a first electrode; a second electrode provided to face the first electrode; and one or more organic material layers including a light emitting layer provided between the first electrode and the second electrode, in which one or more layers of the organic material layers include the hetero-cyclic compound represented by Chemical Formula 1.

Advantageous Effects

A novel compound according to the present specification can be used as a material of an organic material layer of an organic light emitting device, and efficiency can be improved and low driving voltage and/or life-span properties can be improved in the organic light emitting device by using the compound.

BRIEF DESCRIPTION OF DRAWINGS

FIG. 1 illustrates an example of an organic light emitting device including a substrate 1, an anode 2, a light emitting layer 3, and a cathode 4.

FIG. 2 illustrates an example of an organic light emitting device including a substrate 1, an anode 2, a hole injection layer 5, a hole transport layer 6, a light emitting layer 3, an electron transport layer 7, and a cathode 4.

EXPLANATION OF REFERENCE NUMERALS
AND SYMBOLS

1: Substrate
2: Anode
3: Light emitting layer
4: Cathode
5: Hole injection layer
6: Hole transport layer
7: Electron transport layer

BEST MODE

The present specification provides a compound represented by Chemical Formula 1.

In an exemplary embodiment of the present specification, L1 and L2 are the same as or different from each other, and are each independently a direct bond; or a substituted or unsubstituted arylene group having 6 to 9 carbon atoms. In this case, 1,5-naphthalene serves as an electron donor, and a monocycle including X1 to X3 and X4 to X6, that is, a hetero-cycle including one or two Ns serves as an electron acceptor.

In the case where L1 and L2 connecting the electron acceptor and the electron donor are an arylene group having 6 to 9 carbon atoms, since a predetermined appropriate distance may be maintained, an orbital distribution of a HOMO (highest occupied molecular orbital) and a LUMO (lowest unoccupied molecular orbital) is smooth.

Examples of the substituent groups will be described below, but are not limited thereto.

In the present specification, the term "substituted or unsubstituted" means that substitution is performed by one or two or more substituent groups selected from the group consisting of deuterium; a halogen group; a nitrile group; a nitro group; an imide group; an amide group; a hydroxy group; a thiol group; an alkyl group; an alkenyl group; an alkoxy group; a cycloalkyl group; a silyl group; an arylalkenyl group; an aryloxy group; an alkylthioxy group; an arylthioxy group; an alkylsulfoxy group; an arylsulfoxy group; a silyl group; a boron group; an alkylamine group; an aralkylamine group; an arylamine group; an aryl group; an arylalkyl group; an arylalkenyl group; and a hetero-cyclic group, substitution is performed by a substituent group where two or more substituent groups of the exemplified substituent groups are connected, or there is no substituent group. For example, the "substituent group where two or more substituent groups are connected" may be a biphenyl group. That is, the biphenyl group may be an aryl group, or may be interpreted as a substituent group where two phenyl groups are connected. The term "substituted or unsubstituted" means that substitution is performed by the substituent group where two or more substituent groups of the exemplified substituent groups are connected or there is no substitution. For example, the "substituent group where two or more substituent groups are connected" may be a biphenyl group. That is, the biphenyl group may be an aryl group, or may be interpreted as a substituent group where two phenyl groups are connected.

The term "substituted" means that a hydrogen atom bonded to a carbon atom of a compound is changed into another substituent group, a substitution position is not limited as long as the substitution position is a position at which the hydrogen atom is substituted, that is, a position at which the substituent group can be substituted, and in the case where two or more atoms are substituted, two or more substituent groups may be the same as or different from each other.

In the present specification, examples of a halogen group include fluorine, chlorine, bromine, or iodine. In the present specification, the number of carbon atoms of an imide group is not particularly limited but is preferably 1 to 25. Specifically, the imide group may be compounds having the following structures, but is not limited thereto.

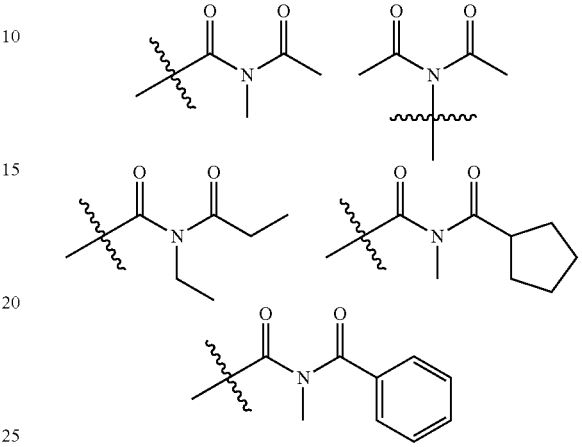

In the present specification, one or two nitrogen atoms of an amide group may be substituted by hydrogen, a straight-chained, branched-chained, or cyclic-chained alkyl group having 1 to 25 carbon atoms, or an aryl group having 6 to 25 carbon atoms. Specifically, the amide group may be compounds having the following Structural Formulas, but is not limited thereto.

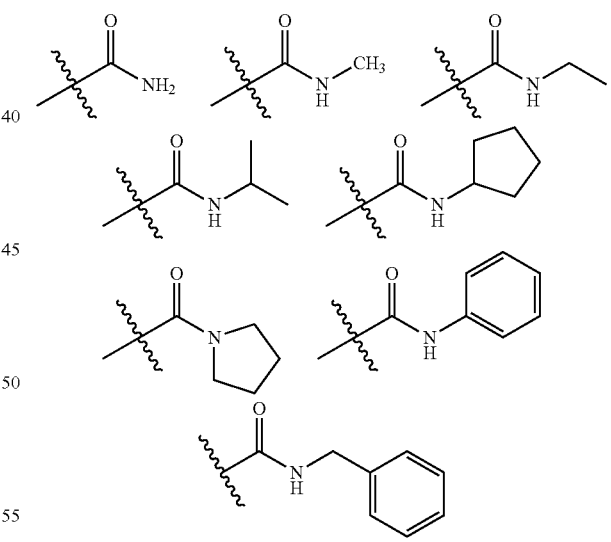

In the present specification, an alkyl group may be a straight or branched chain, and the number of carbon atoms thereof is not particularly limited but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be a straight, branched, or cyclic chain. The number of carbon atoms of the alkoxy group is not particularly limited, but preferably 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be a straight or branched chain, and the number of carbon atoms thereof is not particularly limited but is preferably 2 to 40. Specific examples thereof include vinyl, 1-prophenyl, isoprophenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the aryl group may be a monocyclic aryl group or a polycyclic aryl group. Further, in the present specification, the aryl group may mean an aromatic cycle.

In the case where the aryl group is the monocyclic aryl group, the number of carbon atoms thereof is not particularly limited but is preferably 6 to 25. Specific examples of the monocyclic aryl group may include a phenyl group, a biphenyl group, a terphenyl group, and the like, but are not limited thereto.

In the case where the aryl group is the polycyclic aryl group, the number of carbon atoms thereof is not particularly limited but is preferably 10 to 24. Specific examples of the polycyclic aryl group may include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and the adjacent substituent groups may be bonded to each other to form a cycle.

In the case where the fluorenyl group is substituted,

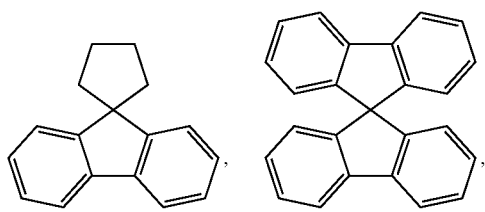

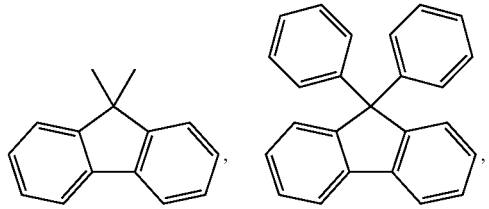

and the like may be formed. However, the example thereof is not limited thereto.

In the present specification, specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the number of carbon atoms of the amine group is not particularly limited, but preferably 1 to 50. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group, and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group of the arylamine group may be a monocyclic aryl group or a polycyclic aryl group. The arylamine group including two or more aryl groups may include the monocyclic aryl group, the polycyclic aryl group, or both the monocyclic aryl group and the polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, the hetero-cyclic group includes an atom other than carbon, or one or more heteroatoms, and specifically, the heteroatom may include one or more atoms selected from the group consisting of O, N, Se, S, and the like. It is preferable that the number of carbon atoms of the hetero-cyclic group be 2 to 60. Examples of the hetero-cyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the heteroaryl group of the heteroarylamine group may be selected from the aforementioned examples of the hetero-cyclic group.

In the present specification, the aryl group of the aryloxy group, the arylthioxy group, the arylsulfoxy group, and the aralkylamine group is the same as the aforementioned examples of the aryl group. Specific examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, specific examples of the arylthioxy group include a phenylthioxy group, a 2-methylphenylthioxy group, a 4-tert-butylphenylthioxy group, and the like, and specific examples of the arylsulfoxy group include a benzenesulfoxy group, a p-toluenesulfoxy group, and the like, but are not limited thereto.

In the present specification, the alkyl group of an alkylthioxy group and an alkylsulfoxy group is the same as the aforementioned examples of the alkyl group. Specific examples of the alkylthioxy group include a methylthioxy group, an ethylthioxy group, a tert-butylthioxy group, a hexylthioxy group, an octylthioxy group, and the like, and specific examples of the alkylsulfoxy group include mesyl, an ethylsulfoxy group, a propylsulfoxy group, a butylsulfoxy group, and the like, but the examples are not limited thereto.

In the present specification, the arylene group means a matter where two bonding positions exist at the aryl group, that is, a divalent group. Except that the groups are each the divalent group, the aforementioned description of the aryl group may be applied thereto.

In the present specification,

means a portion connected to another substituent group.

In the exemplary embodiment of the present specification, L1 and L2 are the same as or different from each other, and are each independently a direct bond; or a substituted or unsubstituted phenylene group.

In the exemplary embodiment of the present specification, L1 is a direct bond.

In the exemplary embodiment of the present specification, L2 is a direct bond.

In the exemplary embodiment of the present specification, L1 is a substituted or unsubstituted arylene group having 6 to 9 carbon atoms.

In the exemplary embodiment of the present specification, L1 is a substituted or unsubstituted phenylene group.

In the exemplary embodiment of the present specification, L1 is a phenylene group.

In another exemplary embodiment, L1 is a phenylene group, and the phenylene group is

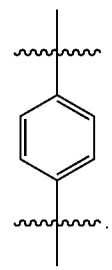

In the exemplary embodiment of the present specification, L2 is a substituted or unsubstituted arylene group.

In the exemplary embodiment of the present specification, L2 is a substituted or unsubstituted phenylene group.

In the exemplary embodiment of the present specification, L2 is a phenylene group.

In another exemplary embodiment, L2 is a phenylene group, and the phenylene group is

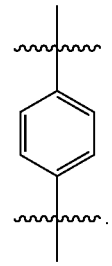

In the present specification, examples of the trivalent hetero atom include N, P, or the like, but are not limited thereto.

In the exemplary embodiment of the present specification, the trivalent hetero atom is N.

In the exemplary embodiment of the present specification, X1 to X3 are the same as or different from each other and are each independently N or CH, at least one of X1 to X3 is N, and at least one of X1 to X3 is CH.

In the exemplary embodiment of the present specification, X1 may be N and X2 and X3 may be CH.

In the exemplary embodiment of the present specification, X2 may be N and X1 and X3 may be CH.

In the exemplary embodiment of the present specification, X3 may be N and X1 and X2 may be CH.

In the exemplary embodiment of the present specification, X1 and X2 may be N. In this case, X3 is CH.

In the exemplary embodiment of the present specification, X1 and X3 may be N. In this case, X2 is CH.

In the exemplary embodiment of the present specification, X2 and X3 may be N. In this case, X1 is CH.

In the exemplary embodiment of the present specification, X4 to X6 are the same as or different from each other and are each independently N or CH, at least one of X4 to X6 is N, and at least one of X4 to X6 is CH.

In the exemplary embodiment of the present specification, X4 may be N and X5 and X6 may be CH.

In the exemplary embodiment of the present specification, X5 may be N and X4 and X6 may be CH.

In the exemplary embodiment of the present specification, X6 may be N and X4 and X5 may be CH.

In the exemplary embodiment of the present specification, X4 and X5 may be N. In this case, X6 is CH.

In the exemplary embodiment of the present specification, X4 and X6 may be N. In this case, X5 is CH.

In the exemplary embodiment of the present specification, X5 and X6 may be N. In this case, X4 is CH.

In the exemplary embodiment of the present specification, Ar1 to Ar4 are the same as or different from each other, and are each independently a substituted or unsubstituted phenyl group; a substituted or unsubstituted biphenyl group; a substituted or unsubstituted terphenyl group; a substituted or unsubstituted fluorenyl group; a substituted or unsubstituted phenanthryl group; or a substituted or unsubstituted naphthyl group.

In the exemplary embodiment of the present specification, Ar1 to Ar4 are the same as or different from each other, and are each independently a substituted or unsubstituted pyridine group; or a substituted or unsubstituted thiophene group.

In the exemplary embodiment of the present specification, Ar1 is a substituted or unsubstituted aryl group.

In the exemplary embodiment of the present specification, Ar1 is a substituted or unsubstituted phenyl group.

In the exemplary embodiment of the present specification, Ar1 is a phenyl group.

In the exemplary embodiment of the present specification, Ar1 is a phenyl group substituted by a nitrile group.

In the exemplary embodiment of the present specification, Ar1 is

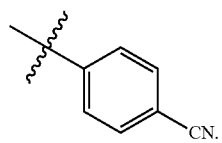 [SMILES: *c1ccc(C#N)cc1]

In the exemplary embodiment of the present specification, Ar1 is

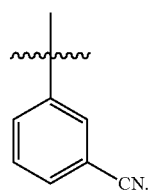

In the exemplary embodiment of the present specification, Ar1 is

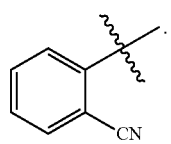 [SMILES: *c1ccccc1C#N]

In the exemplary embodiment of the present specification, Ar1 is a substituted or unsubstituted biphenyl group.

In the exemplary embodiment of the present specification, Ar1 is a biphenyl group.

In the exemplary embodiment of the present specification, Ar1 is a biphenyl group and

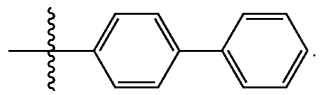 [SMILES: *c1ccc(-c2ccccc2)cc1]

In the exemplary embodiment of the present specification, Ar1 is a substituted or unsubstituted terphenyl group.

In the exemplary embodiment of the present specification, Ar1 is a terphenyl group and

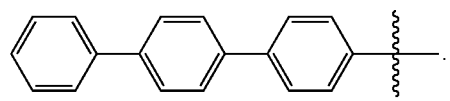 [SMILES: *c1ccc(-c2ccc(-c3ccccc3)cc2)cc1]

In the exemplary embodiment of the present specification, Ar1 is a terphenyl group and

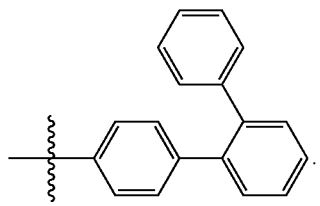 [SMILES: *c1ccc(-c2ccccc2-c2ccccc2)cc1]

In the exemplary embodiment of the present specification, Ar1 is a substituted or unsubstituted fluorenyl group.

In the exemplary embodiment of the present specification, Ar1 is a fluorenyl group substituted by an alkyl group.

In the exemplary embodiment of the present specification, Ar1 is a fluorenyl group substituted by a methyl group.

In the exemplary embodiment of the present specification, Ar1 is a fluorenyl group substituted by an aryl group.

In the exemplary embodiment of the present specification, Ar1 is a fluorenyl group substituted by a phenyl group.

In the exemplary embodiment of the present specification, a second carbon position of the fluorenyl group and a hetero-cycle including one or two or more Ns may be connected.

In the exemplary embodiment of the present specification, Ar1 is a substituted or unsubstituted naphthyl group.

In the exemplary embodiment of the present specification, Ar1 is a naphthyl group.

In the exemplary embodiment of the present specification, Ar1 is a naphthyl group and

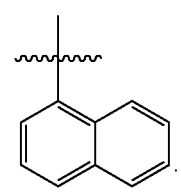 [SMILES: *c1cccc2ccccc12]

In the exemplary embodiment of the present specification, Ar1 is a naphthyl group and

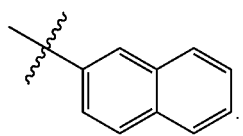 [SMILES: *c1ccc2ccccc2c1]

In the exemplary embodiment of the present specification, Ar1 is a substituted or unsubstituted phenanthryl group.

In the exemplary embodiment of the present specification, Ar1 is a phenanthryl group.

In the exemplary embodiment of the present specification, Ar1 is a phenanthryl group and

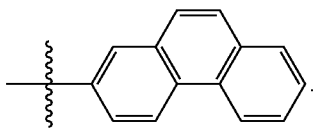

In the exemplary embodiment of the present specification, Ar1 is a substituted or unsubstituted hetero-cyclic group including one or more of O, N, and S as a substituted or unsubstituted hetero element.

In the exemplary embodiment of the present specification, Ar1 is a substituted or unsubstituted pyridine group.

In the exemplary embodiment of the present specification, Ar1 is a pyridine group.

In the exemplary embodiment of the present specification, Ar1 is a pyridine group and

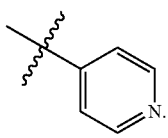 [SMILES: *c1ccncc1]

In the exemplary embodiment of the present specification, Ar1 is a substituted or unsubstituted thiophene group.

In the exemplary embodiment of the present specification, Ar1 is a thiophene group.

In the exemplary embodiment of the present specification, Ar2 is a substituted or unsubstituted aryl group.

In the exemplary embodiment of the present specification, Ar2 is a substituted or unsubstituted phenyl group.

In the exemplary embodiment of the present specification, Ar2 is a phenyl group.

In the exemplary embodiment of the present specification, Ar2 is a phenyl group substituted by a nitrile group.

In the exemplary embodiment of the present specification, Ar2 is

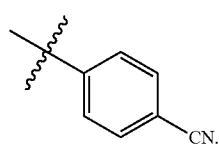 [SMILES: *c1ccc(C#N)cc1]

In the exemplary embodiment of the present specification, Ar2 is

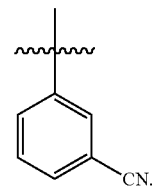

In the exemplary embodiment of the present specification, Ar2 is

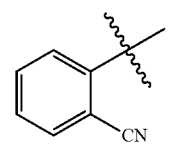

In the exemplary embodiment of the present specification, Ar2 is a substituted or unsubstituted biphenyl group.

In the exemplary embodiment of the present specification, Ar2 is a biphenyl group.

In the exemplary embodiment of the present specification, Ar2 is a biphenyl group and

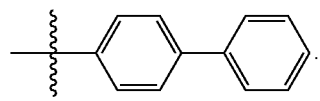 [SMILES: *c1ccc(-c2ccccc2)cc1]

In the exemplary embodiment of the present specification, Ar2 is a substituted or unsubstituted terphenyl group.

In the exemplary embodiment of the present specification, Ar2 is a terphenyl group and

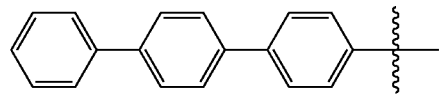

In the exemplary embodiment of the present specification, Ar2 is a terphenyl group and

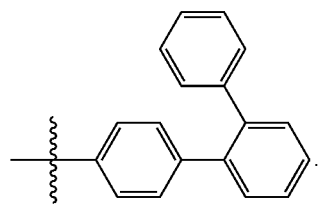 [SMILES: *c1ccc(-c2ccccc2-c2ccccc2)cc1]

In the exemplary embodiment of the present specification, Ar2 is a substituted or unsubstituted fluorenyl group.

In the exemplary embodiment of the present specification, Ar2 is a fluorenyl group substituted by an alkyl group.

In the exemplary embodiment of the present specification, Ar2 is a fluorenyl group substituted by a methyl group.

In the exemplary embodiment of the present specification, Ar2 is a fluorenyl group substituted by an aryl group.

In the exemplary embodiment of the present specification, Ar2 is a fluorenyl group substituted by a phenyl group.

In the exemplary embodiment of the present specification, a second carbon position of the fluorenyl group and a hetero-cycle including one or two or more Ns may be connected.

In the exemplary embodiment of the present specification, Ar2 is a substituted or unsubstituted naphthyl group.

In the exemplary embodiment of the present specification, Ar2 is a naphthyl group.

In the exemplary embodiment of the present specification, Ar2 is a naphthyl group and

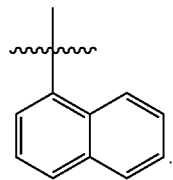 [SMILES: *c1cccc2ccccc12]

In the exemplary embodiment of the present specification, Ar2 is a naphthyl group and

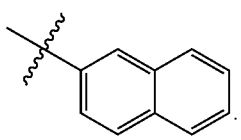

In the exemplary embodiment of the present specification, Ar2 is a substituted or unsubstituted phenanthryl group.

In the exemplary embodiment of the present specification, Ar2 is a phenanthryl group.

In the exemplary embodiment of the present specification, Ar2 is a phenanthryl group and

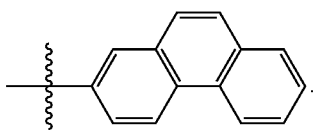

In the exemplary embodiment of the present specification, Ar2 is a substituted or unsubstituted hetero-cyclic group including one or more of O, N, and S as a substituted or unsubstituted hetero element.

In the exemplary embodiment of the present specification, Ar2 is a substituted or unsubstituted pyridine group.

In the exemplary embodiment of the present specification, Ar2 is a pyridine group.

In the exemplary embodiment of the present specification, Ar2 is a pyridine group and

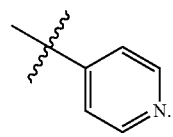

In the exemplary embodiment of the present specification, Ar2 is a substituted or unsubstituted thiophene group.

In the exemplary embodiment of the present specification, Ar2 is a thiophene group.

In the exemplary embodiment of the present specification, Ar3 is a substituted or unsubstituted aryl group.

In the exemplary embodiment of the present specification, Ar3 is a substituted or unsubstituted phenyl group.

In the exemplary embodiment of the present specification, Ar3 is a phenyl group.

In the exemplary embodiment of the present specification, Ar3 is a phenyl group substituted by a nitrile group.

In the exemplary embodiment of the present specification, Ar3 is

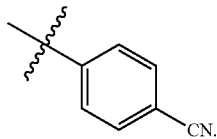 [SMILES: *c1ccc(C#N)cc1]

In the exemplary embodiment of the present specification, Ar3 is

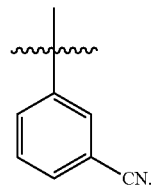 [SMILES: *c1cccc(C#N)c1]

In the exemplary embodiment of the present specification, Ar3 is

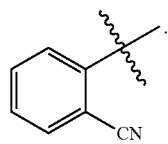 [SMILES: *c1ccccc1C#N]

In the exemplary embodiment of the present specification, Ar3 is a substituted or unsubstituted biphenyl group.

In the exemplary embodiment of the present specification, Ar3 is a biphenyl group.

In the exemplary embodiment of the present specification, Ar3 is a biphenyl group and

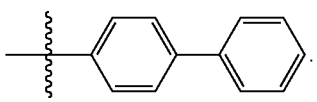

In the exemplary embodiment of the present specification, Ar3 is a substituted or unsubstituted terphenyl group.

In the exemplary embodiment of the present specification, Ar3 is a terphenyl group and

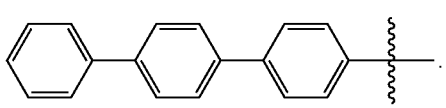 [SMILES: *c1ccc(-c2ccc(-c3ccccc3)cc2)cc1]

In the exemplary embodiment of the present specification, Ar3 is a terphenyl group and

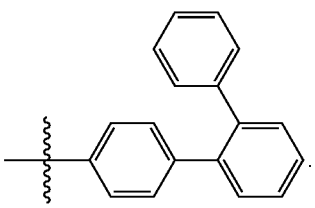 [SMILES: *c1ccc(-c2ccccc2-c2ccccc2)cc1]

In the exemplary embodiment of the present specification, Ar3 is a substituted or unsubstituted fluorenyl group.

In the exemplary embodiment of the present specification, Ar3 is a fluorenyl group substituted by an alkyl group.

In the exemplary embodiment of the present specification, Ar3 is a fluorenyl group substituted by a methyl group.

In the exemplary embodiment of the present specification, Ar3 is a fluorenyl group substituted by an aryl group.

In the exemplary embodiment of the present specification, Ar3 is a fluorenyl group substituted by a phenyl group.

In the exemplary embodiment of the present specification, a second carbon position of the fluorenyl group and a hetero-cycle including one or two or more Ns may be connected.

In the exemplary embodiment of the present specification, Ar3 is a substituted or unsubstituted naphthyl group.

In the exemplary embodiment of the present specification, Ar3 is a naphthyl group.

In the exemplary embodiment of the present specification, Ar3 is a naphthyl group and

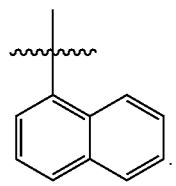

In the exemplary embodiment of the present specification, Ar3 is a naphthyl group and

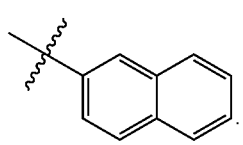 [SMILES: *c1ccc2ccccc2c1]

In the exemplary embodiment of the present specification, Ar3 is a substituted or unsubstituted phenanthryl group.

In the exemplary embodiment of the present specification, Ar3 is a phenanthryl group.

In the exemplary embodiment of the present specification, Ar3 is a phenanthryl group and

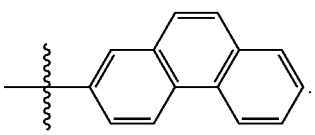 [SMILES: *c1ccc2c(ccc3ccccc32)c1]

In the exemplary embodiment of the present specification, Ar3 is a substituted or unsubstituted hetero-cyclic group including one or more of O, N, and S as a substituted or unsubstituted hetero element.

In the exemplary embodiment of the present specification, Ar3 is a substituted or unsubstituted pyridine group.

In the exemplary embodiment of the present specification, Ar3 is a pyridine group.

In the exemplary embodiment of the present specification, Ar3 is a pyridine group and

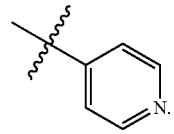 [SMILES: *c1ccncc1]

In the exemplary embodiment of the present specification, Ar3 is a substituted or unsubstituted thiophene group.

In the exemplary embodiment of the present specification, Ar3 is a thiophene group.

In the exemplary embodiment of the present specification, Ar4 is a substituted or unsubstituted aryl group.

In the exemplary embodiment of the present specification, Ar4 is a substituted or unsubstituted phenyl group.

In the exemplary embodiment of the present specification, Ar4 is a phenyl group.

In the exemplary embodiment of the present specification, Ar4 is a phenyl group substituted by a nitrile group.

In the exemplary embodiment of the present specification, Ar4 is

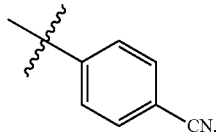 [SMILES: *c1ccc(C#N)cc1]

In the exemplary embodiment of the present specification, Ar4 is

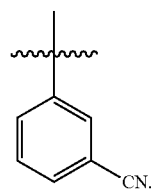

In the exemplary embodiment of the present specification, Ar4 is

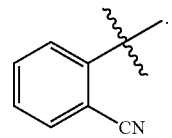 [SMILES: *c1ccccc1C#N]

In the exemplary embodiment of the present specification, Ar4 is a substituted or unsubstituted biphenyl group.

In the exemplary embodiment of the present specification, Ar4 is a biphenyl group.

In the exemplary embodiment of the present specification, Ar4 is a biphenyl group and

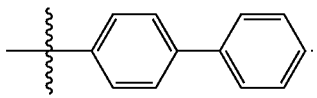

In the exemplary embodiment of the present specification, Ar4 is a substituted or unsubstituted terphenyl group.

In the exemplary embodiment of the present specification, Ar4 is a terphenyl group and

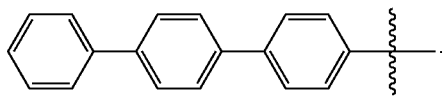 [SMILES: *c1ccc(-c2ccc(-c3ccccc3)cc2)cc1]

In the exemplary embodiment of the present specification, Ar4 is a terphenyl group and

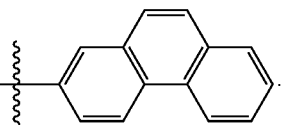

In the exemplary embodiment of the present specification, Ar4 is a substituted or unsubstituted fluorenyl group.

In the exemplary embodiment of the present specification, Ar4 is a fluorenyl group substituted by an alkyl group.

In the exemplary embodiment of the present specification, Ar4 is a fluorenyl group substituted by a methyl group.

In the exemplary embodiment of the present specification, Ar4 is a fluorenyl group substituted by an aryl group.

In the exemplary embodiment of the present specification, Ar4 is a fluorenyl group substituted by a phenyl group.

In the exemplary embodiment of the present specification, a second carbon position of the fluorenyl group and a hetero-cycle including one or two or more Ns may be connected.

In the exemplary embodiment of the present specification, Ar4 is a substituted or unsubstituted naphthyl group.

In the exemplary embodiment of the present specification, Ar4 is a naphthyl group.

In the exemplary embodiment of the present specification, Ar4 is a naphthyl group and

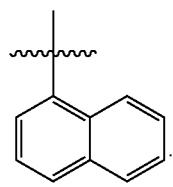 [SMILES: *c1cccc2ccccc12]

In the exemplary embodiment of the present specification, Ar4 is a naphthyl group and

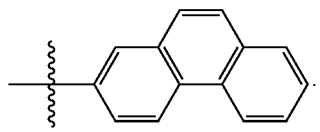 [SMILES: *c1ccc2c(ccc3ccccc32)c1]

In the exemplary embodiment of the present specification, Ar4 is a substituted or unsubstituted phenanthryl group.

In the exemplary embodiment of the present specification, Ar4 is a phenanthryl group.

In the exemplary embodiment of the present specification, Ar4 is a phenanthryl group and

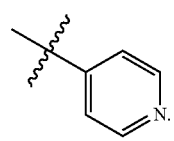 [SMILES: *c1ccncc1]

In the exemplary embodiment of the present specification, Ar4 is a substituted or unsubstituted hetero-cyclic group including one or more of O, N, and S as a substituted or unsubstituted hetero element.

In the exemplary embodiment of the present specification, Ar4 is a substituted or unsubstituted pyridine group.

In the exemplary embodiment of the present specification, Ar4 is a pyridine group.

In the exemplary embodiment of the present specification, Ar4 is a pyridine group and

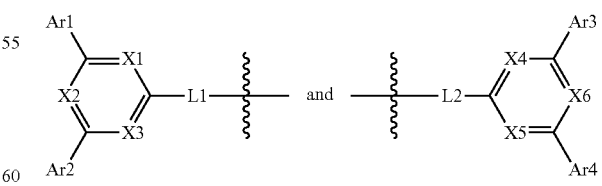

In the exemplary embodiment of the present specification, Ar4 is a substituted or unsubstituted thiophene group.

In the exemplary embodiment of the present specification, Ar4 is a thiophene group.

In the exemplary embodiment of the present specification,

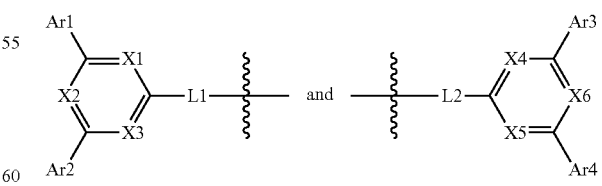

are the same as each other.

In the exemplary embodiment of the present specification, the hetero-cyclic compound represented by Chemical Formula 1 is represented by any one of the following Chemical Formulas 1-1 to 1-50.

Chemical Formula 1-1
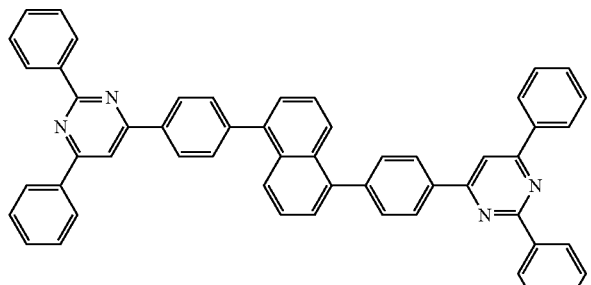
Chemical Formula 1-2
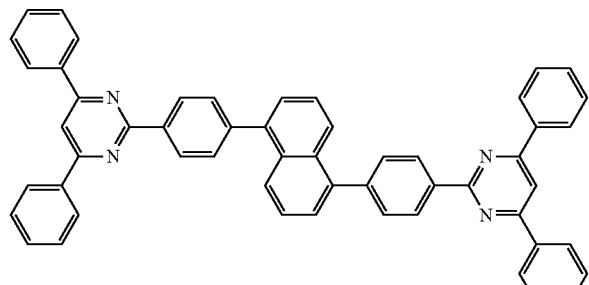
Chemical Formula 1-3
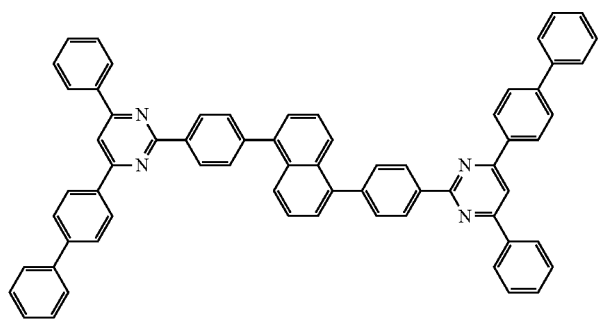
Chemical Formula 1-4
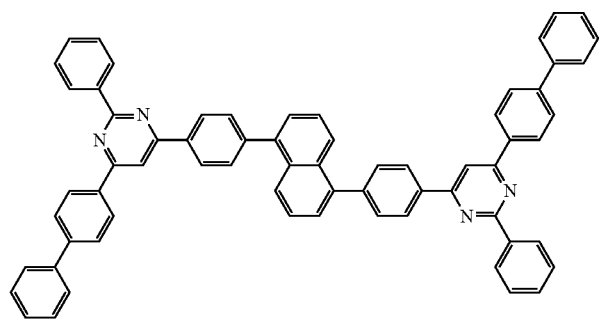
Chemical Formula 1-5
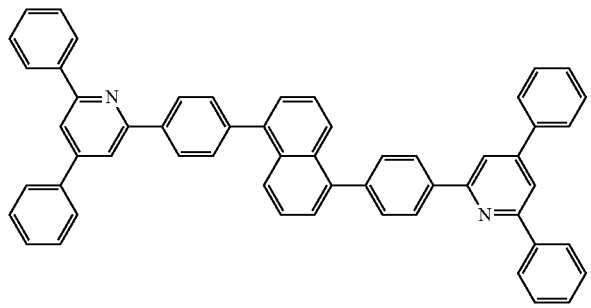
Chemical Formula 1-6
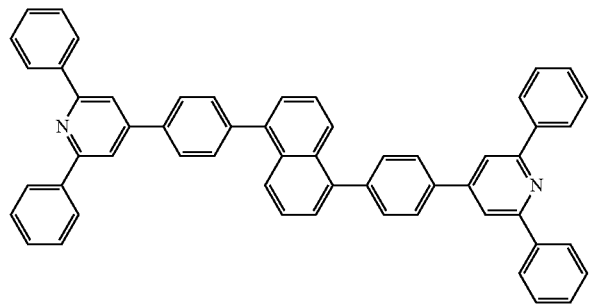
Chemical Formula 1-7
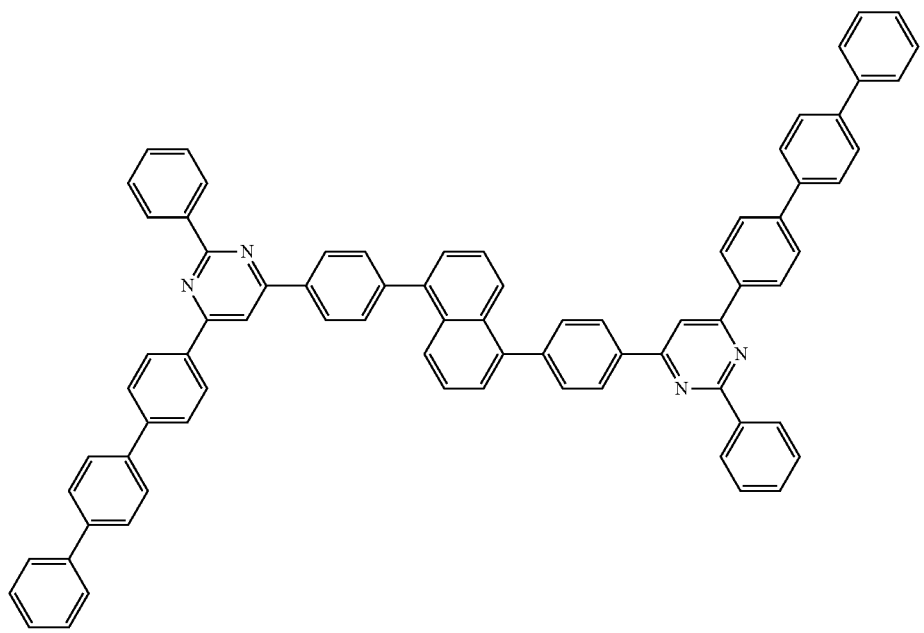

Chemical Formula 1-8
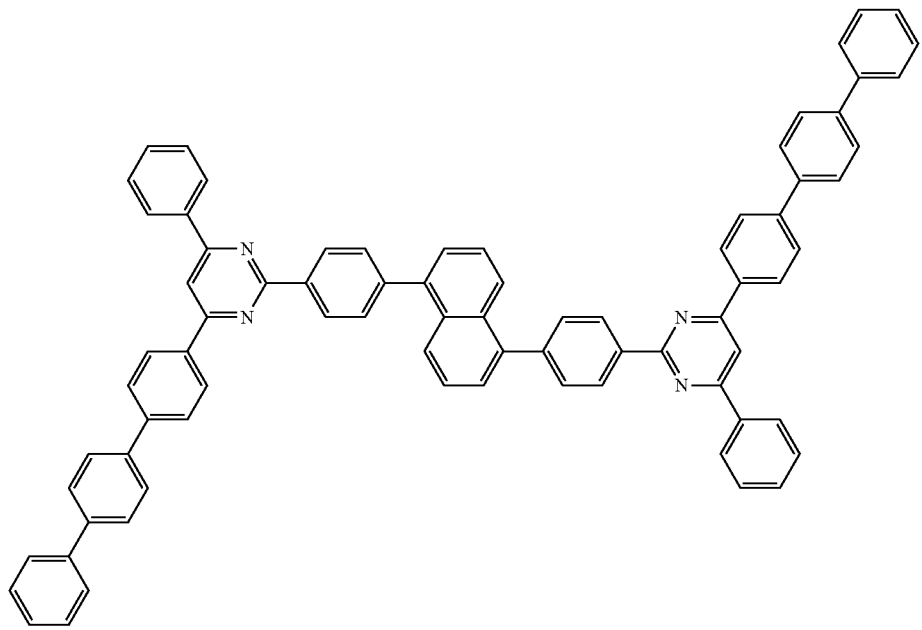
Chemical Formula 1-9
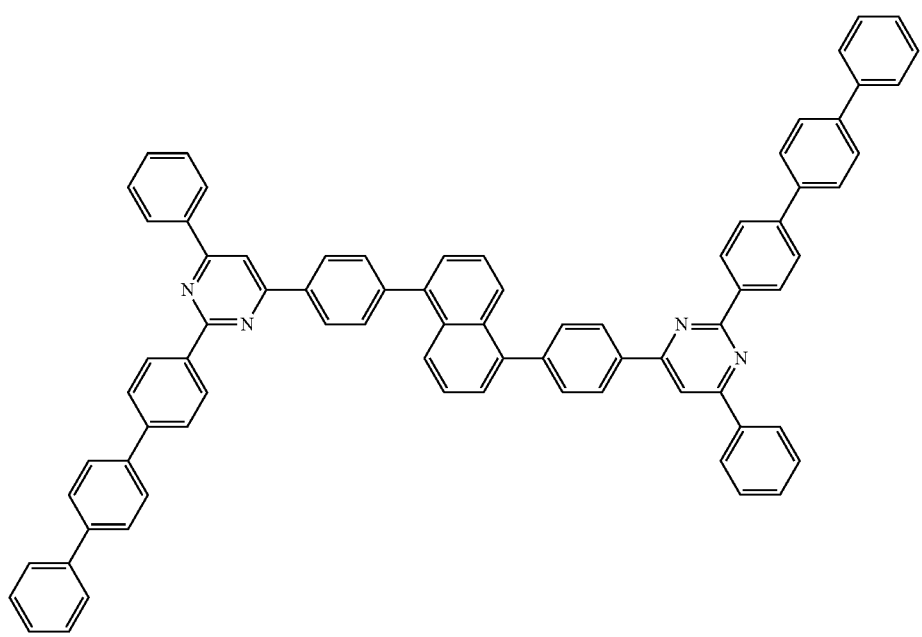
Chemical Formula 1-10
Chemical Formula 1-11
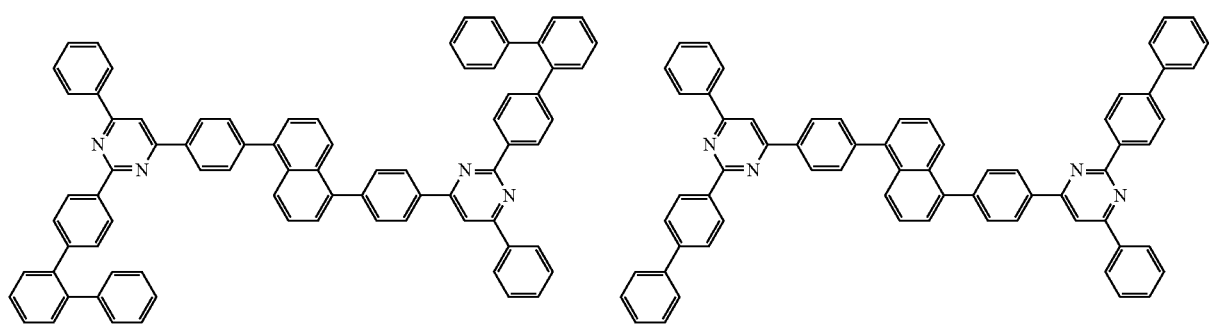

-continued
Chemical Formula 1-12
Chemical Formula 1-13
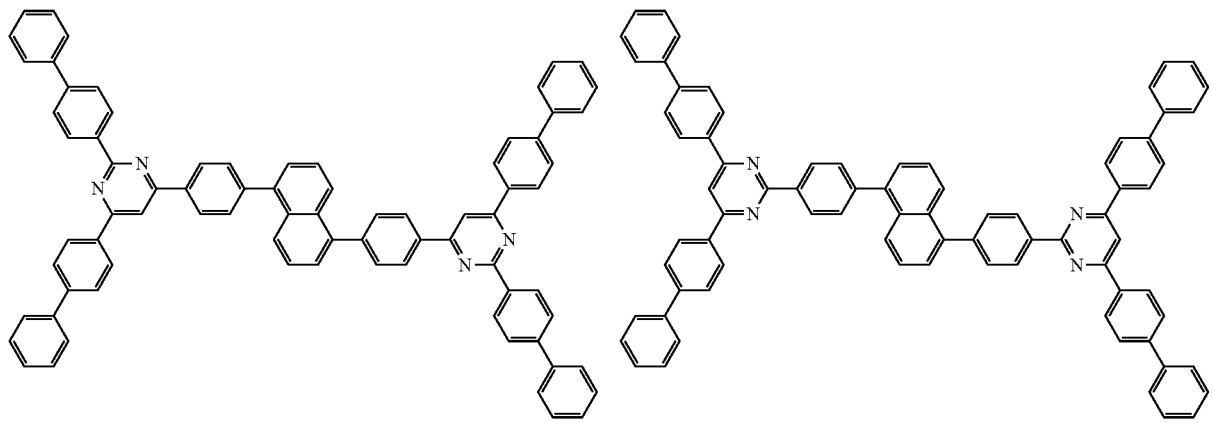
Chemical Formula 1-14
Chemical Formula 1-15
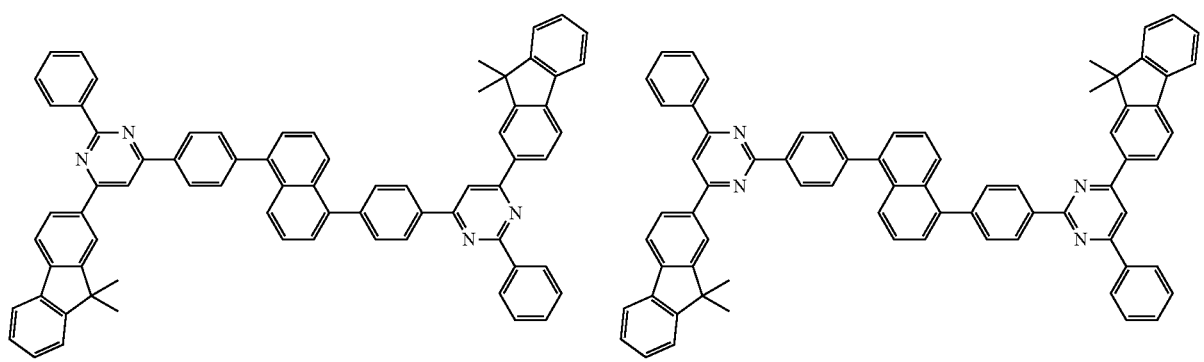
Chemical Formula 1-16
Chemical Formula 1-17
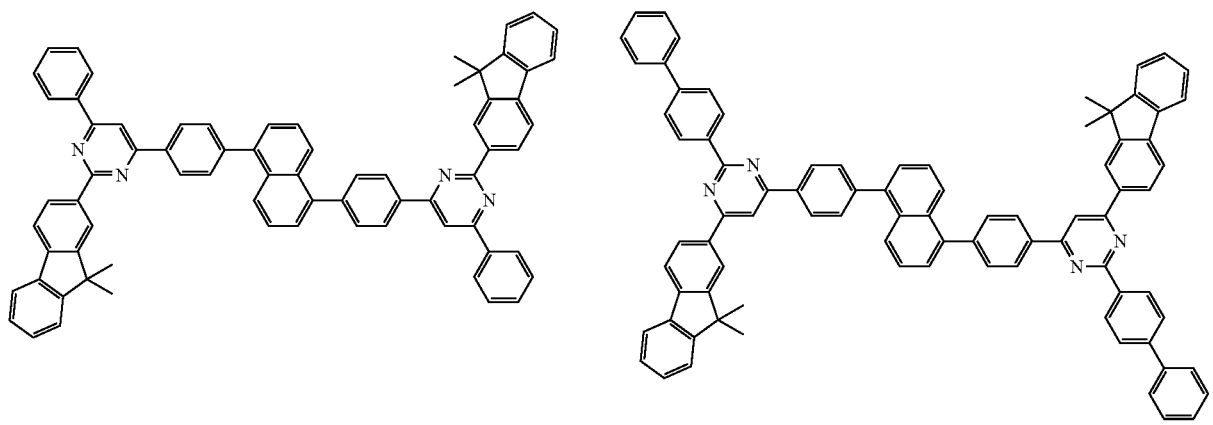

Chemical Formula 1-18
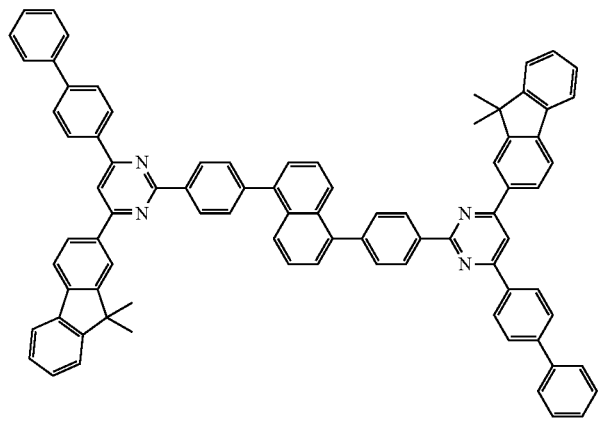
Chemical Formula 1-19
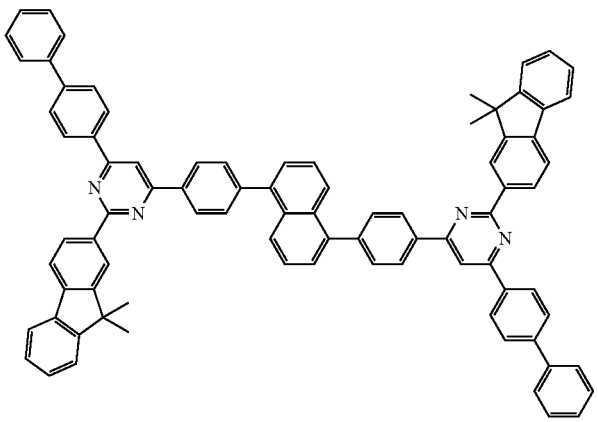
Chemical Formula 1-20
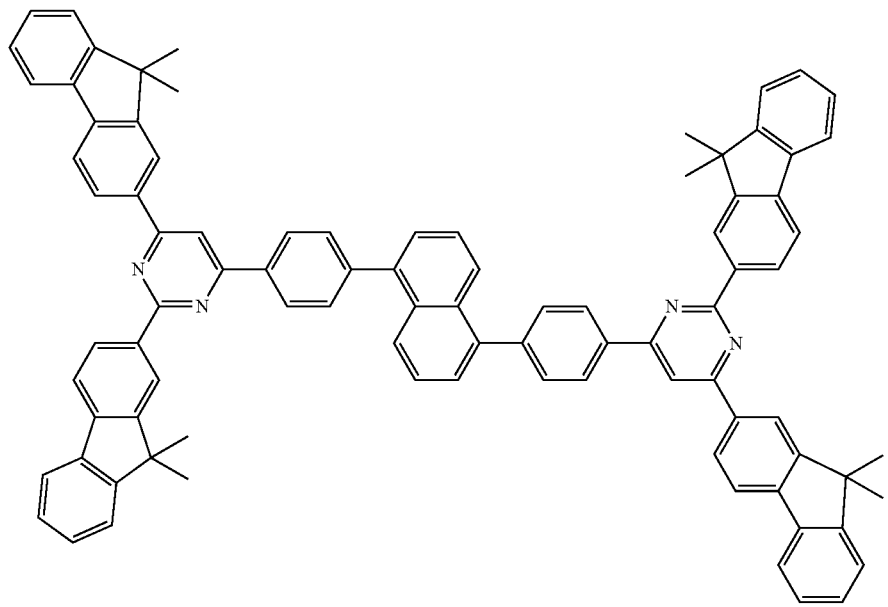
Chemical Formula 1-21
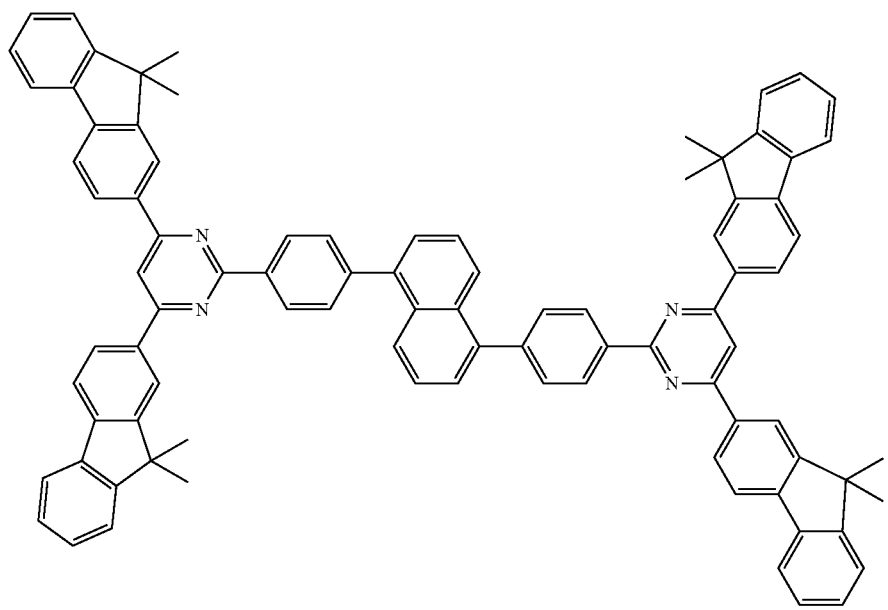

-continued
Chemical Formula 1-22
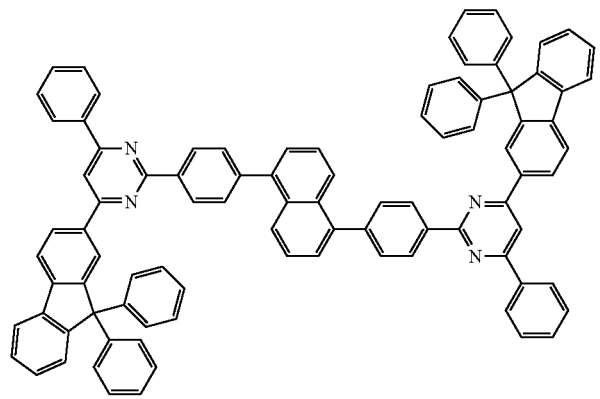
Chemical Formula 1-23
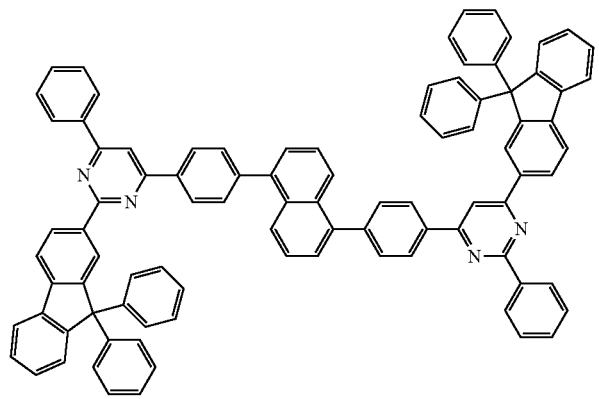
Chemical Formula 1-24
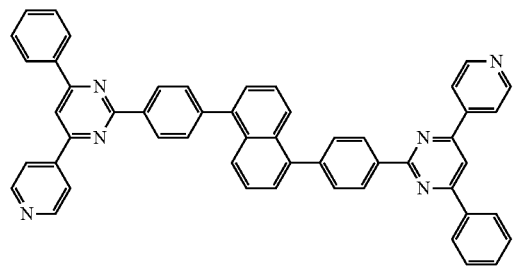
Chemical Formula 1-25
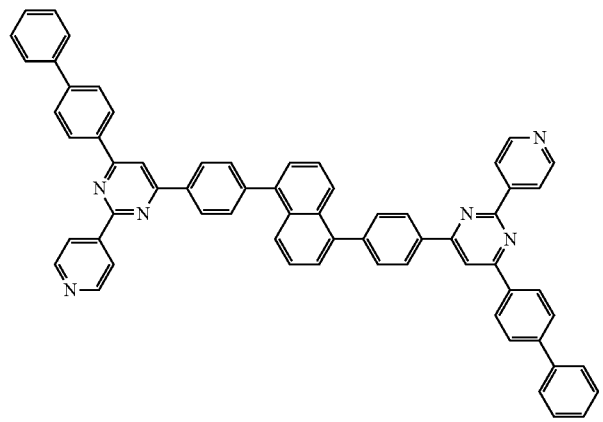
Chemical Formula 1-26
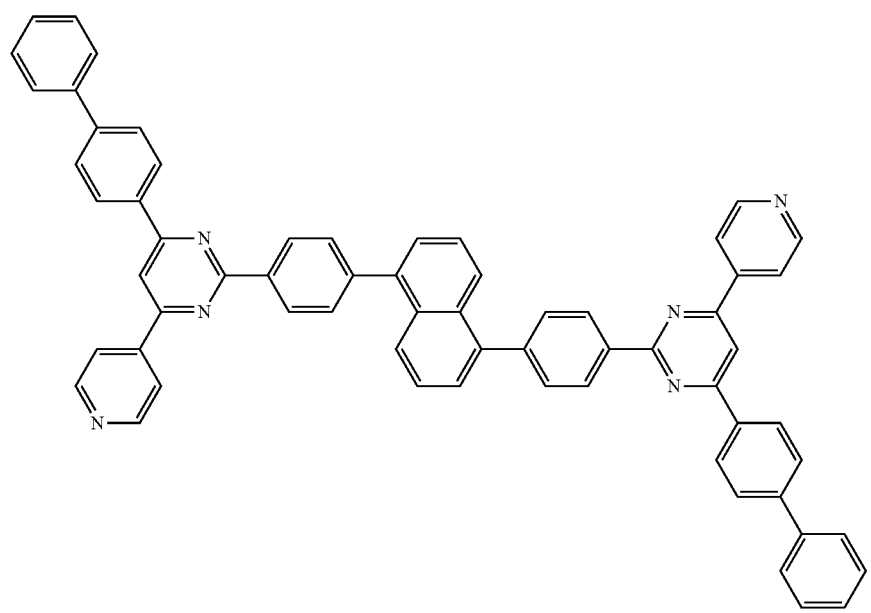

-continued
Chemical Formula 1-27
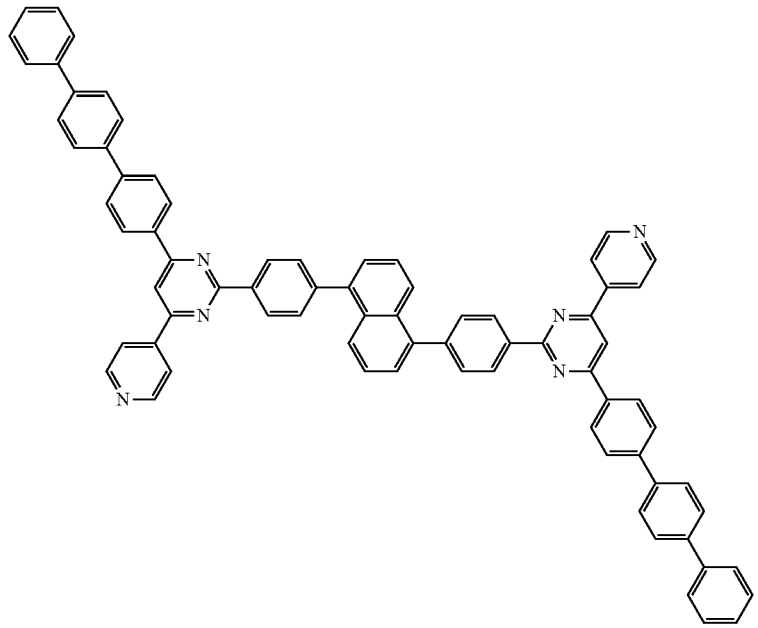
Chemical Formula 1-28         Chemical Formula 1-29
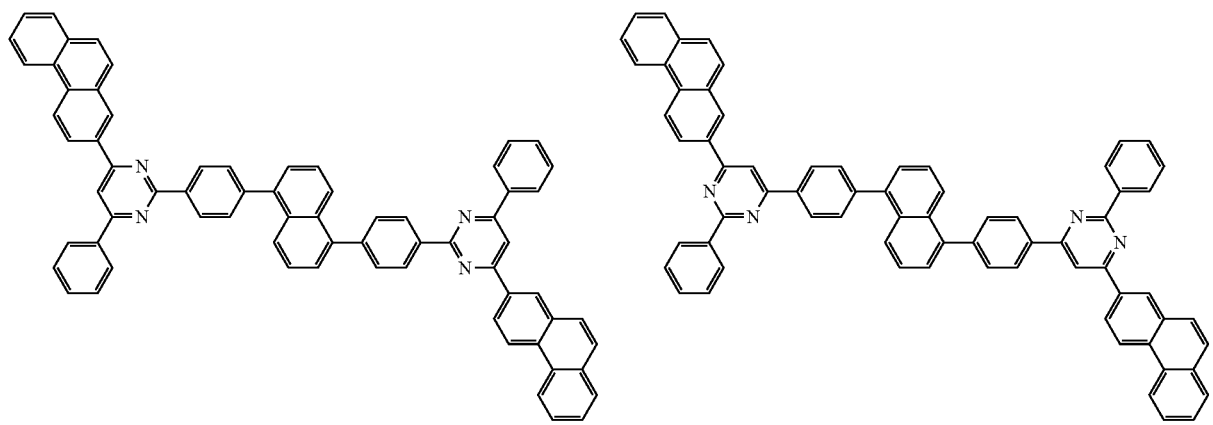
Chemical Formula 1-30         Chemical Formula 1-31
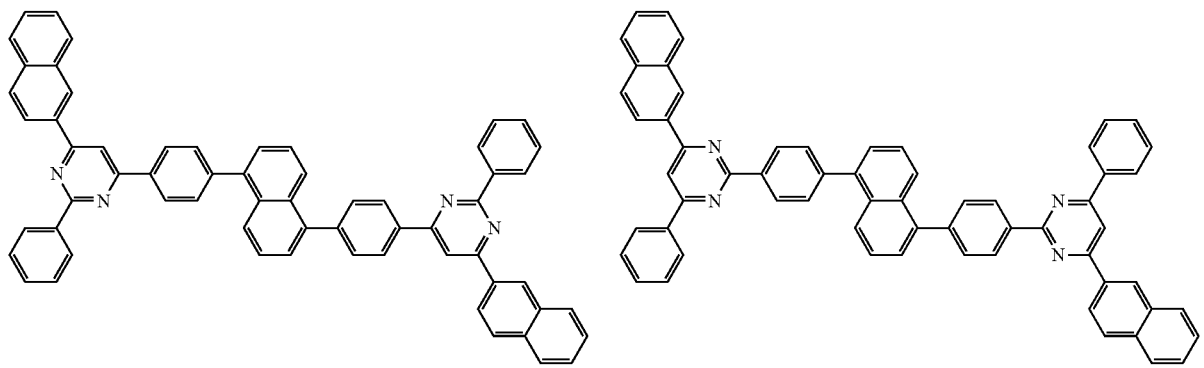

-continued
Chemical Formula 1-32
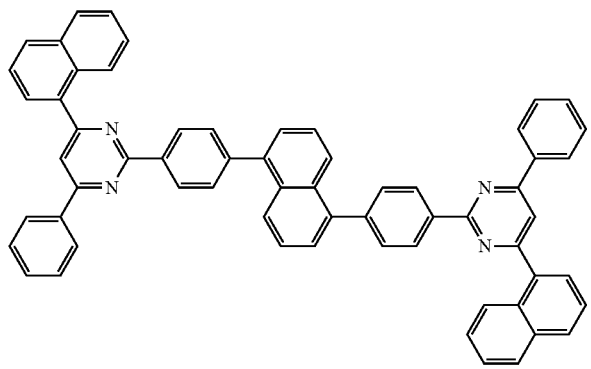
Chemical Formula 1-33
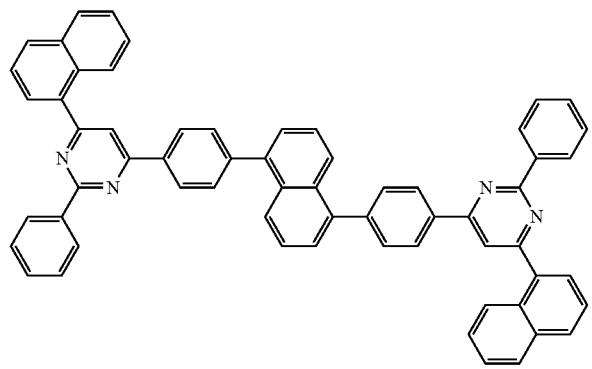
Chemical Formula 1-34
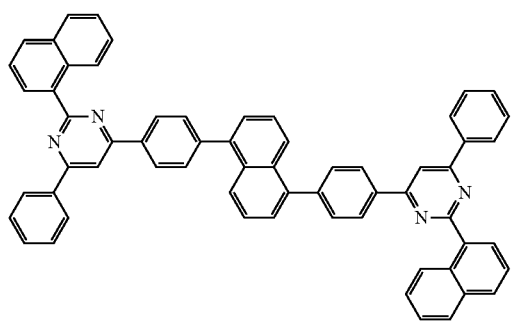
Chemical Formula 1-35
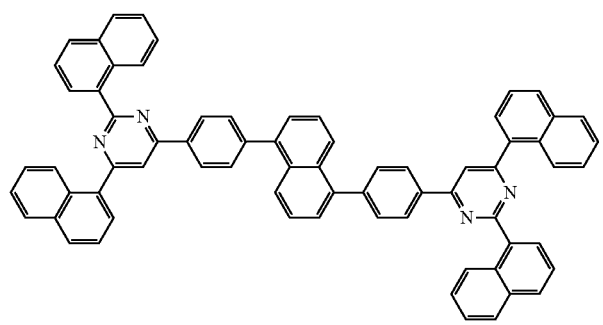
Chemical Formula 1-36
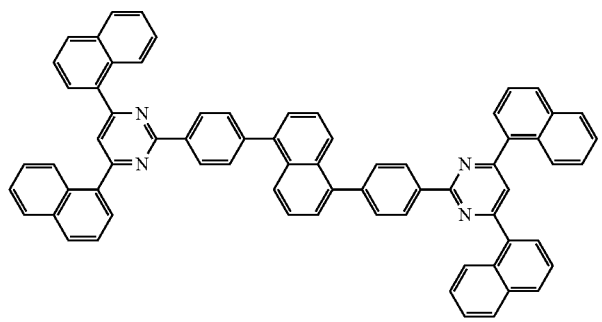
Chemical Formula 1-37
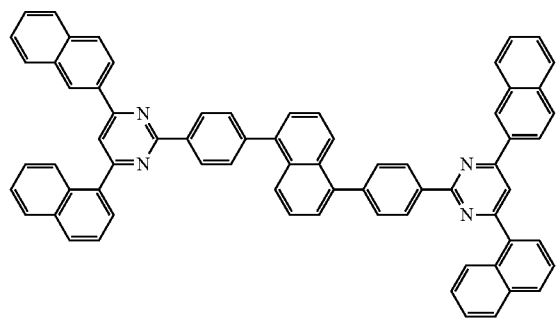
Chemical Formula 1-38
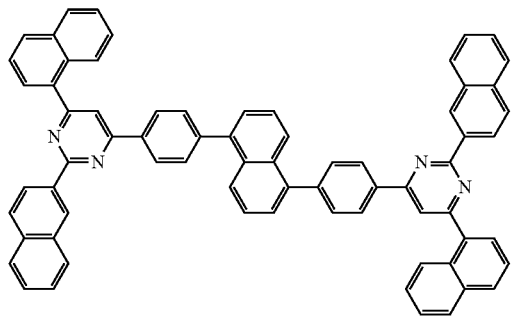
Chemical Formula 1-39
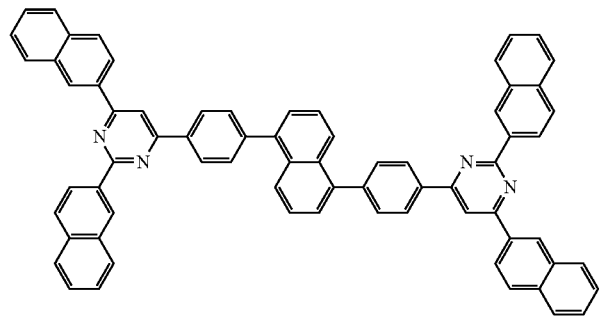

-continued
Chemical Formula 1-40
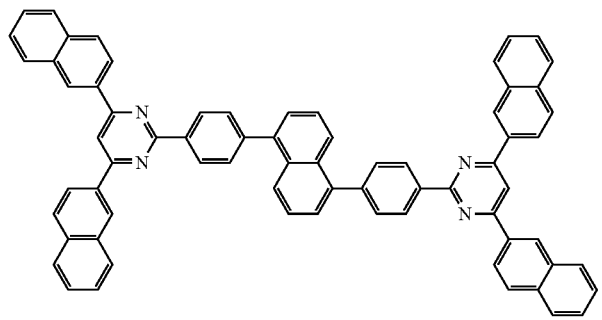
Chemical Formula 1-41
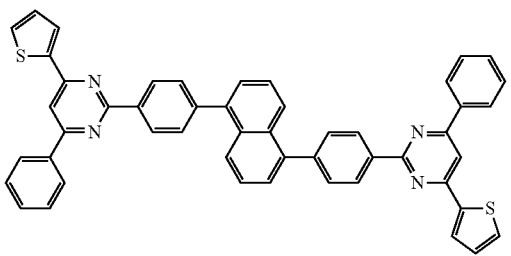
Chemical Formula 1-42
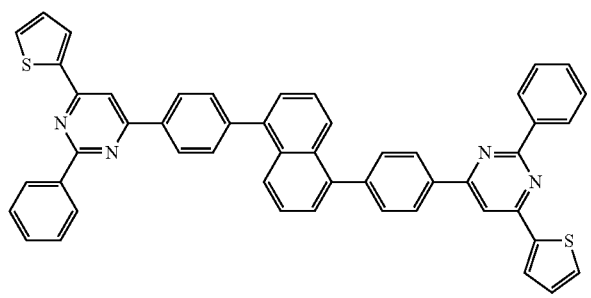
Chemical Formula 1-43
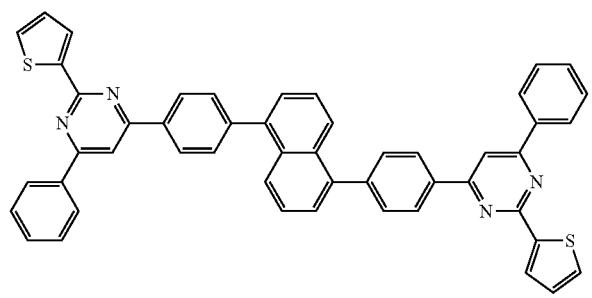
Chemical Formula 1-44
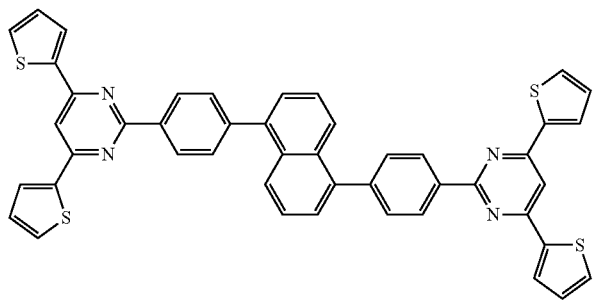
Chemical Formula 1-45
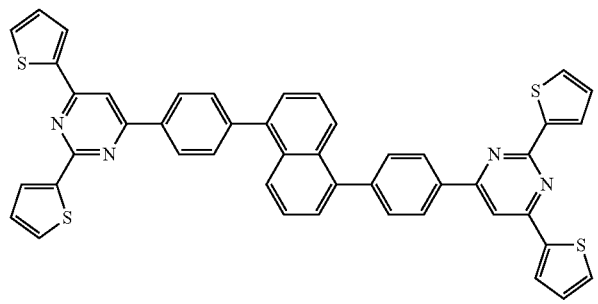
Chemical Formula 1-46
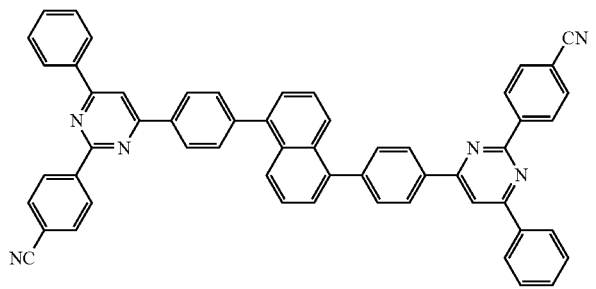
Chemical Formula 1-47
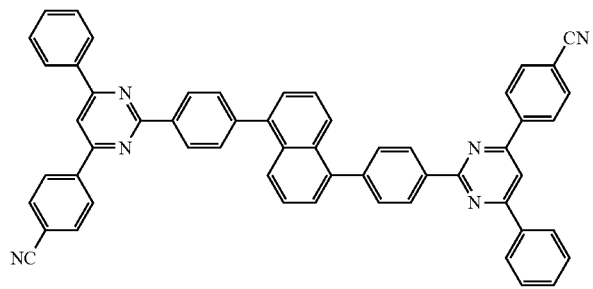

Chemical Formula 1-48
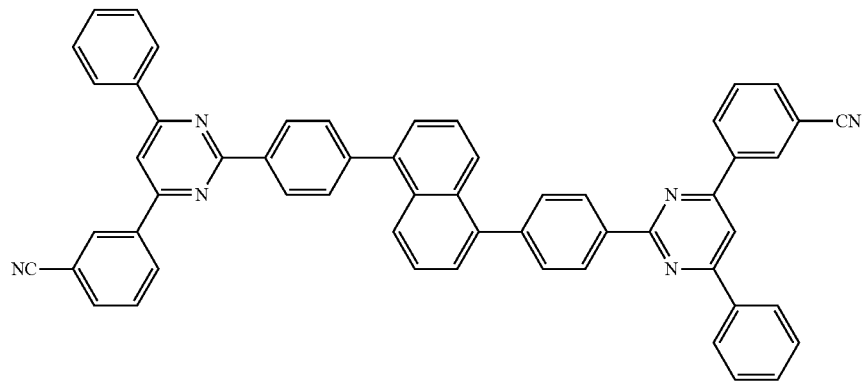
Chemical Formula 1-49
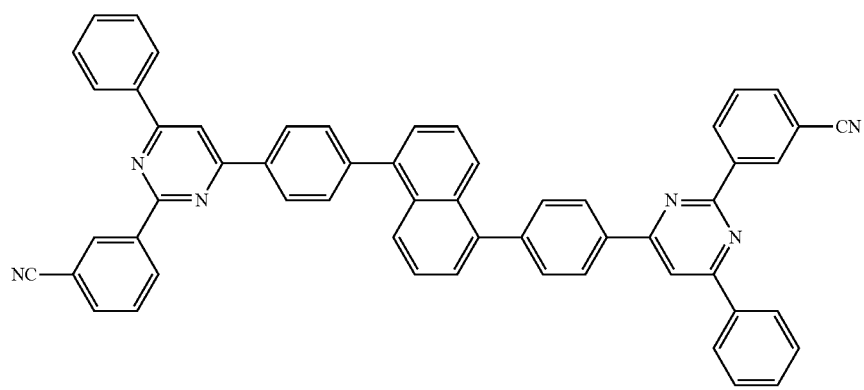
Chemical Formula 1-50
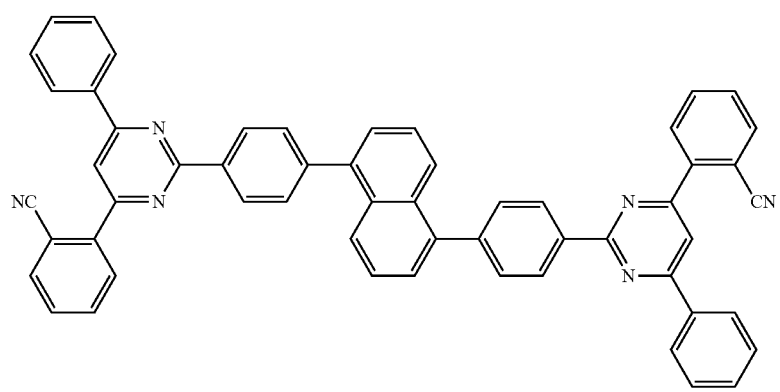

In the exemplary embodiment of the present specification, the hetero-cyclic compound represented by Chemical Formula 1 is any one of the following Chemical Formulas 2-1 to 2-50.
Chemical Formula 2-1
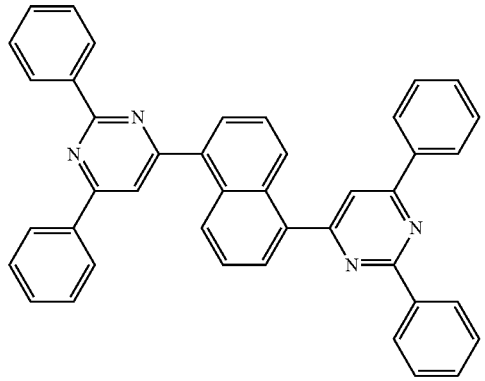
Chemical Formula 2-2
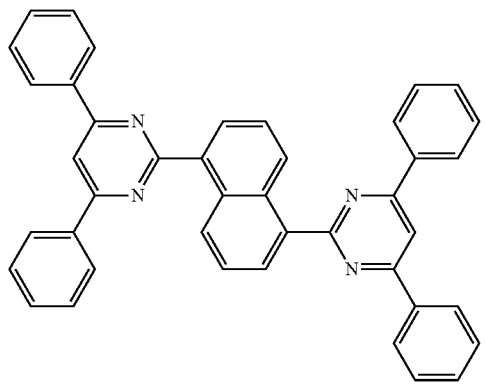
Chemical Formula 2-3
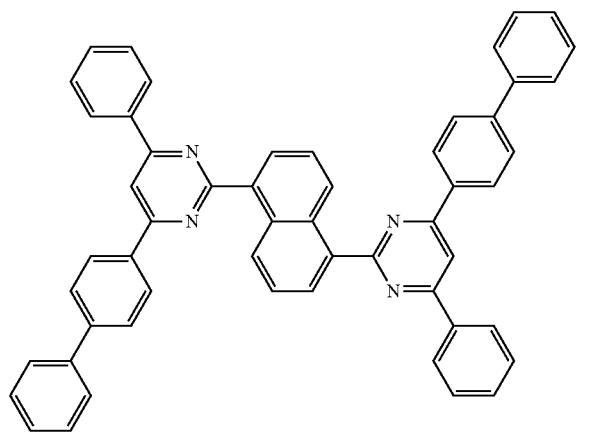
Chemical Formula 2-4
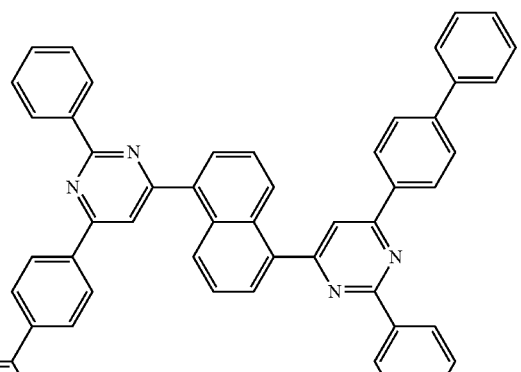
Chemical Formula 2-5
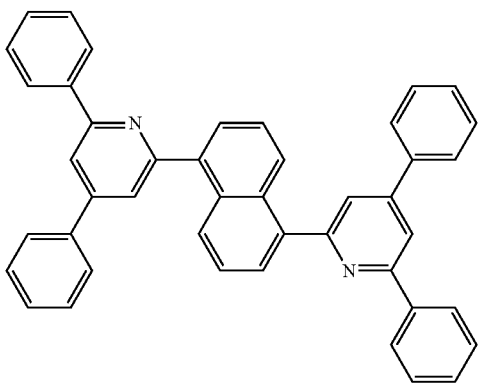
Chemical Formula 2-6
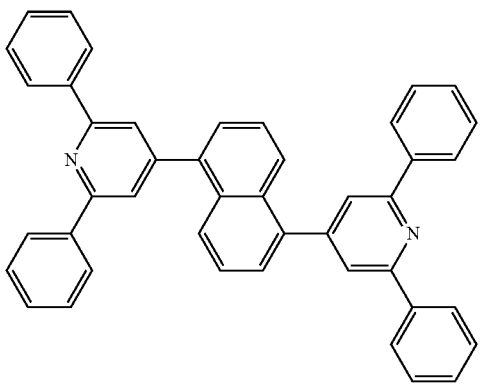

Chemical Formula 2-7
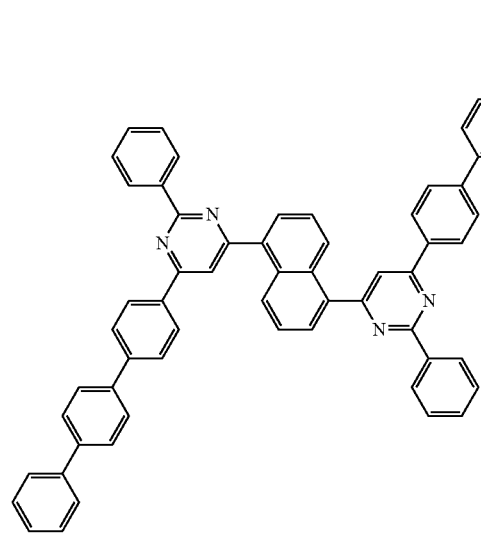
Chemical Formula 2-8
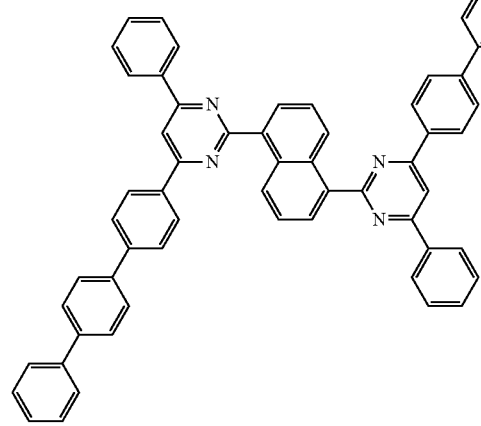
Chemical Formula 2-9
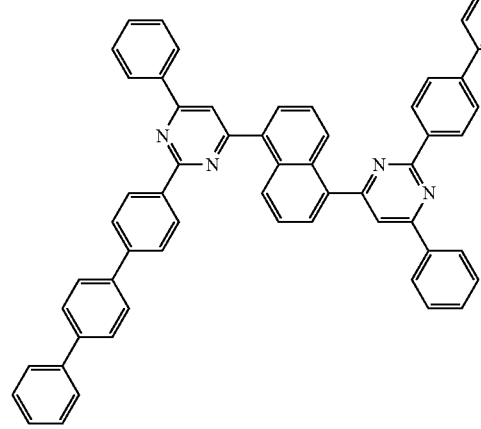
Chemical Formula 2-10
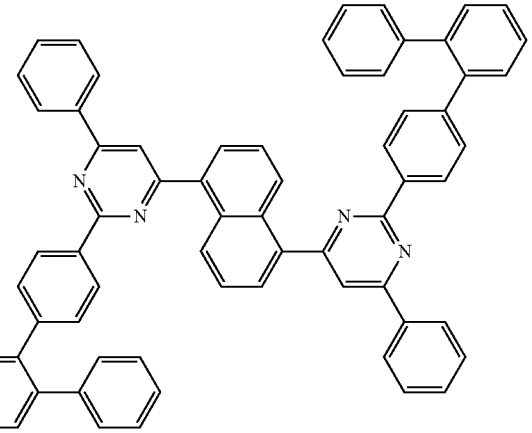
Chemical Formula 2-11
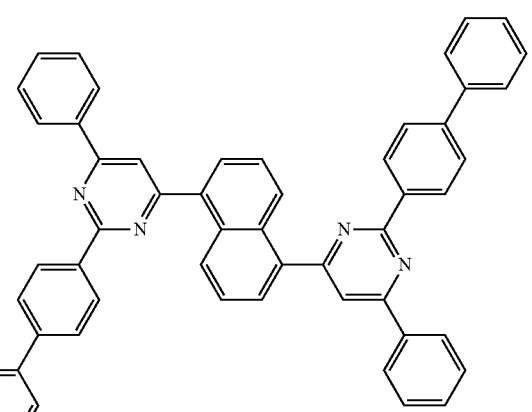
Chemical Formula 2-12
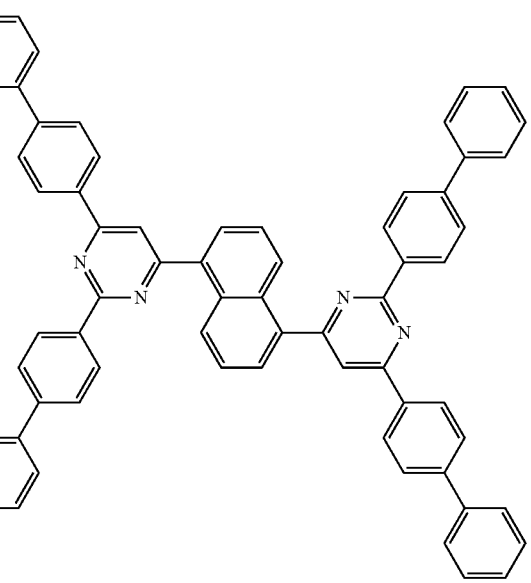

Chemical Formula 2-13
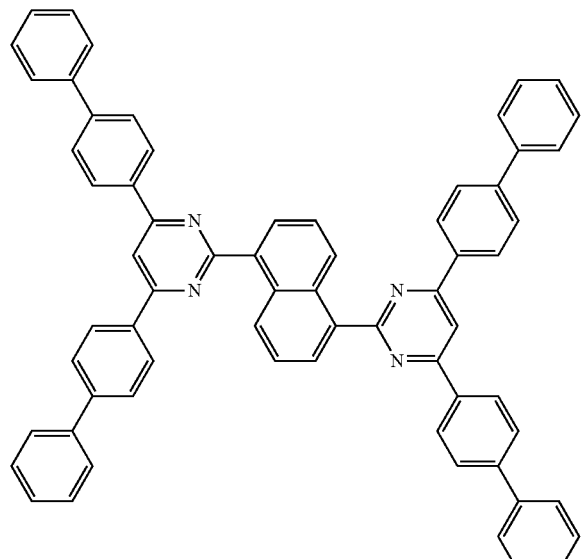
Chemical Formula 2-16
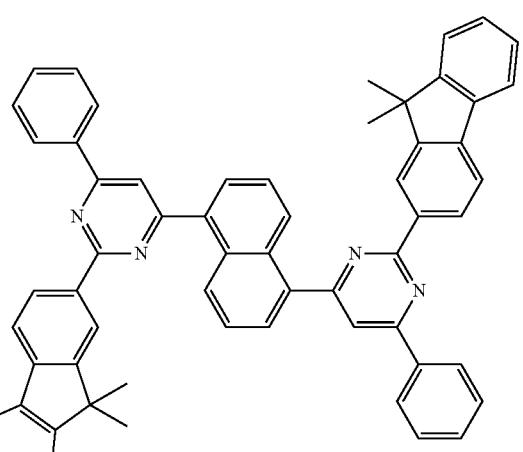
Chemical Formula 2-14
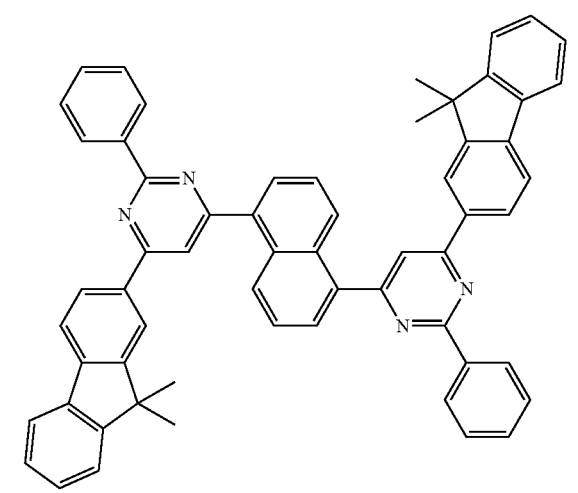
Chemical Formula 2-17
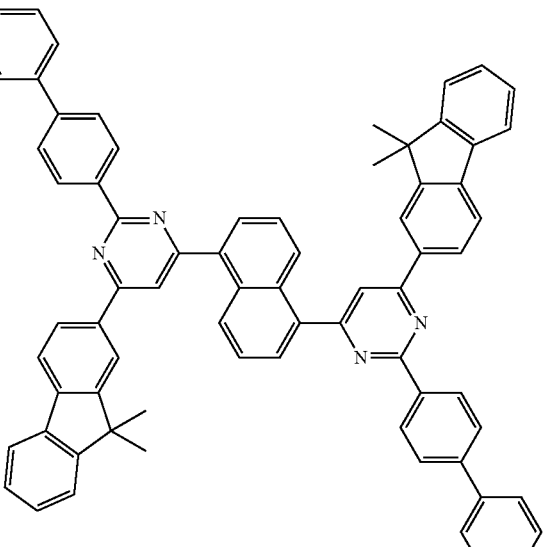
Chemical Formula 2-15
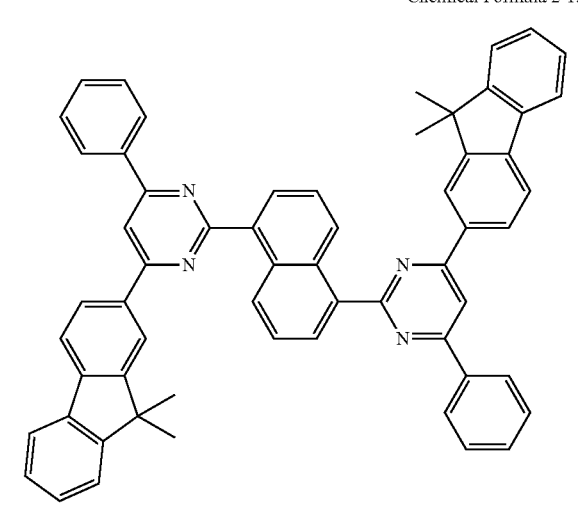

Chemical Formula 2-18
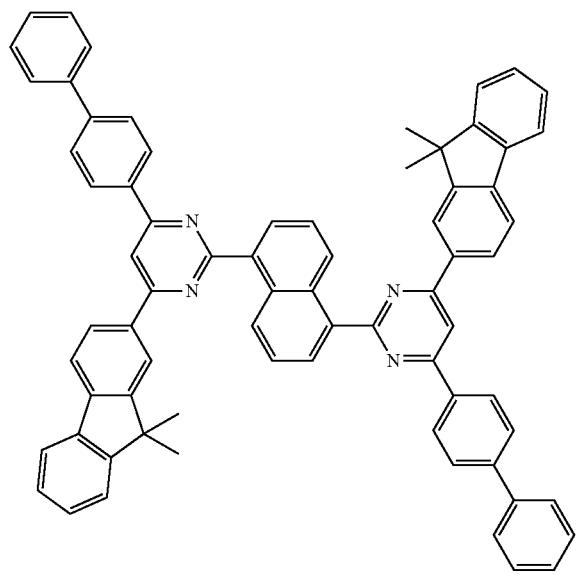
Chemical Formula 2-20
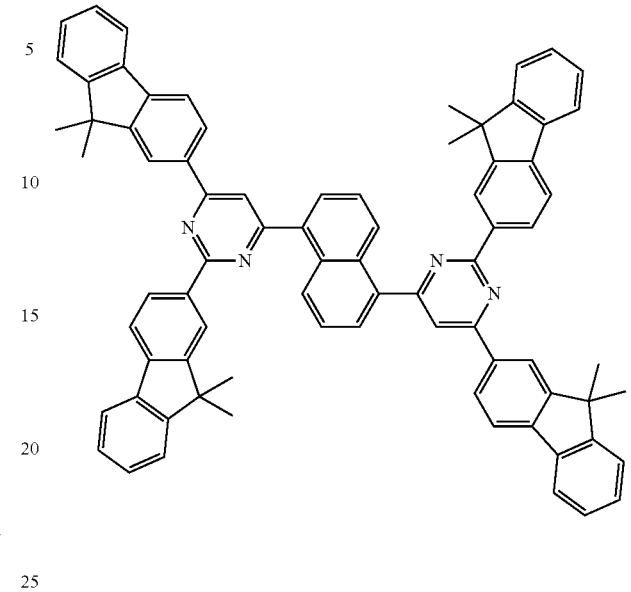
Chemical Formula 2-21
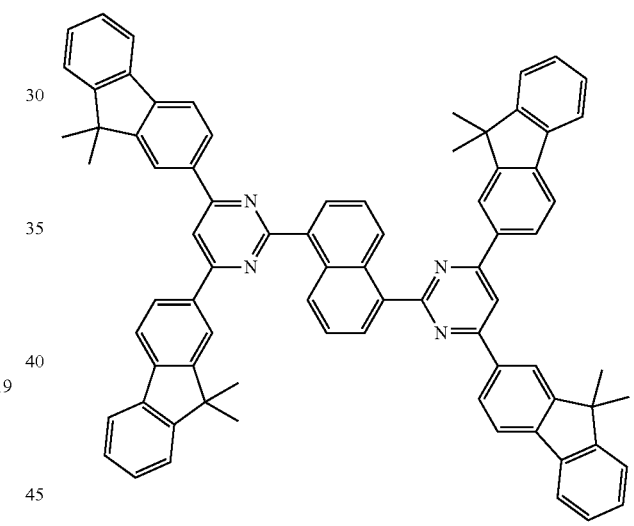
Chemical Formula 2-19
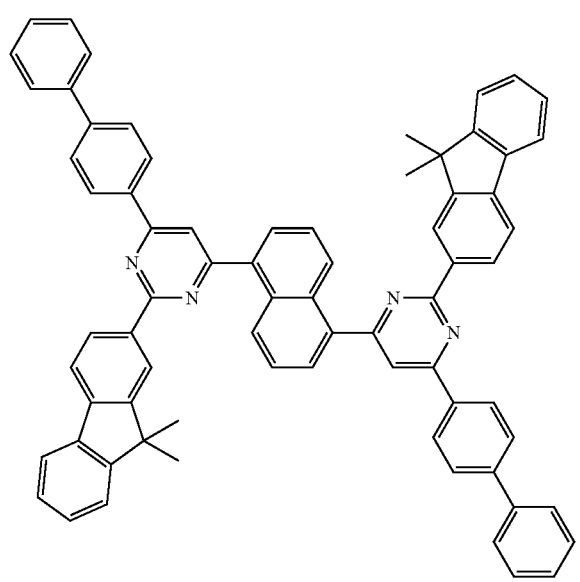
Chemical Formula 2-22
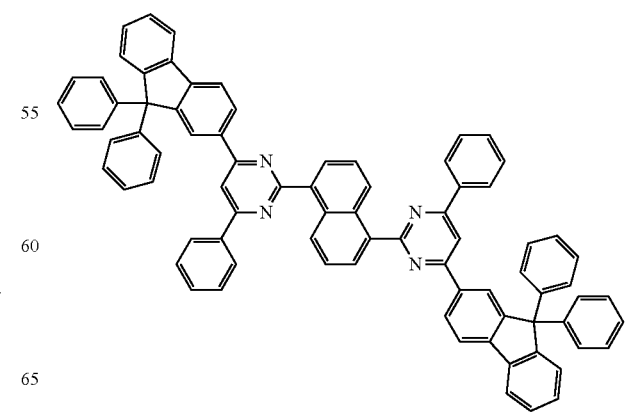

Chemical Formula 2-23
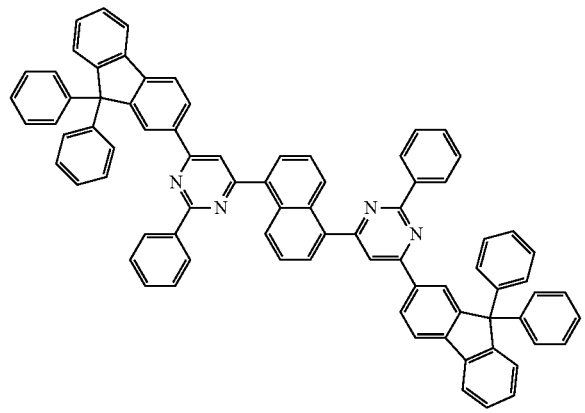
Chemical Formula 2-24
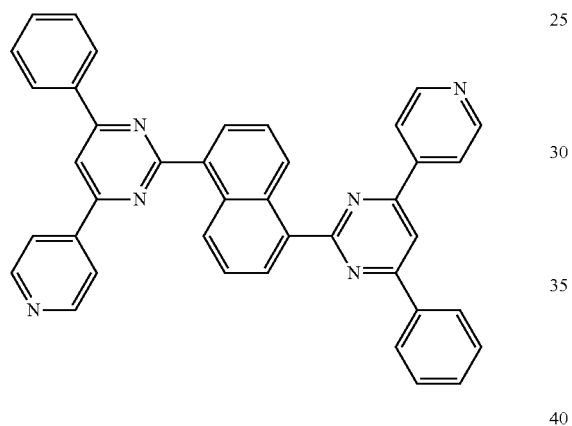
Chemical Formula 2-25
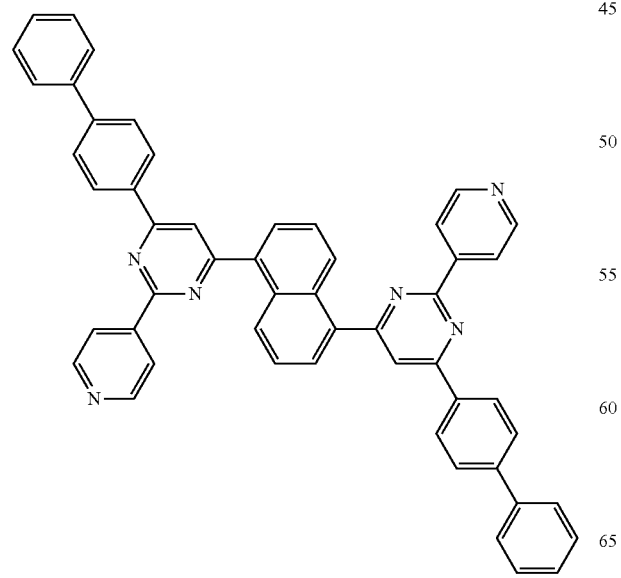
Chemical Formula 2-26
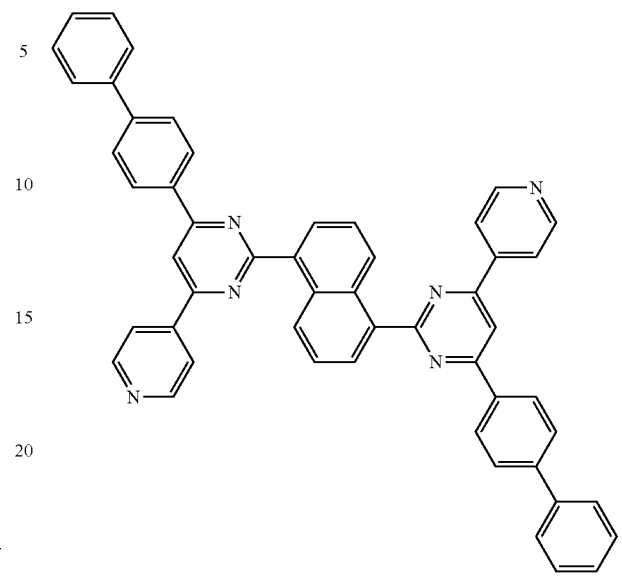
Chemical Formula 2-27
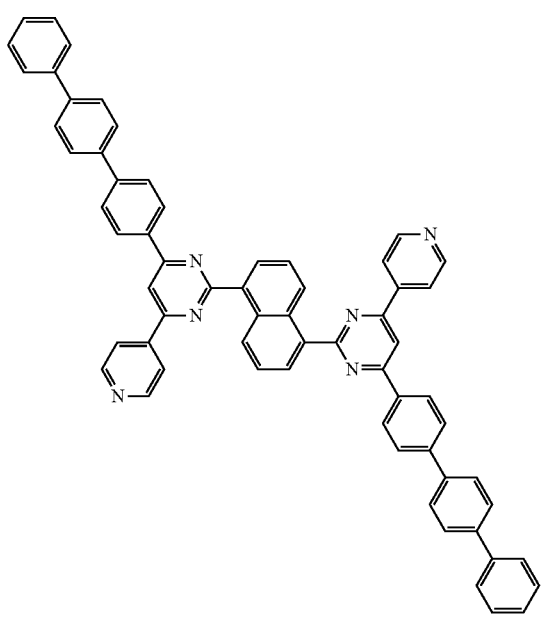

Chemical Formula 2-28
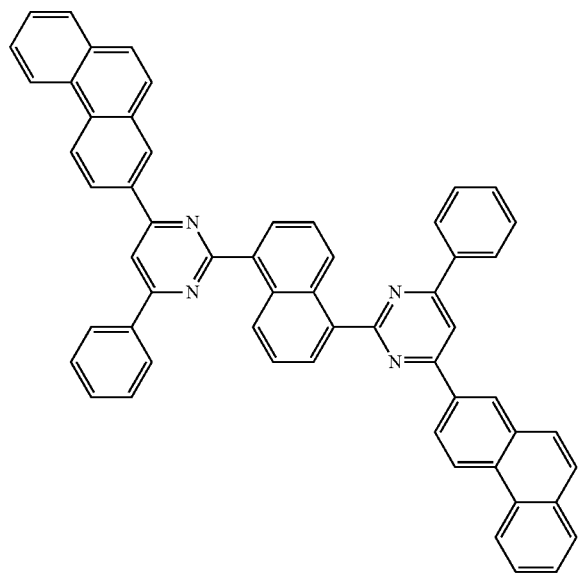
Chemical Formula 2-29
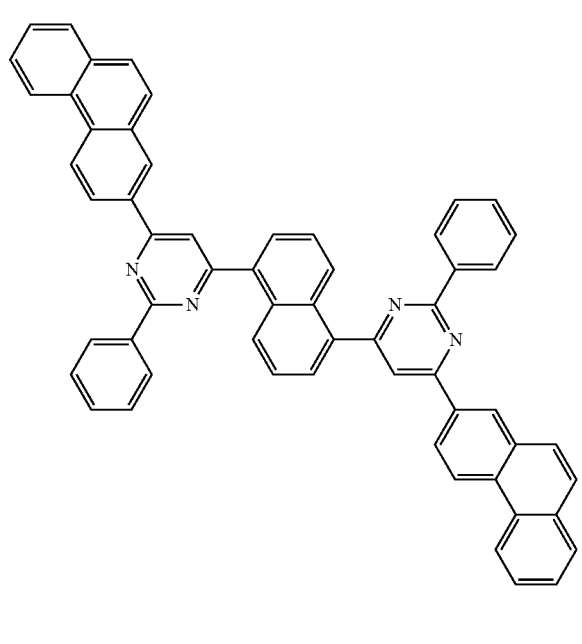
Chemical Formula 2-30
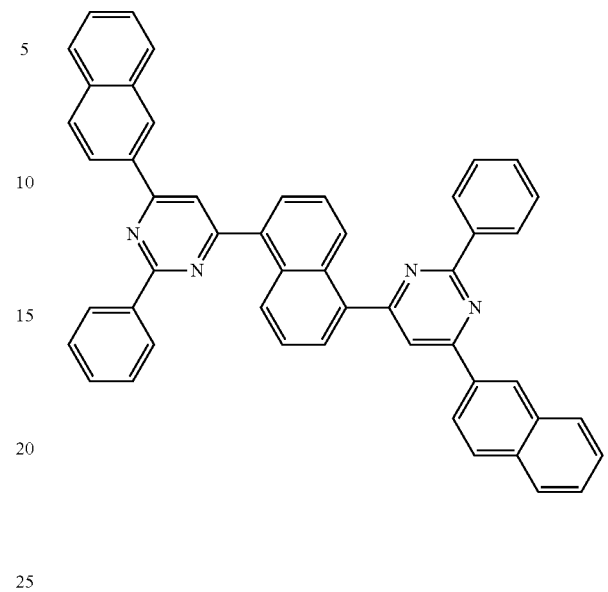
Chemical Formula 2-31
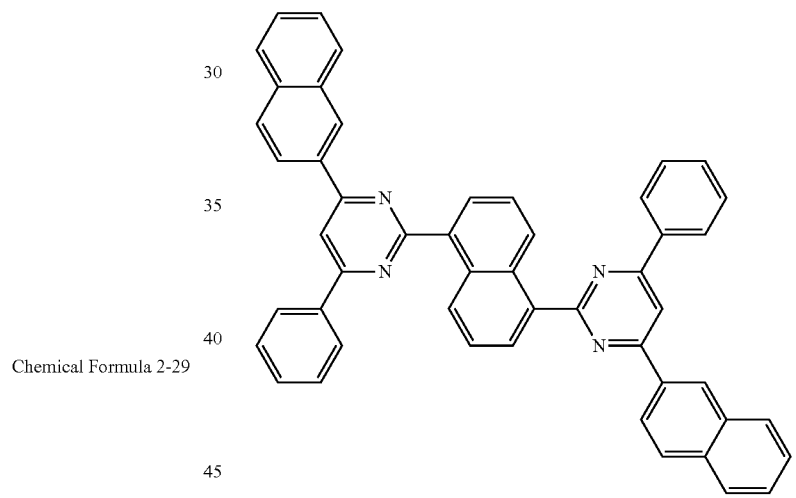
Chemical Formula 2-32
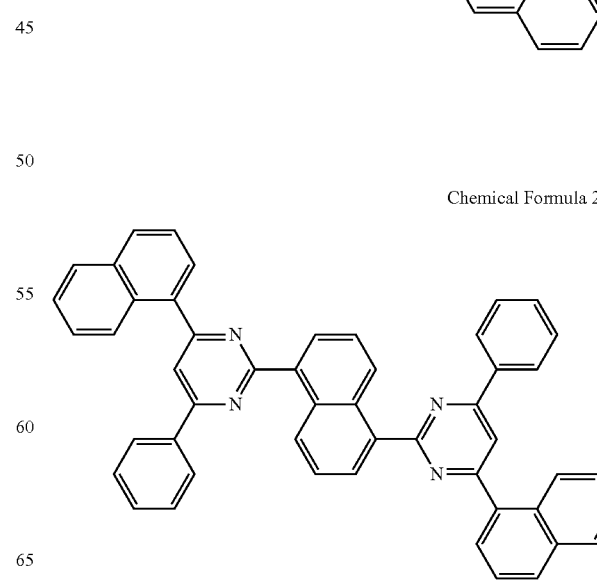

Chemical Formula 2-33
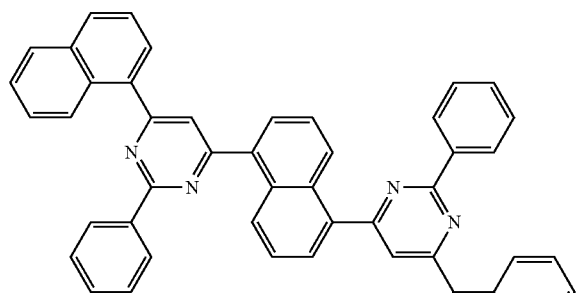
Chemical Formula 2-34
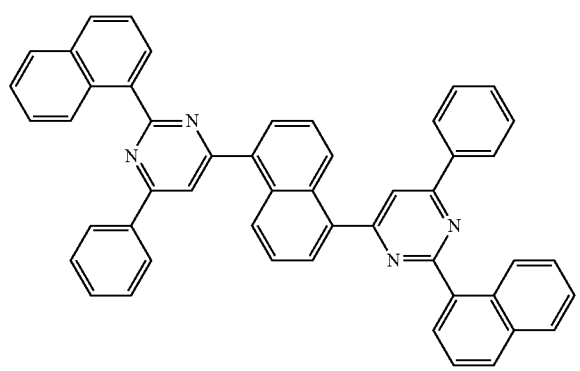
Chemical Formula 2-35
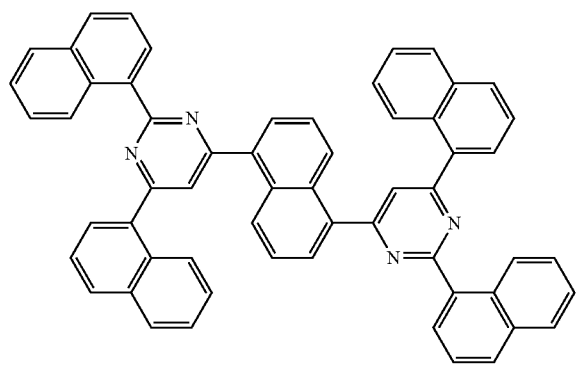
Chemical Formula 2-36
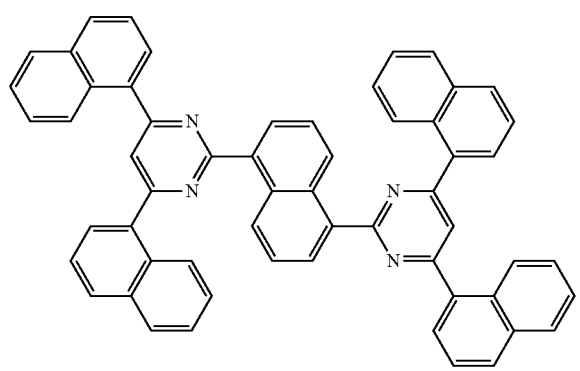
Chemical Formula 2-37
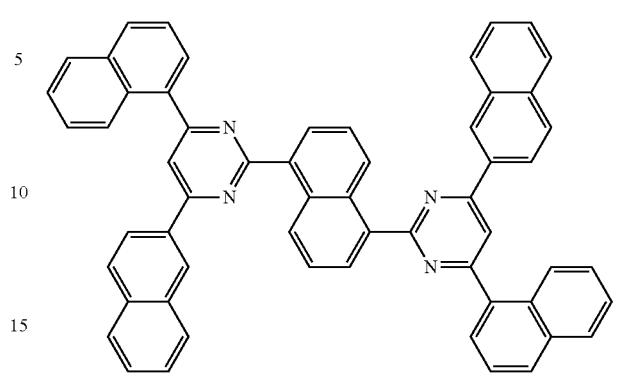
Chemical Formula 2-38
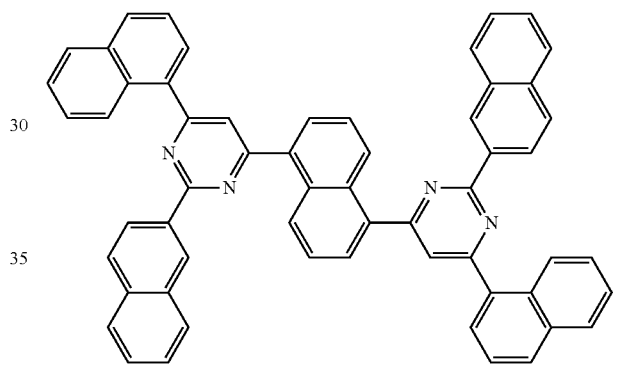
Chemical Formula 2-39
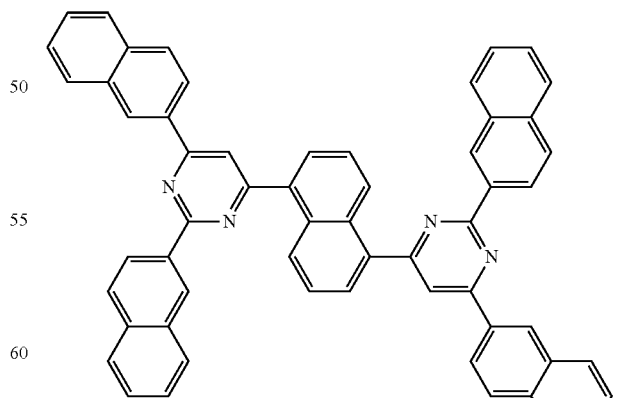

Chemical Formula 2-40
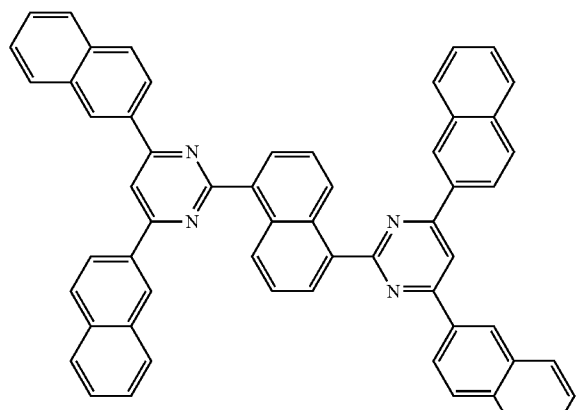
Chemical Formula 2-41
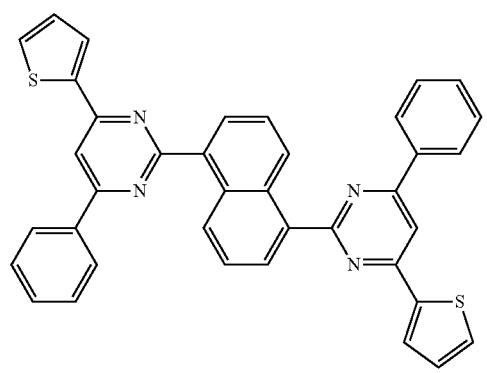
Chemical Formula 2-42
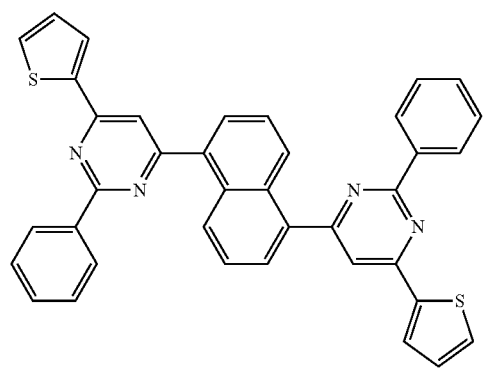
Chemical Formula 2-43
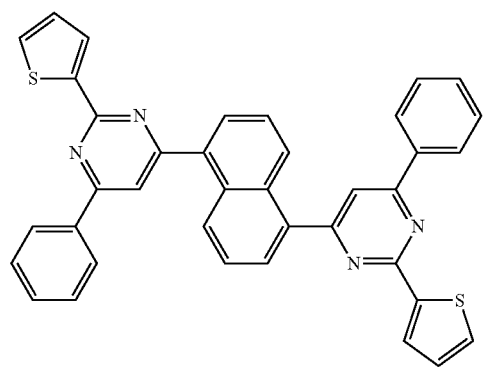
Chemical Formula 2-44
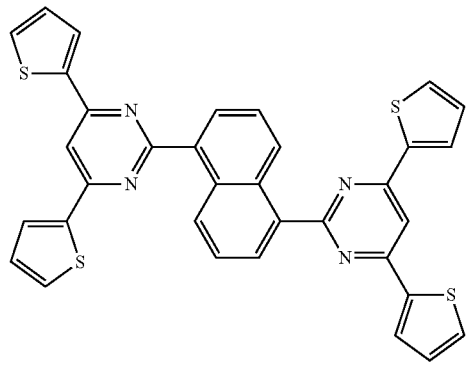
Chemical Formula 2-45
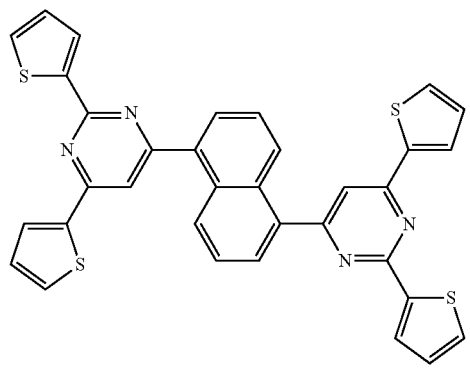
Chemical Formula 2-46
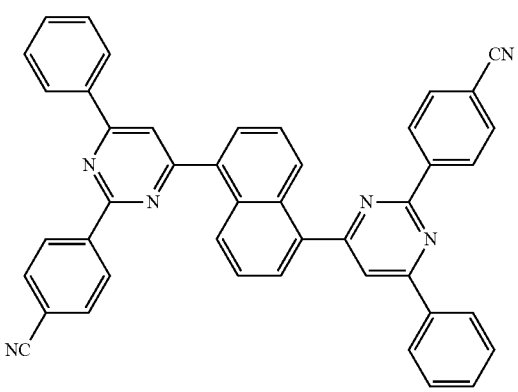
Chemical Formula 2-47
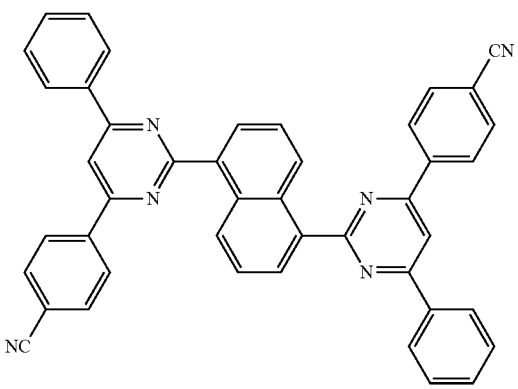

-continued

Chemical Formula 2-48

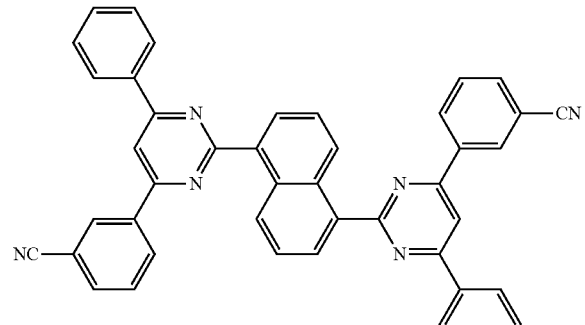

Chemical Formula 2-49

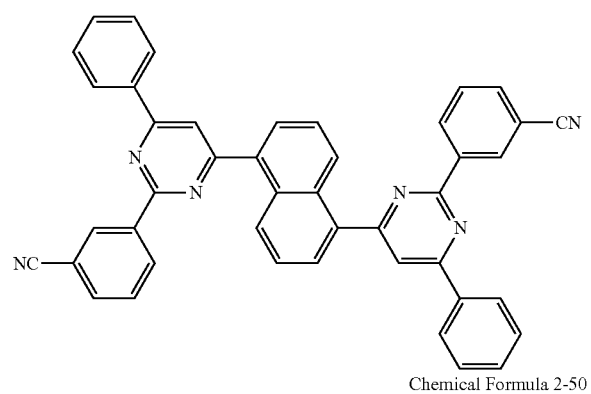

Chemical Formula 2-50

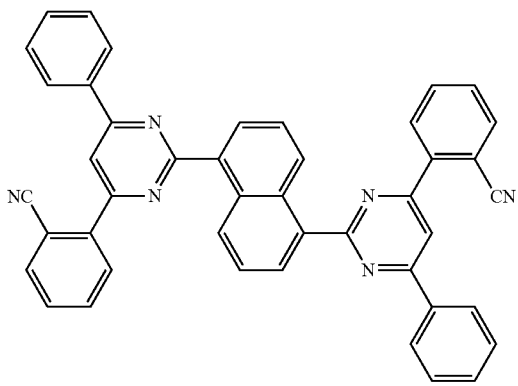

As shown in Chemical Formula 1, the compound of Chemical Formula 1 may have a property that is suitable to be used as the organic material layer used in the organic light emitting device by introducing substituent groups including a hetero-cycle into both sides on the basis of a naphthalene group.

Since the compound represented by Chemical Formula 1 includes a hetero-cyclic structure, the compound may have an appropriate energy level as an electron injection and/or electron transport material in the organic light emitting device. Further, in the present specification, it is possible to implement a device having a low driving voltage and high light efficiency by selecting the compound having an appropriate energy level according to the substituent group among the compounds represented by Chemical Formula 1 and using the compound in the organic light emitting device.

Further, various substituent groups are introduced to a core structure, so that an energy band gap can be finely adjusted, a property at an interface between organic materials can be improved, and the material may be used for various purposes.

Meanwhile, since the compound of Chemical Formula 1 has a high glass transition temperature (Tg), thermal stability is excellent. Such increase in thermal stability is an important factor providing driving stability to the device.

The compounds represented by Chemical Formula 1 may be prepared based on Preparation Examples as will be described later.

The compound represented by Chemical Formula 1 may be prepared by a structure where Ar1, Ar2, and L1 are substituted at a hetero-cycle including X1 to X3 in a 1,5-naphthyl group and a method of bonding Ar3, Ar4, and L2 to the hetero-cycle including X4 to X6.

The hetero-cyclic compound represented by Chemical Formula 1 may be prepared by changing the number of hetero atoms of X1 to X6, Ar1 to Ar4, L1, and L2.

Further, the present specification provides an organic light emitting device including the hetero-cyclic compound represented by Chemical Formula 1.

In the exemplary embodiment of the present specification, there is provided an organic light emitting device including: a first electrode; a second electrode provided to face the first electrode; and one or more organic material layers including a light emitting layer provided between the first electrode and the second electrode, in which one or more layers of the organic material layers include the hetero-cyclic compound.

The organic material layer of the organic light emitting device of the present specification may have a single layer structure, or a multilayered structure in which two or more layers of the organic material layers are laminated. For example, the organic light emitting device of the present invention may have a structure including a hole injection layer, a hole transport layer, a light emitting layer, an electron transport layer, an electron injection layer, and the like as the organic material layer.

However, the structure of the organic light emitting device is not limited thereto, but may include a smaller number of organic layers.

In the exemplary embodiment of the present specification, the organic material layer includes the hole injection layer or the hole transport layer, and the hole injection layer or the hole transport layer includes the hetero-cyclic compound.

In another exemplary embodiment, the organic material layer includes the light emitting layer, and the light emitting layer includes the hetero-cyclic compound as a host of the light emitting layer.

In the exemplary embodiment of the present specification, the organic material layer includes the electron transport layer, the electron injection layer, or a layer simultaneously transporting and injecting electrons, and the electron transport layer or the electron injection layer includes the hetero-cyclic compound.

In one exemplary embodiment of the present specification, there is provided an organic light emitting device including: a first electrode; a second electrode provided to face the first electrode; a light emitting layer provided between the first electrode and the second electrode; and two or more organic material layers provided between the light emitting layer and the first electrode or between the light emitting layer and the second electrode, in which at least one of the two or more organic material layers includes the hetero-cyclic compound. In one exemplary embodiment, the two or more organic material layers may include two or more selected from the group consisting of an electron transport layer, an electron injection layer, a layer simultaneously transporting and injecting electrons, and a hole blocking layer.

In the exemplary embodiment of the present specification, the organic material layer includes two or more electron transport layers, and at least one of the two or more electron transport layers includes the hetero-cyclic compound. Specifically, in the exemplary embodiment of the present specification, the hetero-cyclic compound may be included in one layer of the two or more electron transport layers, and may be included in each of the two or more electron transport layers.

Further, in the exemplary embodiment of the present specification, in the case where the hetero-cyclic compound is included in each of the two or more electron transport layers, materials other than the hetero-cyclic compound may be the same as or different from each other.

In the exemplary embodiment of the present specification, the electron transport layer, the electron injection layer, or the layer simultaneously transporting and injecting the electrons includes only the hetero-cyclic compound.

In the exemplary embodiment of the present specification, the organic material layer further includes the hole injection layer or the hole transport layer including a compound including an arylamino group, a carbazole group, or a benzocarbazole group in addition to the organic material layer including the hetero-cyclic compound.

In the exemplary embodiment of the present specification, the organic material layer including the hetero-cyclic compound includes the hetero-cyclic compound as a host, and includes another organic compound, a metal, or a metal compound as a dopant.

In the exemplary embodiment of the present specification, the organic light emitting device further includes one layer or two or more layers selected from the group consisting of the hole injection layer, the hole transport layer, the electron transport layer, the electron injection layer, the electron blocking layer, and the hole blocking layer.

In another exemplary embodiment, the organic light emitting device may be an organic light emitting device having a structure (normal type) where an anode, one or more organic material layers, and a cathode are sequentially laminated on a substrate.

In another exemplary embodiment, the organic light emitting device may be an organic light emitting device having an inverted direction structure (inverted type) where a cathode, one or more organic material layers, and an anode are sequentially laminated on a substrate.

For example, the structure of the organic light emitting device according to the exemplary embodiment of the present specification is illustrated in FIGS. 1 and 2.

FIG. 1 illustrates a structure of an organic light emitting device where a substrate 1, an anode 2, a light emitting layer 3, and a cathode 4 are sequentially laminated. In the aforementioned structure, the hetero-cyclic compound may be included in the light emitting layer 3.

FIG. 2 illustrates a structure of an organic light emitting device where the substrate 1, the anode 2, a hole injection layer 5, a hole transport layer 6, the light emitting layer 3, an electron transport layer 7, and the cathode 4 are sequentially laminated. In the aforementioned structure, the hetero-cyclic compound may be included in one or more layers of the hole injection layer 5, the hole transport layer 6, the light emitting layer 3, and the electron transport layer 7.

In the aforementioned structure, the compound may be included in one or more layers of the hole injection layer, the hole transport layer, the light emitting layer, and the electron transport layer.

The organic light emitting device of the present specification may be manufactured by materials and methods known in the art, except that one or more layers of the organic material layers include the compound of the present specification, that is, the hetero-cyclic compound.

In the case where the organic light emitting device includes a plurality of organic material layers, the organic material layers may be formed of the same material or different materials.

The organic light emitting device of the present specification may be manufactured by materials and methods known in the art, except that one or more layers of the organic material layers include the hetero-cyclic compound, that is, the compound represented by Chemical Formula 1.

For example, the organic light emitting device of the present specification may be manufactured by sequentially laminating the first electrode, the organic material layer, and the second electrode on the substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming the organic material layers including the hole injection layer, the hole transport layer, the light emitting layer, and the electron transport layer thereon, and then depositing a material that can be used as the cathode thereon. In addition to the aforementioned method, the organic light emitting device may be manufactured by sequentially depositing a cathode material, the organic material layer, and an anode material on the substrate.

Further, the compound of Chemical Formula 1 may be formed as the organic material layer by a solution coating method as well as a vacuum deposition method when the organic light emitting device is manufactured. Herein, the solution coating method means spin coating, dip coating, doctor blading, inkjet printing, screen printing, a spray method, roll coating, or the like, but is not limited thereto.

In addition to the aforementioned method, the organic light emitting device may be manufactured by sequentially depositing the cathode material, the organic material layer, and the anode material on the substrate (International Patent Application Laid-Open No. WO 2003/012890). However, the manufacturing method is not limited thereto.

In the exemplary embodiment of the present specification, the first electrode is the anode, and the second electrode is the cathode.

In another exemplary embodiment, the first electrode is the cathode, and the second electrode is the anode.

It is preferable that the anode material be, in general, a material having a large work function so as to smoothly inject holes into the organic material layer.

Specific examples of the anode material that may be used in the present invention include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as $ZnO:Al$ or $SnO_2:Sb$; conductive polymers such as poly(3-methylthiophene), poly[3,4-(ethylene-1,2-dioxy)thiophene] (PEDOT), polypyrrole, and polyaniline, and the like, but are not limited thereto.

It is preferable that the cathode material be, in general, a material having a small work function so as to easily inject electrons into the organic material layer.

Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or LiO$_2$/Al, and the like, but are not limited thereto.

The hole injection material is used for a layer injecting the holes from the electrode, and it is preferable that the hole injection material be a compound which has an ability of transporting the holes to have a hole injection effect from the anode and an excellent hole injection effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material be between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline, a polythiophene-based conductive polymer, and the like, but are not limited thereto.

The hole transport layer is a layer receiving the holes from the hole injection layer and transporting the holes to the light emitting layer, the hole transport material is a material capable of receiving the holes from the anode or the hole injection layer and transporting the holes to the light emitting layer, and a material having large mobility to the holes is suitable as the hole transport material. Specific examples thereof include an arylamine-based organic material, a conductive polymer, a block copolymer in which a conjugate portion and a non-conjugate portion are present together, and the like, but are not limited thereto.

The light emitting material is a material that can receive the holes and the electrons from the hole transport layer and the electron transport layer, respectively, and bond the holes and the electrons to emit light in a visible ray region, and is preferably a material having good quantum efficiency to fluorescence or phosphorescence. Specific examples thereof include a 8-hydroxy-quinoline aluminum complex (Alq$_3$); a carbazole-based compound; a dimerized styryl compound; BAlq; a 10-hydroxybenzoquinoline-metal compound; benzoxazole, benzthiazole, and benzimidazole-based compounds; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensation aromatic cycle derivative, a hetero-cycle-containing compound, or the like. Specific examples of the compensation aromatic cycle derivative include an anthracene derivative, a pyrene derivative, a naphthalene derivative, a pentacene derivative, a phenanthrene compound, a fluoranthene compound, and the like, and specific examples of the hetero-cycle-containing compound include a carbazole derivative, a dibenzofuran derivative, a ladder-type furan compound, a pyrimidine derivative, and the like, but the examples are not limited thereto.

Examples of the dopant material include an organic compound, a metal, or a metal compound.

Examples of the organic compound as the dopant material include an aromatic amine derivative, a styrylamine compound, a boron complex, a fluoranthene compound, and the like. Specifically, the aromatic amine derivative is a compensation aromatic cycle derivative having a substituted or unsubstituted arylamino group, examples thereof include pyrene, anthracene, chrysene, and periflanthene having the arylamino group, and the like, the styrylamine compound is a compound where at least one arylvinyl group is substituted in substituted or unsubstituted arylamine, and in the styrylamine compound, one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetraamine, and the like, but are not limited thereto. Further, a general metal or metal compound may be used as the metal or the metal compound, and specifically, a metal complex may be used. Further, examples of the metal complex include an iridium complex, a platinum complex, and the like, but are not limited thereto.

The electron transport material is used for a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable as the electron transport material. Specific examples thereof include an 8-hydroxyquinoline Al complex; a complex including Alq$_3$; an organic radical compound; a hydroxyflavone-metal complex, and the like, but are not limited thereto. The electron transport layer may be used together with a predetermined desired cathode material as used according to a known technology. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injection effect from the cathode, and an excellent electron injection effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris (2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present specification may be divided into a top emission type, a bottom emission type, or a both-sided emission type according to the used material.

In the exemplary embodiment of the present specification, the hetero-cyclic compound may be included in an organic solar cell or an organic transistor in addition to the organic light emitting device.

Manufacturing of the hetero-cyclic compound represented by Chemical Formula 1 and the organic light emitting device including the same will be described in detail in the following Examples. However, the following Examples are set forth to illustrate the present specification, but the scope of the present specification is not limited thereto.

EXAMPLE

Hereinafter, the present invention will be described in more detail through Preparation Examples and Experimental Examples, but the scope of the present invention is not limited by the following Preparation Examples and Experimental Examples.

Preparation Example

Preparation Example 1

Preparation of the Following Compound 1-1

1) Compound Synthesis of the Following Compound 1-A

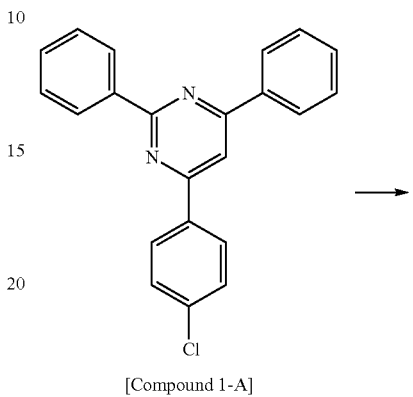

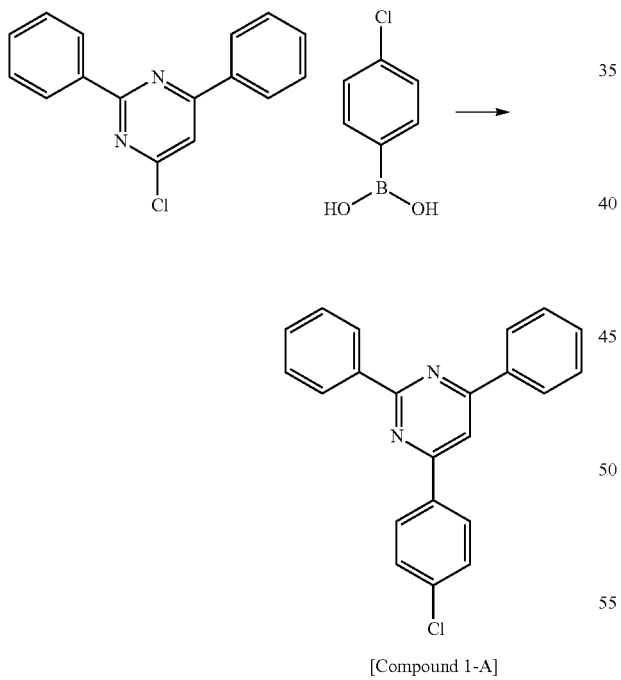

[Compound 1-A]

After the compound of 4-chloro-2,6-diphenylpyrimidine (37.3 g, 0.14 mol) and 4-chlorophenylboronic acid (23.8 g, 0.15 mol) were completely dissolved in 150 ml of tetrahydrofuran under the nitrogen atmosphere, 2M potassium carbonate aqueous solution (80 ml) was added, and tetrakis-(triphenylphosphine)palladium (3.2 g, 2.7 mmol) was put, followed by heating and agitation for 5 hours. The temperature was reduced to normal temperature, the water layer was removed, drying was performed by anhydrous magnesium sulfate, pressure-reduction concentration was performed, and column treatment at a tetrahydrofuran and hexane ratio of 1:6 was performed to prepare compound 1-A (34 g, yield: 71%).

MS [M+H]$^+$=343

2) Compound Synthesis of the Following Compound 1-B

[Compound 1-A]

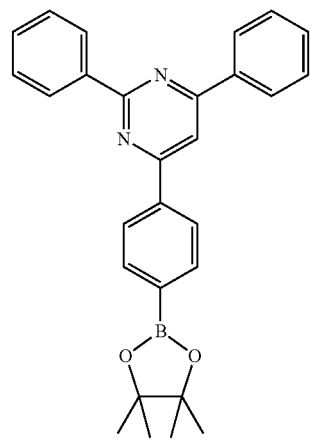

[Compound 1-B]

Compound 1-A (34.9 g, 98.9 mmol), bis(pinacolato)diboron (27.6 g, 108 mmol), and potassium acetate (29.1 g, 296 mmol) were mixed under the nitrogen atmosphere, added to 100 ml of dioxane, and heated while being agitated. Bis(dibenzylidyneacetone)palladium (1.7 g, 2.94 mmol) and tricyclohexylphosphine (1.6 g, 5.9 mmol) were put in the reflux state, and heated and agitated for 10 hours. After the reaction was finished, the temperature was reduced to normal temperature, followed by filtering. The filtrate was poured in water, extraction was performed by chloroform, and the organic layer was dried by anhydrous magnesium sulfate. After performing pressure-reduction distillation, recrystallization was performed by ethanol to prepare compound 1-B (35 g, yield: 81%).

MS [M+H]$^+$=435

3) Synthesis of the Following Compound 1-1

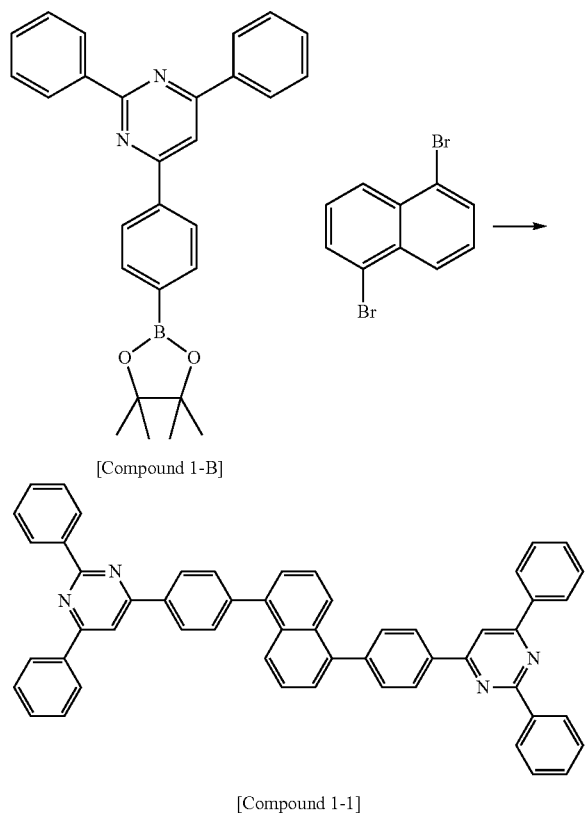

[Compound 1-B]

[Compound 1-1]

After compound 1-B (16.4 g, 37.7 mmol) and 1,5-dibromonaphthalene (5.1 g, 17.9 mmol) were completely dissolved in tetrahydrofuran (50 ml), 2M potassium carbonate aqueous solution (30 ml) was added, and tetrakistriphenylphosphinopalladium (400 mg, 0.34 mmol) was put, and heated and agitated for 2 hours. The temperature was reduced to normal temperature, the reaction was finished, and the potassium carbonate solution was removed to filter the white solid. The filtered white solid was washed once with each of tetrahydrofuran and ethanol to prepare compound 1-1 (12.0 g, yield 90%).

MS [M+H]$^+$=741

Preparation Example 2

Preparation of Compound 1-3

1) Synthesis of the Following Compound 2-A

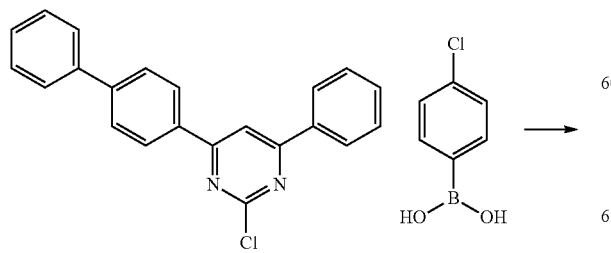

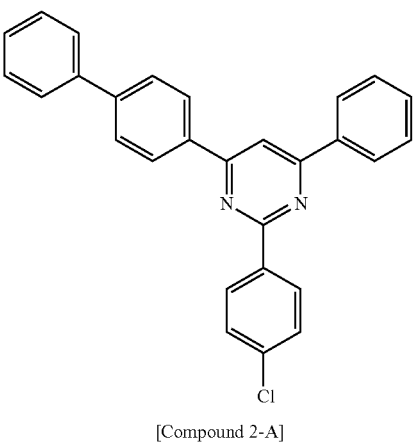

[Compound 2-A]

After the compound of 4-([1,1'-biphenyl]-4-yl)-2-chloro-6-phenylpyrimidine (48.0 g, 0.14 mol) and 4-chlorophenylboronic acid (23.8 g, 0.15 mol) were completely dissolved in 150 ml of tetrahydrofuran under the nitrogen atmosphere, 2M potassium carbonate aqueous solution (80 ml) was added, and tetrakis-(triphenylphosphine)palladium (3.2 g, 2.7 mmol) was put, followed by heating and agitation for 5 hours. The temperature was reduced to normal temperature, the water layer was removed, drying was performed by anhydrous magnesium sulfate, pressure-reduction concentration was performed, and column treatment at a tetrahydrofuran and hexane ratio of 1:6 was performed to prepare compound 2-A (42 g, yield: 71%).

MS [M+H]$^+$=419

2) Compound Synthesis of the Following Compound 2-B

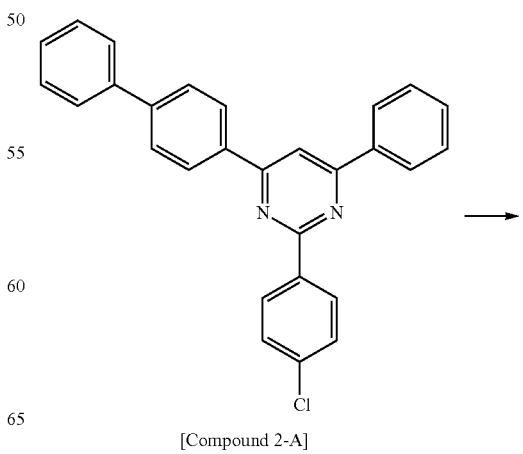

[Compound 2-A]

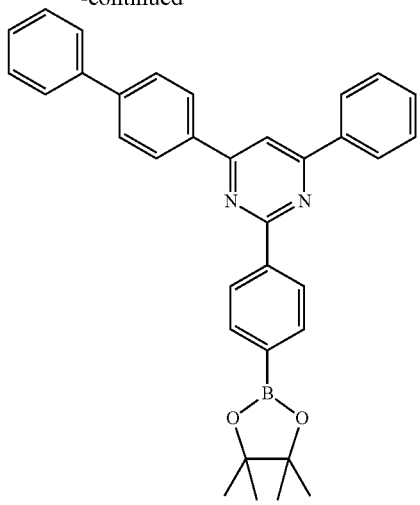

[Compound 2-B]

Compound 2-A (41.4 g, 98.9 mmol), bis(pinacolato)diboron (27.6 g, 108 mmol), and potassium acetate (29.1 g, 296 mmol) were mixed under the nitrogen atmosphere, added to 100 ml of dioxane, and heated while being agitated. Bis(dibenzylidyneacetone)palladium (1.7 g, 2.94 mmol) and tricyclohexylphosphine (1.6 g, 5.9 mmol) were put in the reflux state, and heated and agitated for 10 hours. After the reaction was finished, the temperature was reduced to normal temperature, followed by filtering.

The filtrate was poured in water, extraction was performed by chloroform, and the organic layer was dried by anhydrous magnesium sulfate. After performing pressure-reduction distillation, recrystallization was performed by ethanol to prepare compound 2-B (40.9 g, yield: 81%).

MS [M+H]+=511

3) Synthesis of the Following Compound 1-3

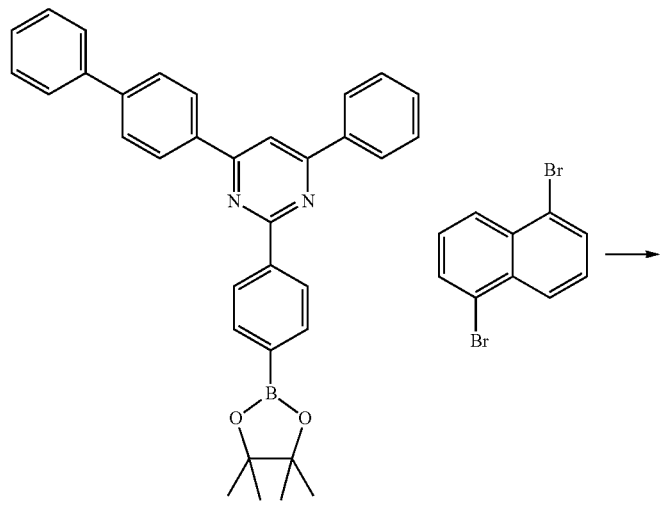

[Compound 2-B]

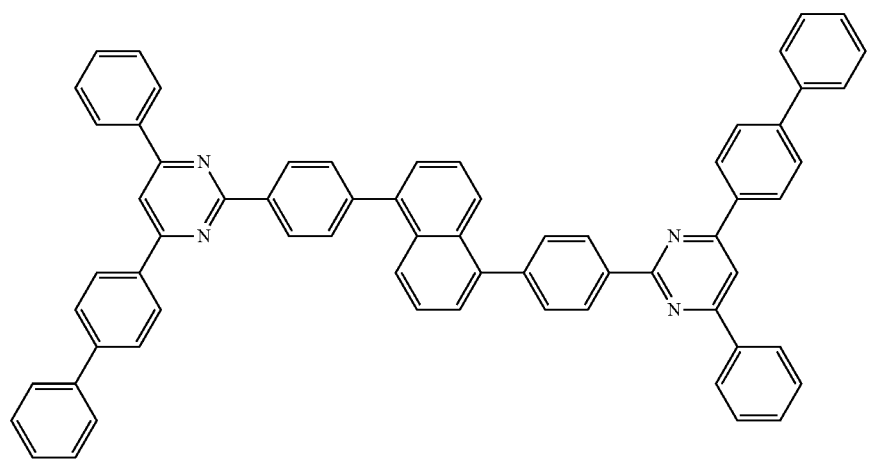

[Compound 1-3]

Compound 1-3 was prepared by the same method as the method of preparing compound 1-1, except that compound 2-B was used instead of compound 1-B.
MS [M+H]+=893

Preparation Example 3

Preparation of Compound 1-4

1) Synthesis of the Following Compound 3-A

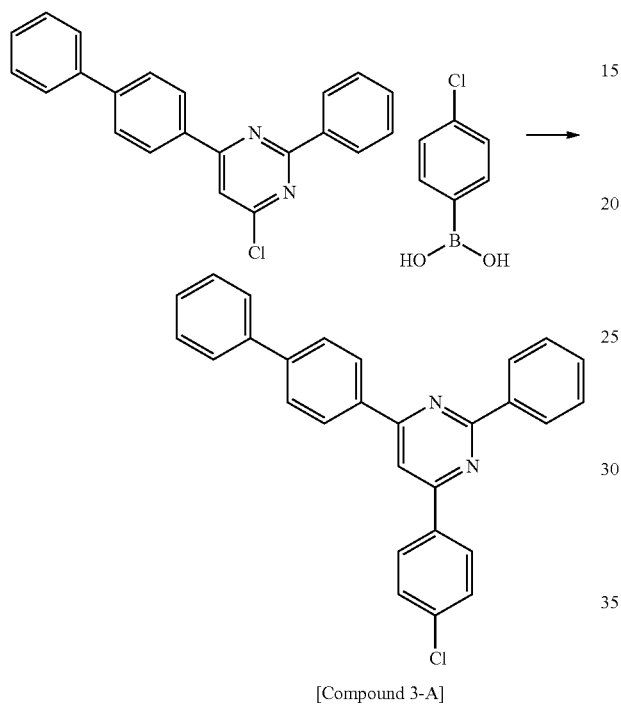

[Compound 3-A]

Compound 3-A was prepared by the same method as the method of preparing compound 1-A, except that 4-([1,1'-biphenyl]-4-yl)-6-chloro-2-phenylpyrimidine was used instead of the compound of 4-chloro-2,6-diphenylpyrimidine.
MS [M+H]+=419

2) Synthesis of the Following Compound 3-B

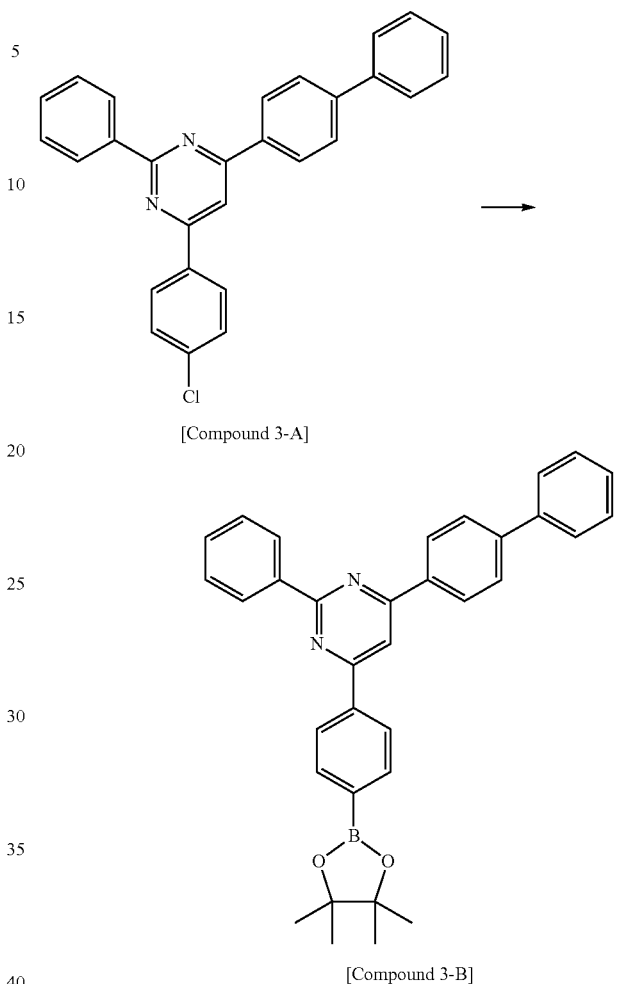

[Compound 3-B]

Compound 3-B was prepared by the same method as the method of preparing compound 1-B, except that compound 3-A was used instead of compound 1-A.
MS [M+H]+=511

3) Synthesis of the Following Compound 1-4

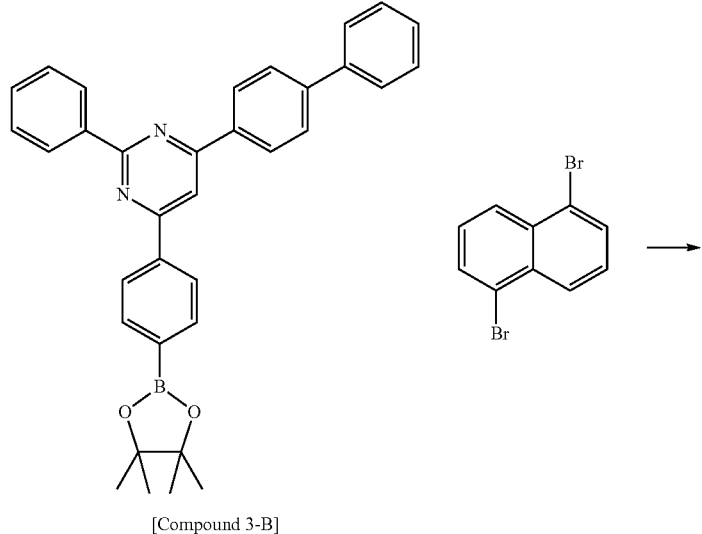

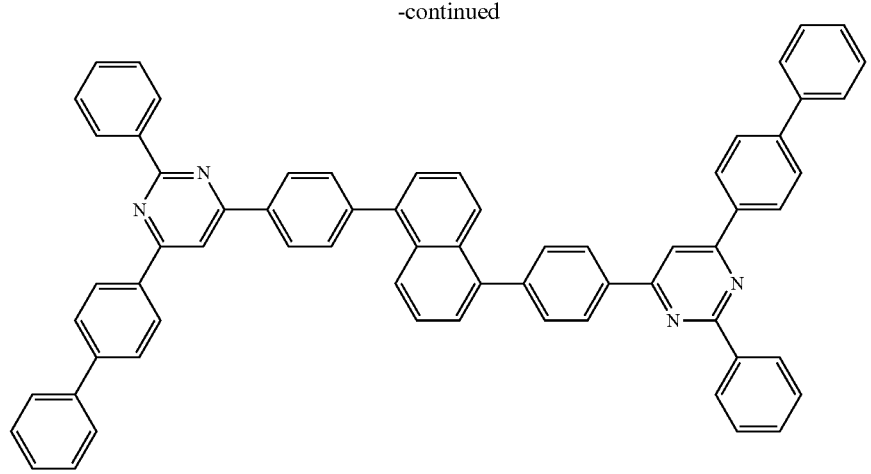

[Compound 1-4]

Compound 1-4 was prepared by the same method as the method of preparing compound 1-1, except that compound 3-B was used instead of compound 1-B.

MS [M+H]+=893

Preparation Example 4

Preparation of Compound 1-5

1) Synthesis of the Following Compound 4-A

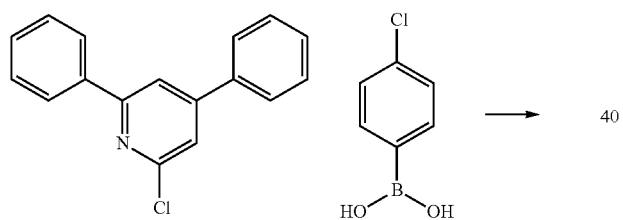

[Compound 4-A]

Compound 4-A was prepared by the same method as the method of preparing compound 1-A, except that 2-chloro-4,6-diphenylpyridine was used instead of the compound of 4-chloro-2,6-diphenylpyrimidine.

MS [M+H]+=342

2) Synthesis of the Following Compound 4-B

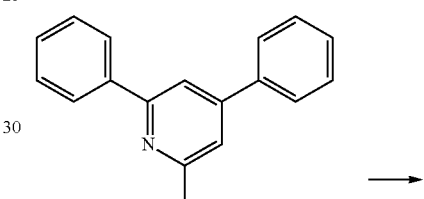

[Compound 4-A]

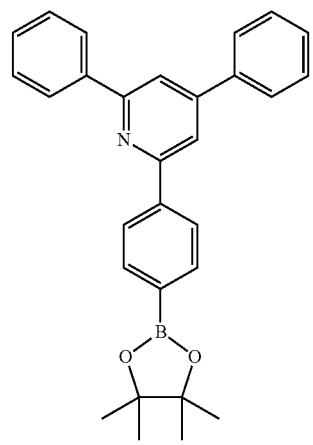

[Compound 4-B]

Compound 4-B was prepared by the same method as the method of preparing compound 1-B, except that compound 4-A was used instead of compound 1-A.

MS [M+H]$^+$=434

3) Synthesis of the Following Compound 1-5

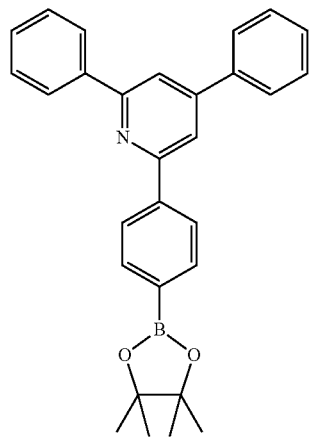

[Compound 4-B]

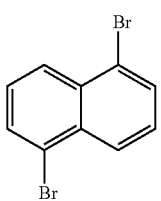

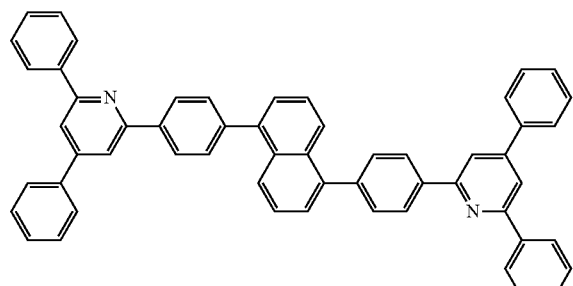

[Compound 1-5]

Compound 1-5 was prepared by the same method as the method of preparing compound 1-1, except that compound 4-B was used instead of compound 1-B.

MS [M+H]$^+$=739

Preparation Example 5

Preparation of Compound 1-6

1) Synthesis of the Following Compound 5-A

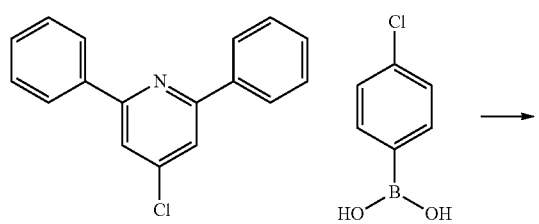

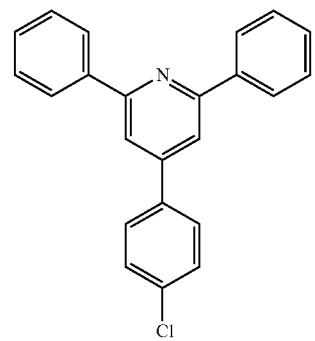

[Compound 5-A]

Compound 5-A was prepared by the same method as the method of preparing compound 1-A, except that 4-(4-chlorophenyl)-2,6-diphenylperidine was used instead of the compound of 4-chloro-2,6-diphenylpyrimidine.

MS [M+H]+=342

2) Synthesis of the Following Compound 5-B

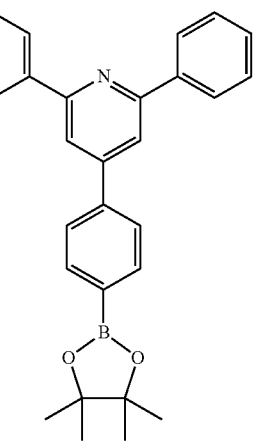

[Compound 5-A]

[Compound 5-B]

Compound 5-B was prepared by the same method as the method of preparing compound 1-B, except that compound 5-A was used instead of compound 1-A.

MS [M+H]+=434

3) Synthesis of the Following Compound 1-6

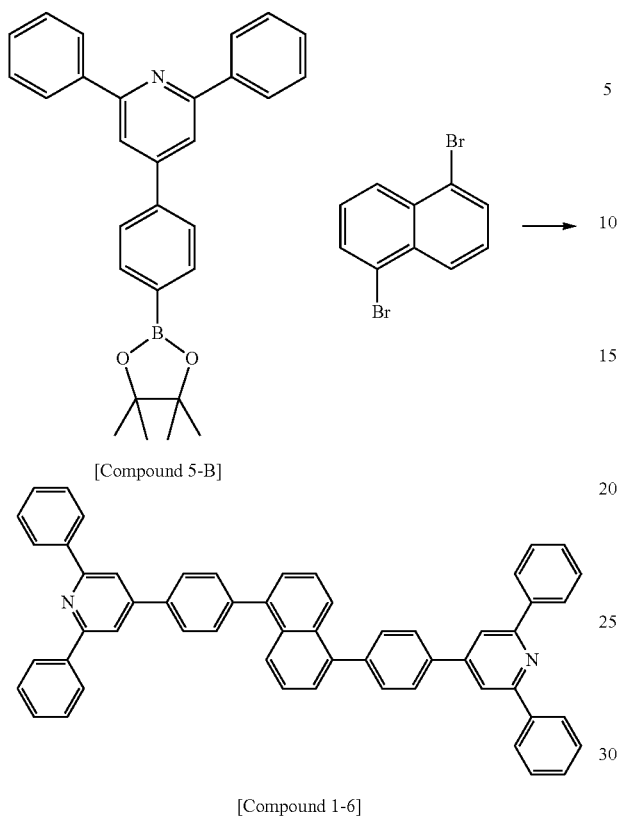

[Compound 5-B]

[Compound 1-6]

Compound 1-6 was prepared by the same method as the method of preparing compound 1-1, except that compound 5-B was used instead of compound 1-B.
MS [M+H]$^+$=739

Preparation Example 6

Preparation of Compound 1-15

1) Synthesis of the Following Compound 6-A

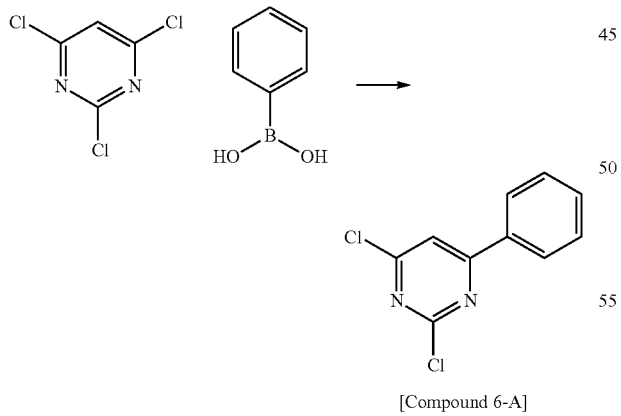

[Compound 6-A]

After the compounds of 2,4,6-trichloropyrimidine (40.0 g, 0.218 mol) and phenylboronic acid (26.6 g, 0.218 mol) were completely dissolved in 250 ml of tetrahydrofuran under the nitrogen atmosphere, 2M potassium carbonate aqueous solution (125 ml) was added, and tetrakis-(triphenylphosphine) palladium (7.6 g, 6.5 mmol) was put, followed by heating and agitation for 5 hours. The temperature was reduced to normal temperature, the water layer was removed, drying was performed by anhydrous magnesium sulfate, pressure-reduction concentration was performed, and column treatment at a tetrahydrofuran and hexane ratio of 1:3 was performed to prepare compound 6-A (40 g, yield: 82%).
MS [M+H]$^+$=224

2) Synthesis of the Following Compound 6-B

[Compound 6-A]

[Compound 6-B]

Compound 6-B was prepared by the same method as the method of preparing compound 6-A, except that the (9,9-dimethyl-9H-fluorene-2-yl)boronic acid was used instead of the compound of the phenylboronic acid.
MS [M+H]$^+$=382

3) Synthesis of the Following Compound 6-C

[Compound 6-B]

[Compound 6-C]

Compound 6-C was prepared by the same method as the method of preparing compound 1-A, except that compound 6-B was used instead of the compound of 4-chloro-2,6-diphenylpyrimidine.

MS [M+H]$^+$=458

4) Synthesis of the Following Compound 6-D

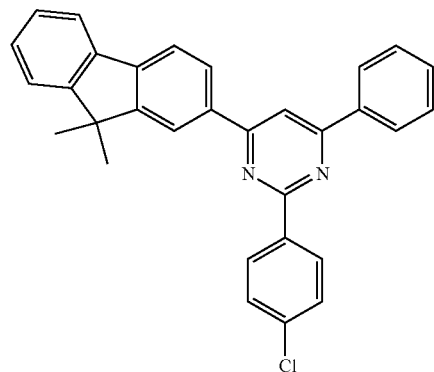

[Compound 6-C]

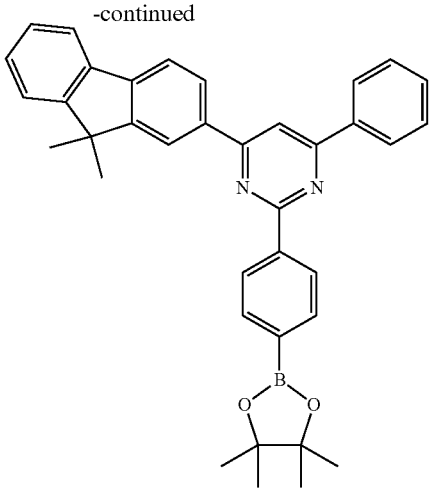

[Compound 6-D]

Compound 6-D was prepared by the same method as the method of preparing compound 1-B, except that compound 6-C was used instead of compound 1-A.

MS [M+H]+=550

5) Synthesis of the Following Compound 1-15

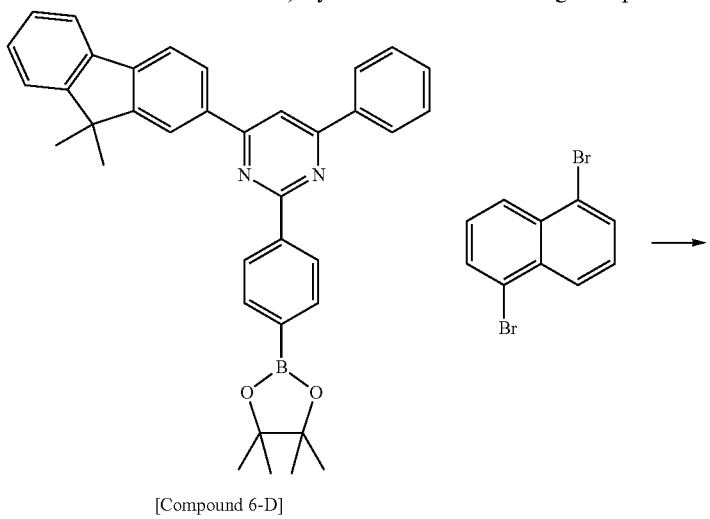

[Compound 6-D]

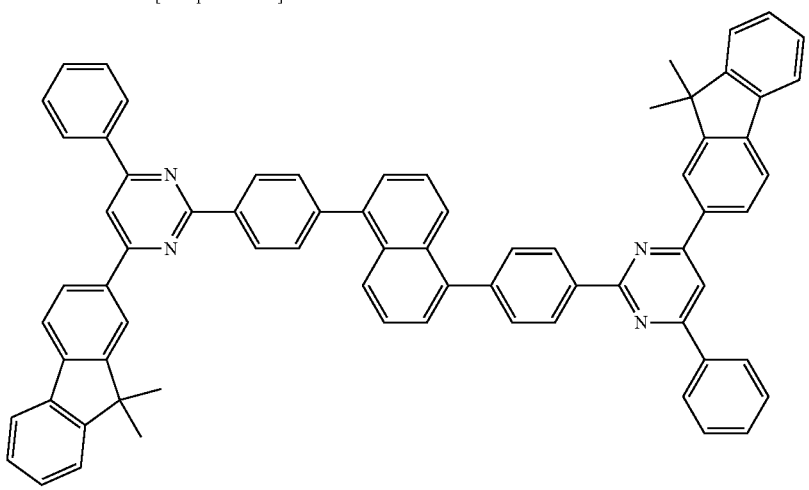

[Compound 1-15]

Compound 1-15 was prepared by the same method as the method of preparing compound 1-1, except that compound 6-D was used instead of compound 1-B.

MS [M+H]+=972

Preparation Example 7

Preparation of Compound 1-24

1) Synthesis of the Following Compound 7-A

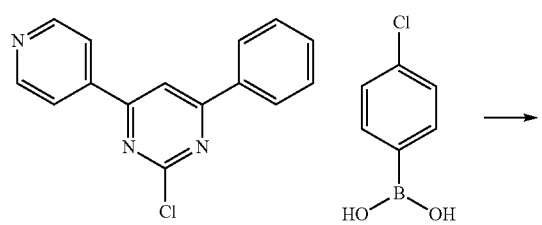

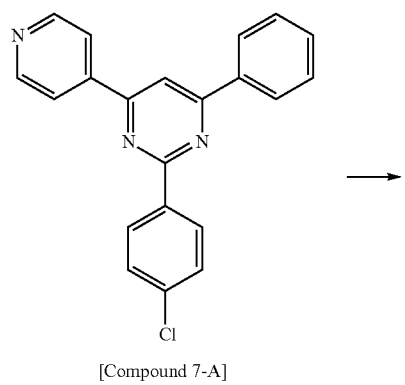

[Compound 7-A]

Compound 7-A was prepared by the same method as the method of preparing compound 1-A, except that 2-chloro-4-phenyl-6-(pyridine-4-yl)pyrimidine was used instead of the compound of 4-chloro-2,6-diphenylpyrimidine.

MS [M+H]$^+$=343

2) Synthesis of the Following Compound 7-B

[Compound 7-A]

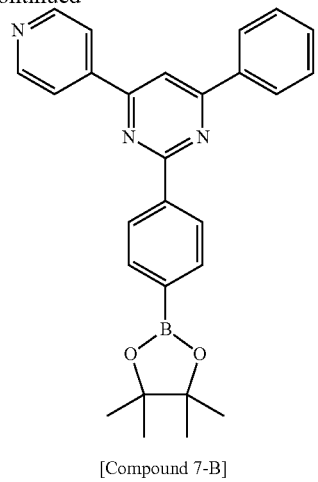

[Compound 7-B]

Compound 7-B was prepared by the same method as the method of preparing compound 1-B, except that compound 7-A was used instead of compound 1-A.

MS [M+H]$^+$=435

3) Synthesis of the Following Compound 1-24

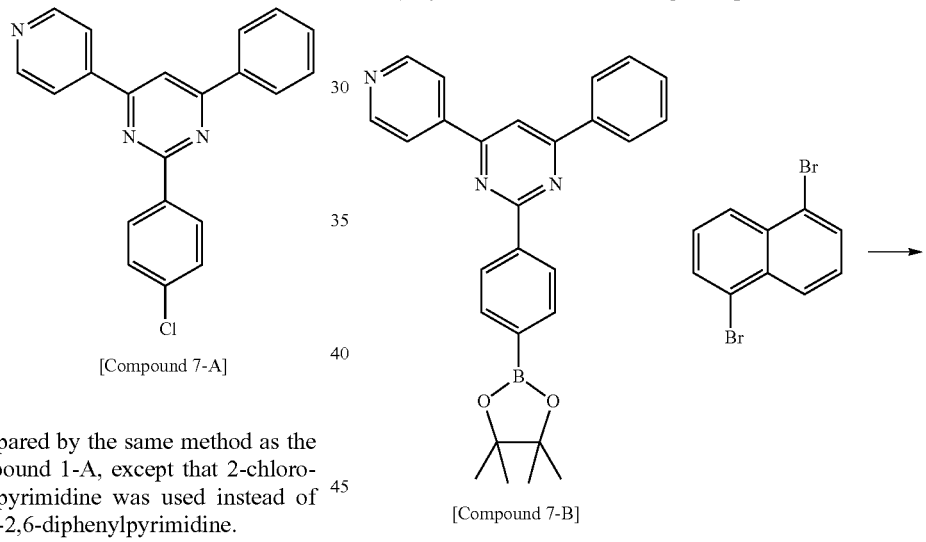

[Compound 7-B]

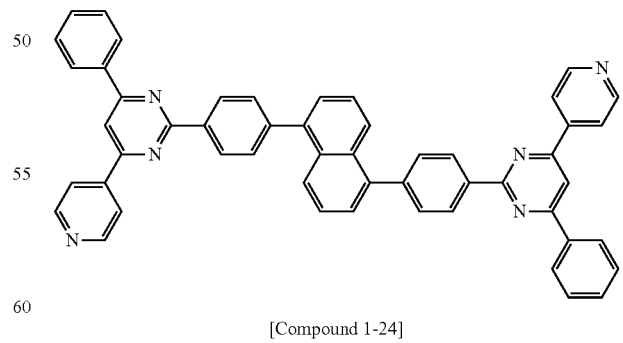

[Compound 1-24]

Compound 1-24 was prepared by the same method as the method of preparing compound 1-1, except that compound 7-B was used instead of compound 1-B.

MS [M+H]$^+$=742

Preparation Example 8

Preparation of Compound 1-47

1) Synthesis of the Following Compound 8-A

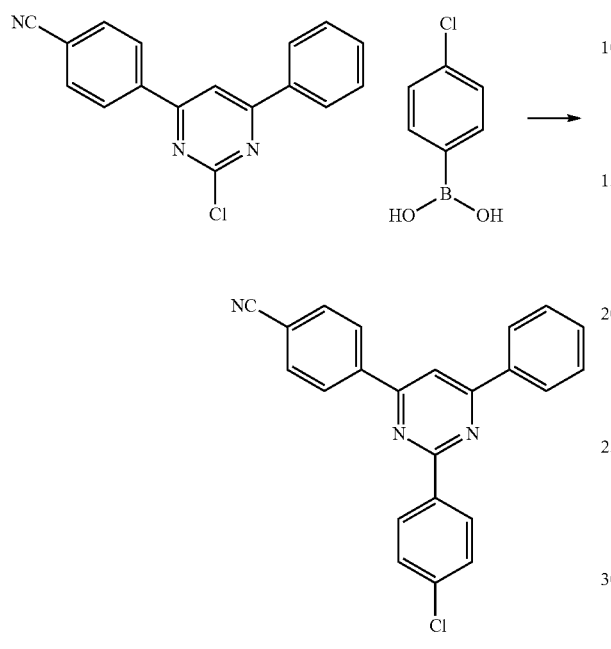

[Compound 8-A]

Compound 8-A was prepared by the same method as the method of preparing compound 1-A, except that 4-(2-chloro-6-phenylpyrimidine-4-yl)benzonitrile was used instead of the compound of 4-chloro-2,6-diphenylpyrimidine.

MS [M+H]+=367

2) Synthesis of the Following Compound 8-B

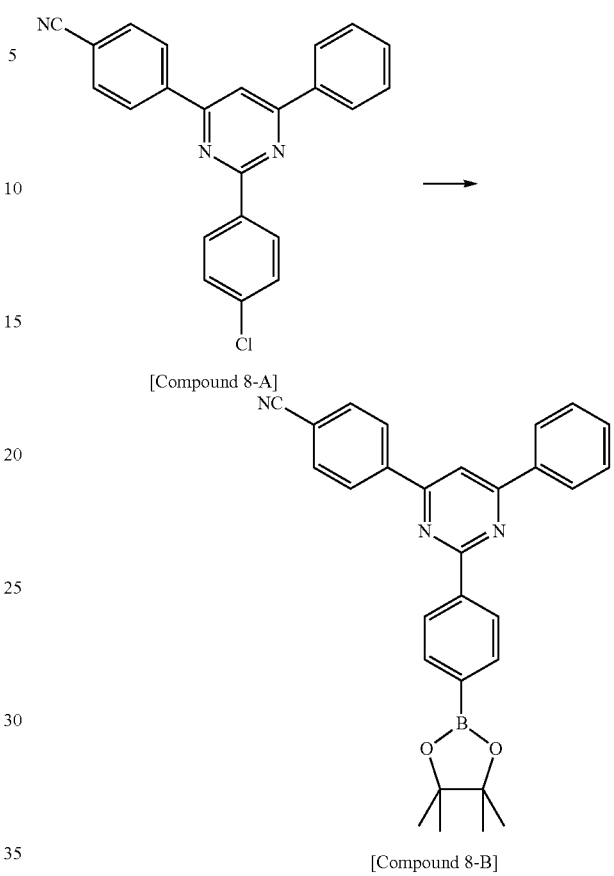

[Compound 8-A]

[Compound 8-B]

Compound 8-B was prepared by the same method as the method of preparing compound 1-B, except that compound 8-A was used instead of compound 1-A.

MS [M+H]$^+$=459

3) Synthesis of the Following Compound 1-47

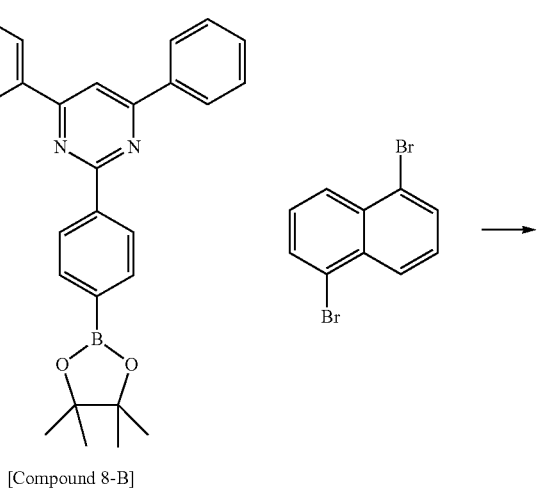

[Compound 8-B]

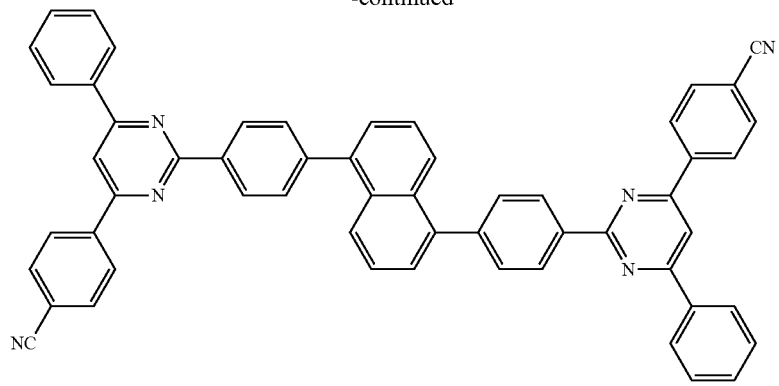

[Compound 1-47]

Compound 1-47 was prepared by the same method as the method of preparing compound 1-1, except that compound 8-B was used instead of compound 1-B.

MS [M+H]$^+$=790

Preparation Example 9

Preparation of Compound 2-1

1) Synthesis of the Following Compound 2-1

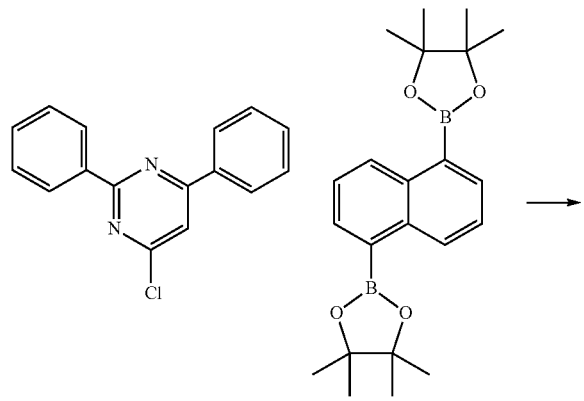

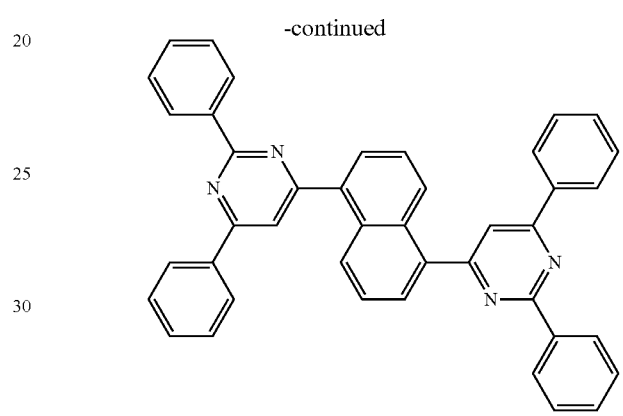

[Compound 2-1]

After the compound of 4-chloro-2,6-diphenylpyrimidine (10.1 g, 37.7 mmol) and 1,5-bis(4,4,5,5-tetramethyl-1,3,2-dioctaborolane-2-yl)naphthalene (6.8 g, 17.9 mmol) were completely dissolved in tetrahydrofuran (50 ml), 2M potassium carbonate aqueous solution (30 ml) was added, and tetrakistriphenyl-phosphinopalladium (400 mg, 0.34 mmol) was put, followed by heating and agitation for 2 hours. The temperature was reduced to normal temperature, the reaction was finished, and the potassium carbonate solution was removed to filter the white solid. The filtered white solid was washed once with each of tetrahydrofuran and ethanol to prepare compound 2-1 (9.5 g, yield 90%).

MS [M+H]+=589

Preparation Example 10

Preparation of Compound 2-3

1) Synthesis of the Following Compound 2-3

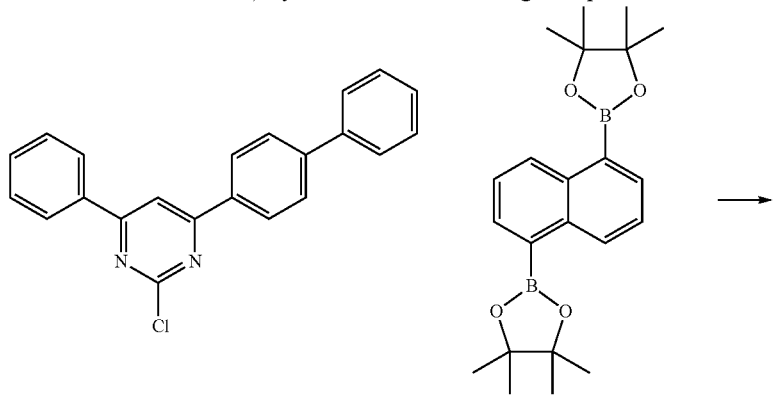

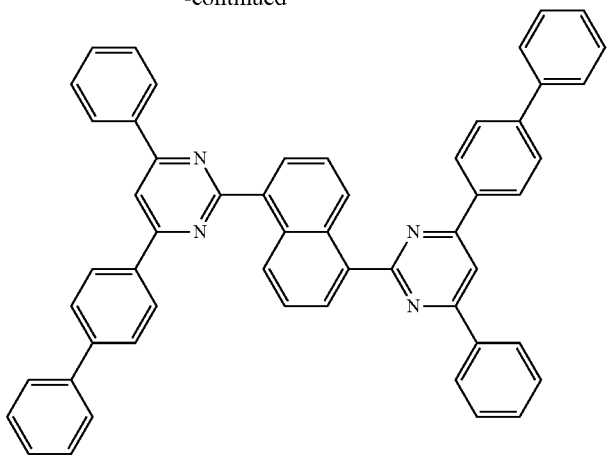

[Compound 2-3]

Compound 2-3 was prepared by the same method as the method of preparing compound 2-1, except that 4-([1,1'-biphenyl]-4-yl)-2-chloro-6-phenylpyrimidine was used instead of the compound of 4-chloro-2,6-diphenylpyrimidine.

MS [M+H]$^+$=741

Preparation Example 11

Preparation of Compound 2-4

1) Synthesis of the Following Compound 2-4

Compound 2-4 was prepared by the same method as the method of preparing compound 2-1, except that 4-([1,1'-biphenyl]-4-yl)-6-chloro-2-phenylpyrimidine was used instead of the compound of 4-chloro-2,6-diphenylpyrimidine.

MS [M+H]$^+$=741

Preparation Example 12

Preparation of Compound 2-5

1) Synthesis of the Following Compound 2-5

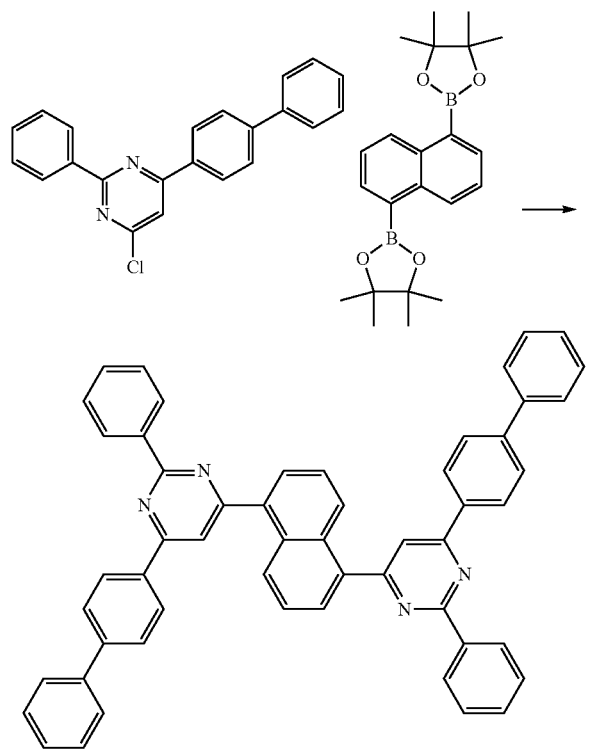

[Compound 2-4]

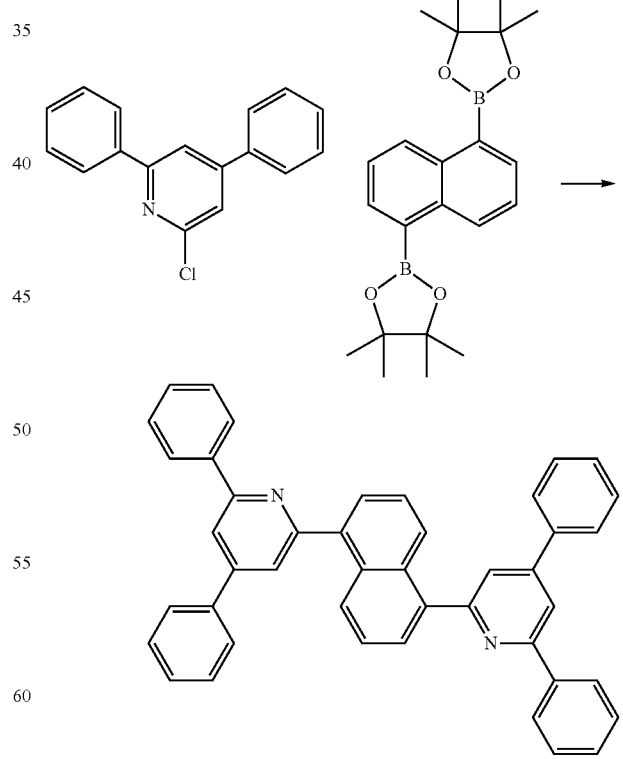

[Compound 2-5]

Compound 2-5 was prepared by the same method as the method of preparing compound 2-1, except that 2-chloro- 4,6-diphenylpyridine was used instead of the compound of 4-chloro-2,6-diphenylpyrimidine.

MS [M+H]+=587

Preparation Example 13

Preparation of Compound 2-15

1) Synthesis of the Following Compound 2-15

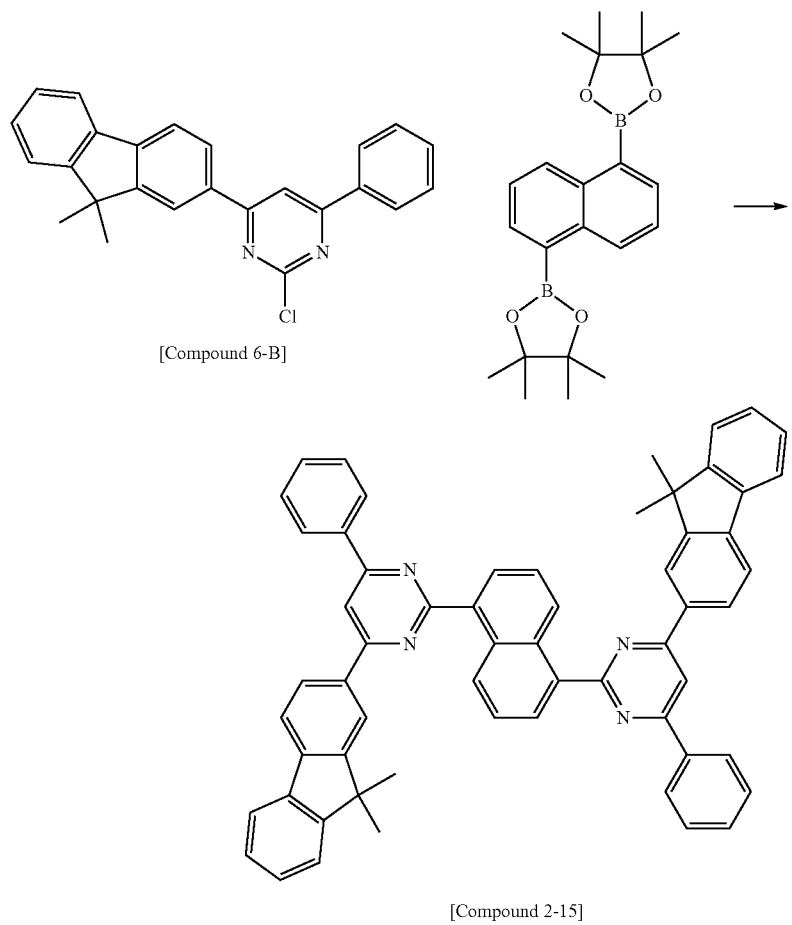

Compound 2-15 was prepared by the same method as the method of preparing compound 2-1, except that compound 6-B was used instead of the compound of 4-chloro-2,6-diphenylpyrimidine.

MS [M+H]+=820

Experimental Example 1

The glass substrate on which a thin film of ITO (indium tin oxide) was applied in a thickness of 1,000 Å was put into distilled water having the detergent dissolved therein and washed by the ultrasonic wave. In this case, the product manufactured by Fischer Co., was used as the detergent, and distilled water, which had been twice filtered by the filter manufactured by Millipore Co., was used as distilled water. The ITO was washed for 30 minutes, and washing with ultrasonic waves was then repeated twice for 10 minutes by using distilled water. After the washing with distilled water was finished, washing with ultrasonic waves was performed by solvents such as isopropyl alcohol, acetone, and methanol, and the ITO was dried and transported to the plasma washing machine. Further, the substrate was washed by using oxygen plasma for 5 minutes, and then transported to the vacuum deposition machine.

Hexanitrile hexaazatriphenylene (HAT) of the following Chemical Formula was thermally deposited in a thicknesses of 500 Å under the vacuum on the ITO transparent electrode thus prepared to form the hole injecting layer.

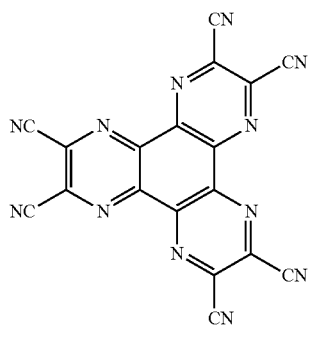

[HAT]

4-4'-bis[N-(1-naphthyl)-N-phenylamino]biphenyl (NPB) (400 Å) of the following compound that was the material transporting the holes was deposited under the vacuum on the hole injection layer to form the hole transport layer.

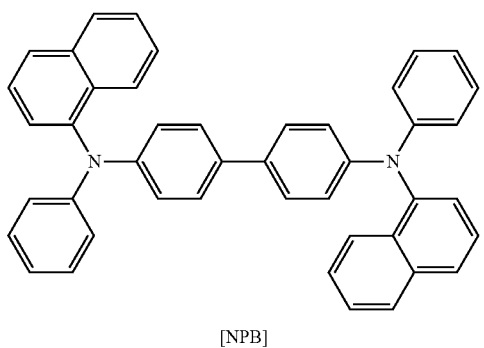

[NPB]

Subsequently, BH and BD shown below were deposited under the vacuum at a weight ratio of 25:1 on the hole transport layer to form the light emitting layer in a film thickness of 300 Å.

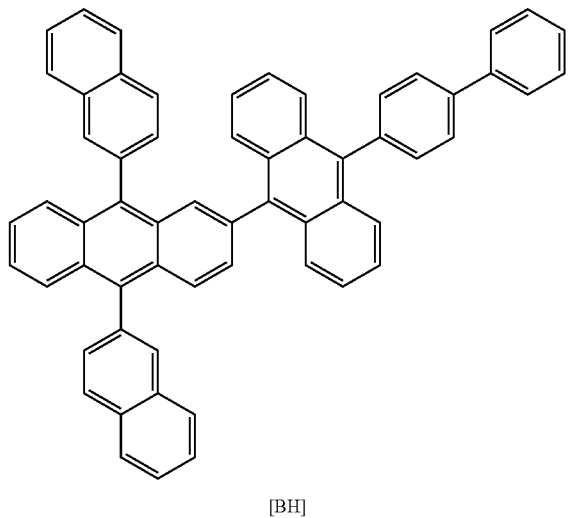

[BH]

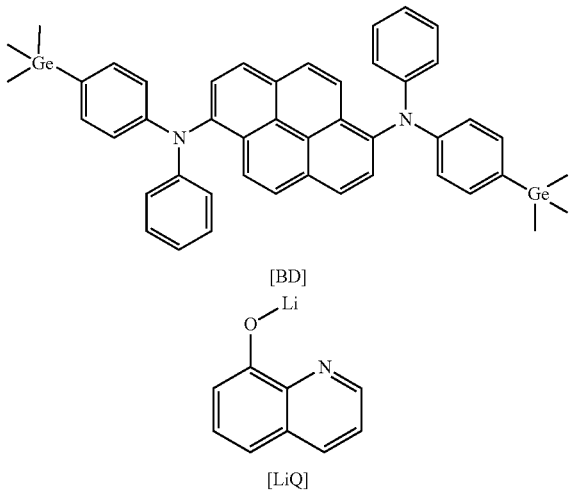

[BD]

[LiQ]

Compound 1-1 prepared in Preparation Example 1 and the compound of LiQ (lithium quinolate) were deposited under the vacuum at a weight ratio of 1:1 on the light emitting layer to form the electron injection and transport layer in a thickness of 300 Å. Lithium fluoride (LiF) in a thickness of 12 Å and aluminum in a thickness of 2,000 Å were subsequently deposited on the electron injection and transport layer to form the cathode.

In the aforementioned process, the deposition speed of the organic material was maintained at 0.4 to 0.7 Å/sec, the deposition speed of lithium fluoride of the cathode was maintained at 0.3 Å/sec, the deposition speed of aluminum was maintained at 2 Å/sec, and the degree of vacuum during deposition was maintained at $2\times10^{-7}$ to $5\times10^{-6}$ torr to manufacture the organic light emitting device.

Experimental Example 2

The organic light emitting device was manufactured by the same method as Experimental Example 1, except that compound 1-3 was used instead of compound 1-1 in Experimental Example 1.

Experimental Example 3

The organic light emitting device was manufactured by the same method as Experimental Example 1, except that compound 1-4 was used instead of compound 1-1 in Experimental Example 1.

Experimental Example 4

The organic light emitting device was manufactured by the same method as Experimental Example 1, except that compound 1-5 was used instead of compound 1-1 in Experimental Example 1.

Experimental Example 5

The organic light emitting device was manufactured by the same method as Experimental Example 1, except that compound 1-6 was used instead of compound 1-1 in Experimental Example 1.

Experimental Example 6

The organic light emitting device was manufactured by the same method as Experimental Example 1, except that compound 1-15 was used instead of compound 1-1 in Experimental Example 1.

Experimental Example 7

The organic light emitting device was manufactured by the same method as Experimental Example 1, except that compound 1-24 was used instead of compound 1-1 in Experimental Example 1.

Experimental Example 8

The organic light emitting device was manufactured by the same method as Experimental Example 1, except that compound 1-47 was used instead of compound 1-1 in Experimental Example 1.

Experimental Example 9

The organic light emitting device was manufactured by the same method as Experimental Example 1, except that compound 2-1 was used instead of compound 1-1 in Experimental Example 1.

Experimental Example 10

The organic light emitting device was manufactured by the same method as Experimental Example 1, except that compound 2-3 was used instead of compound 1-1 in Experimental Example 1.

Experimental Example 11

The organic light emitting device was manufactured by the same method as Experimental Example 1, except that compound 2-4 was used instead of compound 1-1 in Experimental Example 1.

Experimental Example 12

The organic light emitting device was manufactured by the same method as Experimental Example 1, except that compound 2-5 was used instead of compound 1-1 in Experimental Example 1.

Experimental Example 13

The organic light emitting device was manufactured by the same method as Experimental Example 1, except that compound 2-15 was used instead of compound 1-1 in Experimental Example 1.

Experimental Example 14

The organic light emitting device was manufactured by the same method as Experimental Example 1, except that compound 2-24 was used instead of compound 1-1 in Experimental Example 1.

Experimental Example 15

The organic light emitting device was manufactured by the same method as Experimental Example 1, except that compound 2-47 was used instead of compound 1-1 in Experimental Example 1.

Comparative Example 1

The organic light emitting device was manufactured by the same method as Experimental Example 1, except that the following compound of ET1 was used instead of compound 1-1 in Experimental Example 1.

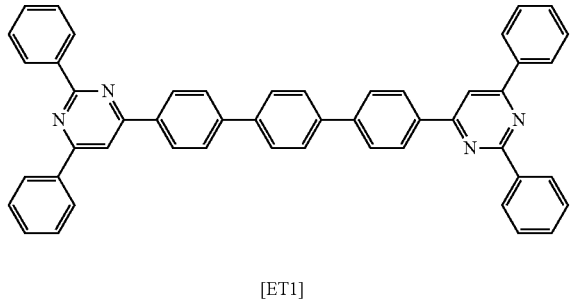 [SMILES: c1ccc(-c2cc(-c3ccc(-c4ccc(-c5ccc(-c6cc(-c7ccccc7)nc(-c7ccccc7)n6)cc5)cc4)cc3)nc(-c3ccccc3)n2)cc1]

[ET1]

Comparative Example 2

The organic light emitting device was manufactured by the same method as Experimental Example 1, except that the following compound of ET2 was used instead of compound 1-1 in Experimental Example 1.

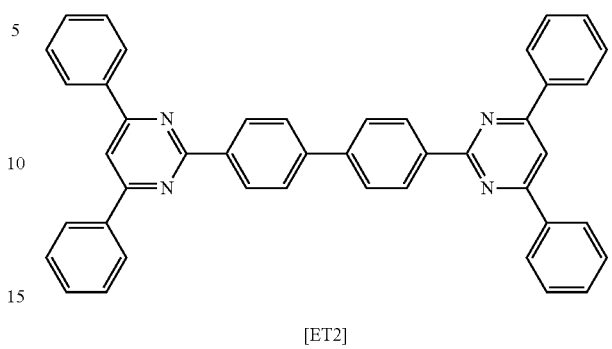

[ET2]

Comparative Example 3

The organic light emitting device was manufactured by the same method as Experimental Example 1, except that the following compound of ET3 was used instead of compound 1-1 in Experimental Example 1.

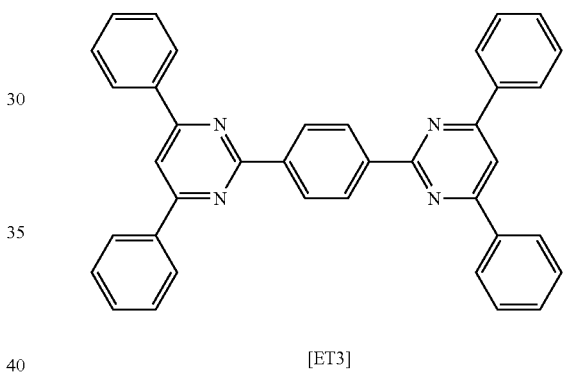

[ET3]

Comparative Example 4

The organic light emitting device was manufactured by the same method as Experimental Example 1, except that the following compound of ET4 was used instead of compound 1-1 in Experimental Example 1.

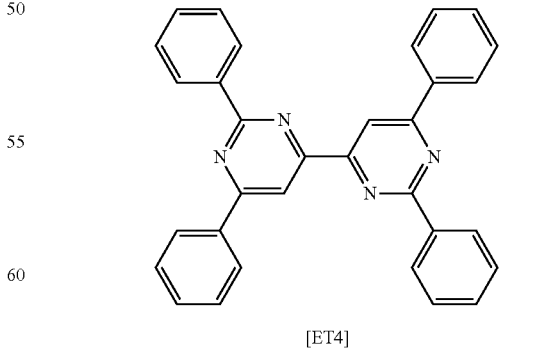

[ET4]

Properties of the organic light emitting devices manufactured in Experimental Examples 1 to 15 and Comparative Examples 1 to 4 are described in the following Table 1.

TABLE 1

| | Compound | Voltage (V@10 mA/cm$^2$) | Efficiency (cd/A@10 mA/cm$^2$) | Color coordinate (x, y) |
|---|---|---|---|---|
| Experimental Example 1 | Compound 1-1 | 3.98 | 4.91 | (0.138, 0.127) |
| Experimental Example 2 | Compound 1-3 | 3.75 | 5.15 | (0.139, 0.122) |
| Experimental Example 3 | Compound 1-4 | 3.86 | 5.04 | (0.138, 0.126) |
| Experimental Example 4 | Compound 1-5 | 3.85 | 4.72 | (0.138, 0.127) |
| Experimental Example 5 | Compound 1-6 | 3.89 | 4.65 | (0.137, 0.129) |
| Experimental Example 6 | Compound 1-15 | 3.90 | 4.61 | (0.136, 0.129) |
| Experimental Example 7 | Compound 1-24 | 3.93 | 4.63 | (0.137, 0.128) |
| Experimental Example 8 | Compound 1-47 | 3.91 | 4.62 | (0.138, 0.129) |
| Experimental Example 9 | Compound 2-1 | 3.95 | 4.64 | (0.138, 0.128) |
| Experimental Example 10 | Compound 2-3 | 3.90 | 4.62 | (0.138, 0.129) |
| Experimental Example 11 | Compound 2-4 | 3.96 | 4.55 | (0.136, 0.128) |
| Experimental Example 12 | Compound 2-5 | 3.98 | 4.52 | (0.137, 0.127) |
| Experimental Example 13 | Compound 2-15 | 3.96 | 4.48 | (0.137, 0.129) |
| Experimental Example 14 | Compound 2-24 | 3.98 | 4.46 | (0.136, 0.129) |
| Experimental Example 15 | Compound 2-47 | 3.94 | 4.53 | (0.137, 0.130) |
| Comparative Example 1 | ET1 | 4.02 | 3.95 | (0.136, 0.130) |
| Comparative Example 2 | ET2 | 4.13 | 3.87 | (0.136, 0.126) |
| Comparative Example 3 | ET3 | 4.16 | 3.70 | (0.132, 0.129) |
| Comparative Example 4 | ET4 | 4.25 | 3.61 | (0.131, 0.132) |

As seen in Table 1, it can be confirmed that comparing Experimental Examples 1, 2, 3, 4, and 5 and Comparative Examples 1 and 2, in the case where Ar3 is a 1,5-naphthyl group, an electron transporting and injection ability is better than that of a 1,4-phenyl group.

As seen in Table 1, it can be confirmed that comparing Experimental Examples 6, 7, 8, and 9 and Comparative Examples 3 to 4 to each other, in the case where Ar3 is the 1,5-naphthyl group, the electron transporting and injection ability is better than that of the 1,4-phenyl group.

As shown in the result of Table 1, it could be confirmed that the compound according to the present invention has the excellent electron transporting and injection ability and thus can be applied to the organic light emitting device.

The invention claimed is:

1. A hetero-cyclic compound represented by the following Chemical Formula 1:

[Chemical Formula 1]

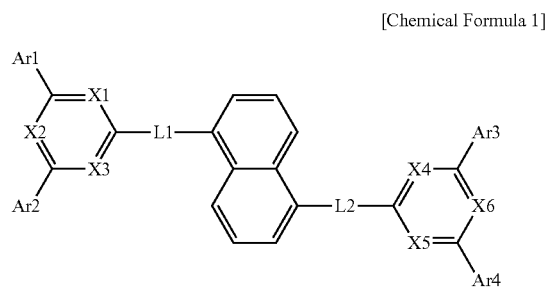

in Chemical Formula 1,

X1 to X6 are the same as or different from each other, and are each independently a trivalent hetero atom or CH, at least one of X1 to X3 is CH or at least one of X4 to X6 is CH, at least one of X1 to X3 is N or at least one of X4 to X6 is N, L1 and L2 are the same as each other, and are a direct bond; or a phenylene group, Ar1 to Ar4 are the same as or different from each other, and are each independently an unsubstituted phenyl group, a phenyl group substituted by a nitrile group, a biphenyl group, a terphenyl group, a naphthyl group, a fluorenyl group substituted by a methyl group or a phenyl group, a phenanthryl group, a pyridine group, or a thiophene group, and

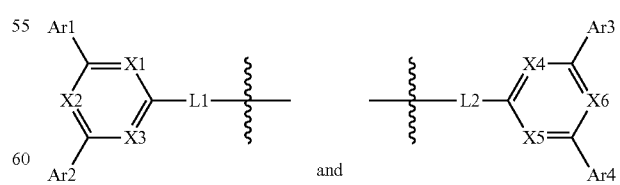

and are the same as each other.

2. The hetero-cyclic compound of claim 1, wherein the compound represented by Chemical Formula 1 is represented by any one of the following Chemical Formulas 1-1 to 1-50:

Chemical Formula 1-1
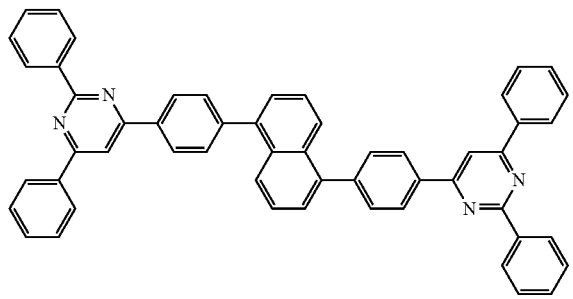
Chemical Formula 1-2
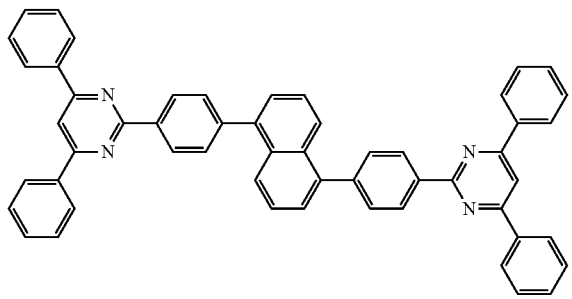
Chemical Formula 1-3
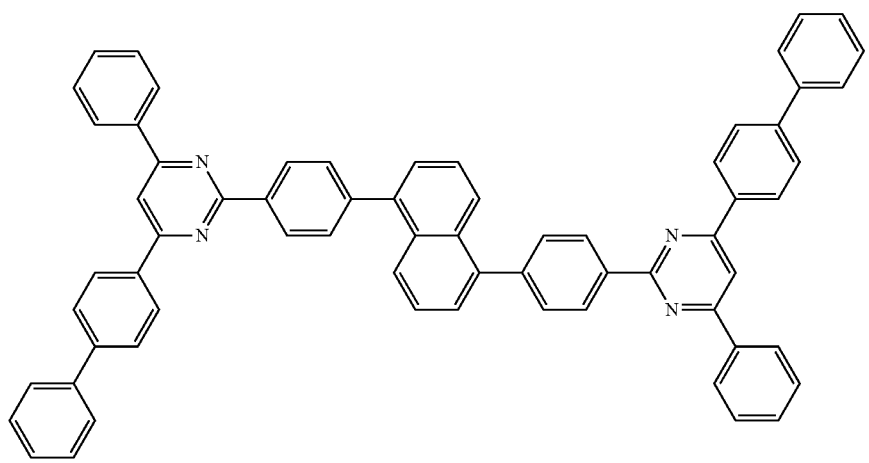
Chemical Formula 1-4
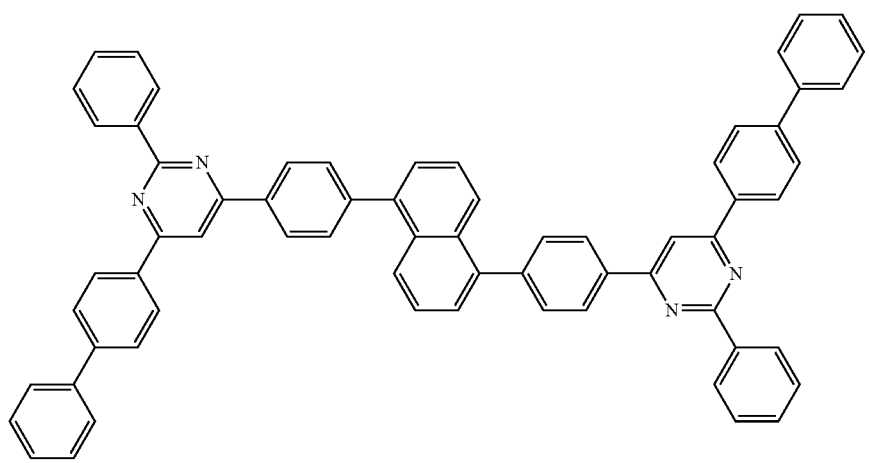
Chemical Formula 1-5
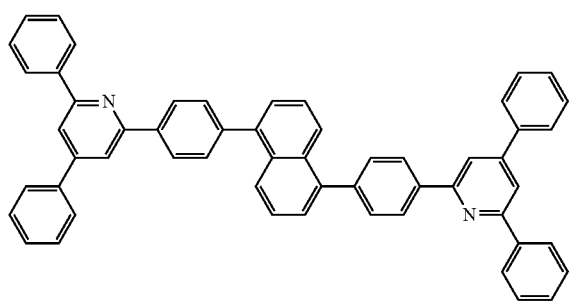
Chemical Formula 1-6
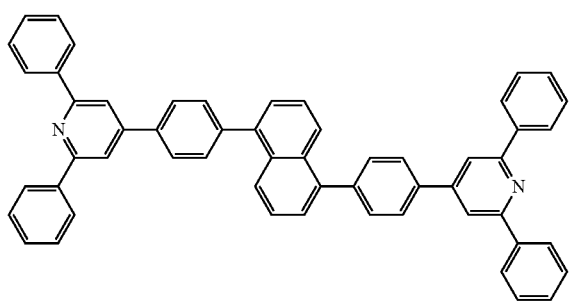

Chemical Formula 1-7
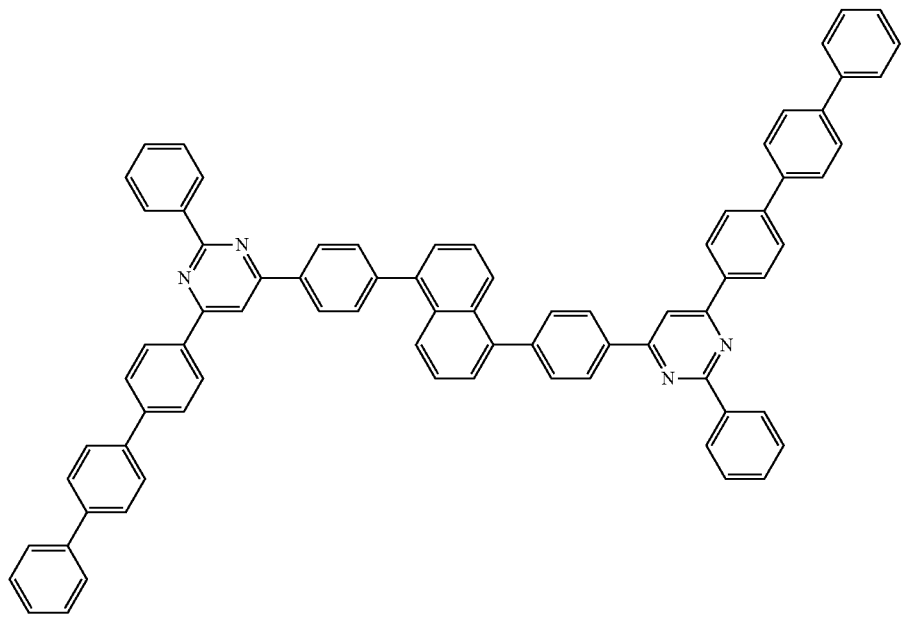
Chemical Formula 1-8
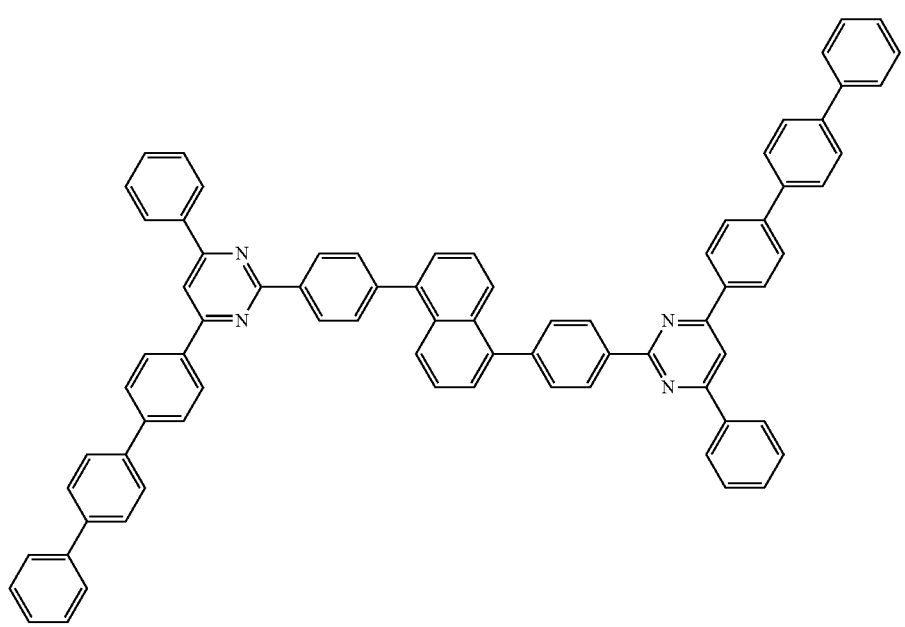

Chemical Formula 1-9
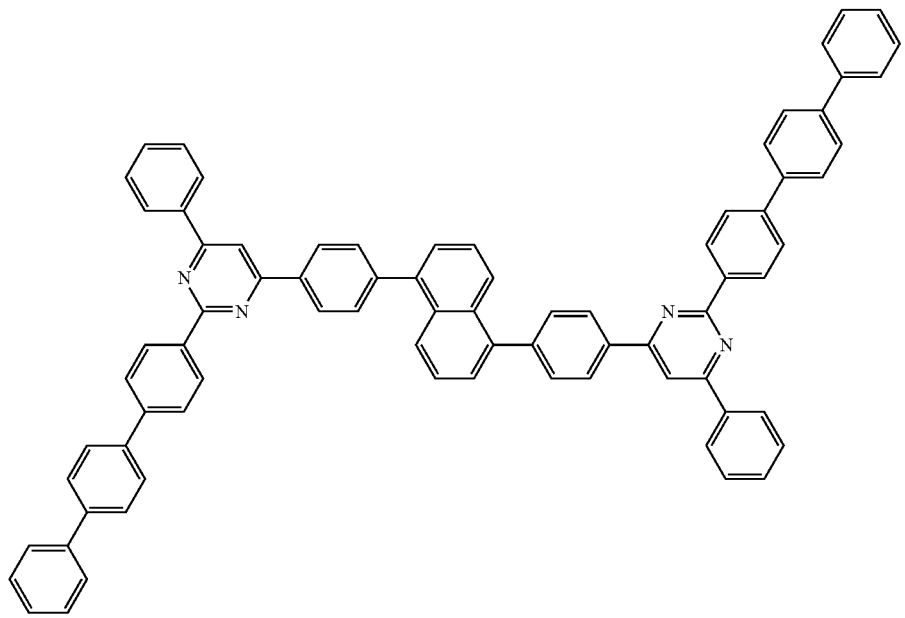
Chemical Formula 1-10
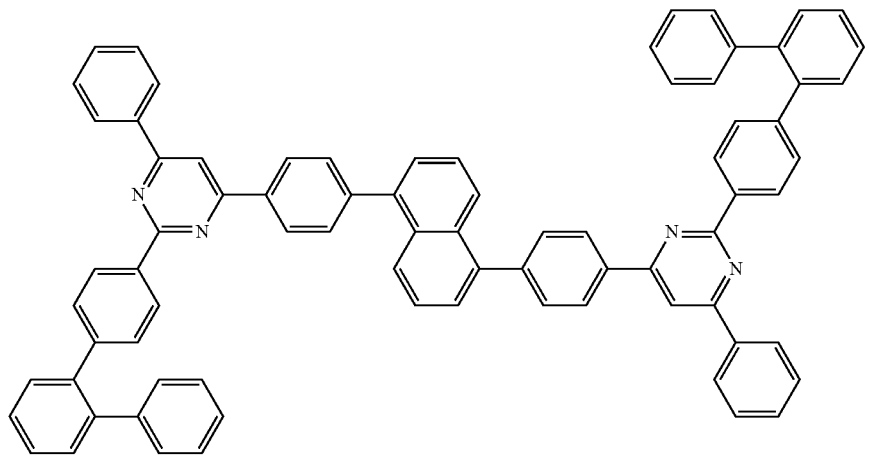
Chemical Formula 1-11
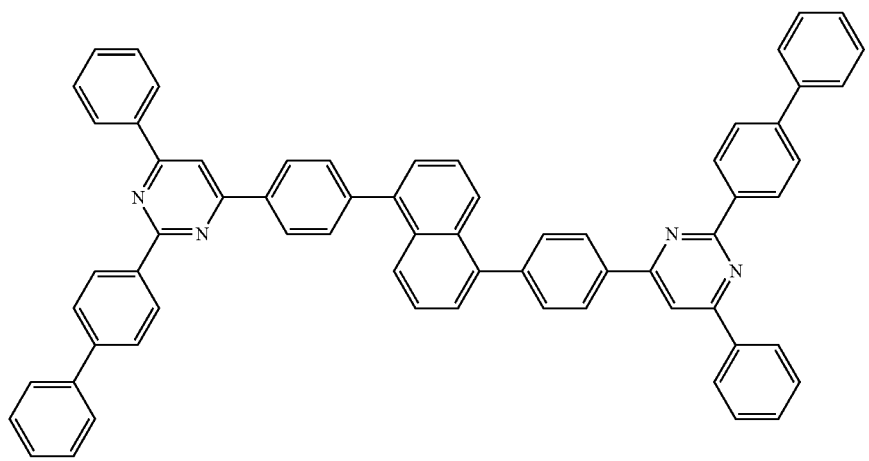

Chemical Formula 1-12
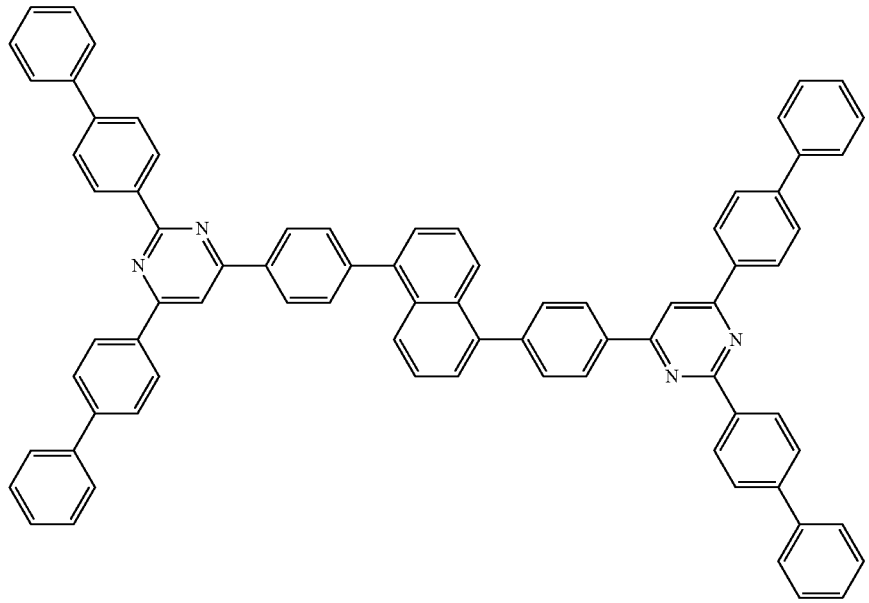
Chemical Formula 1-13
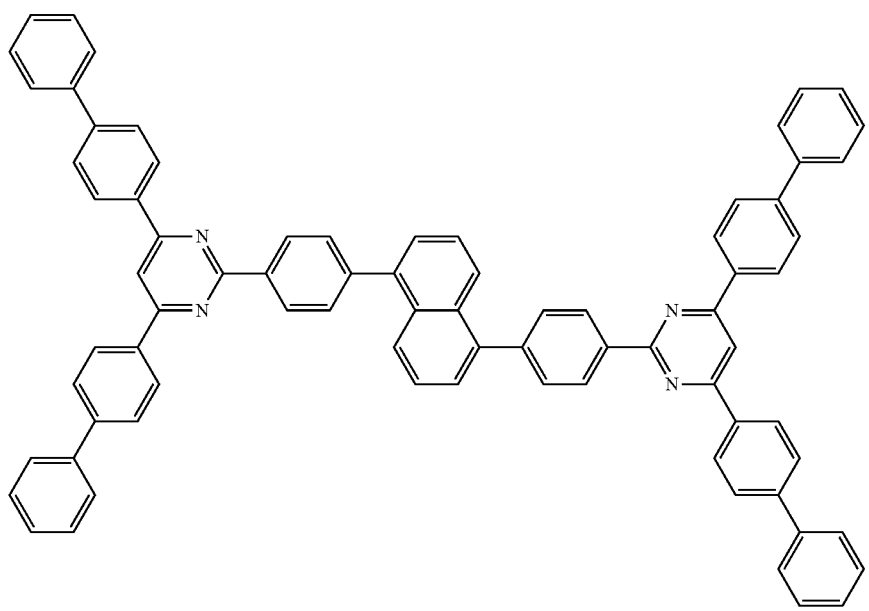

Chemical Formula 1-14
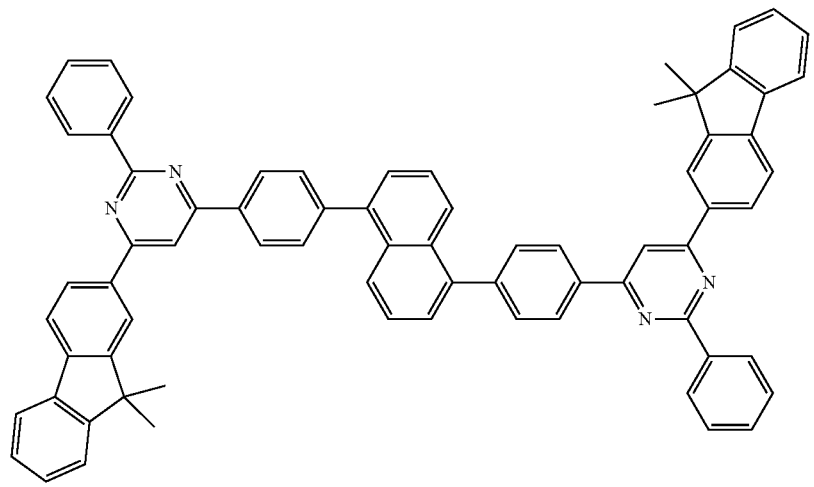
Chemical Formula 1-15
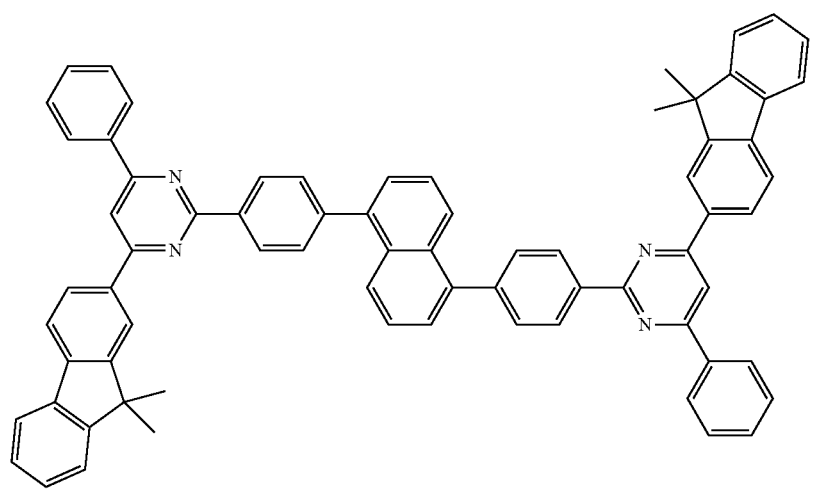
Chemical Formula 1-16
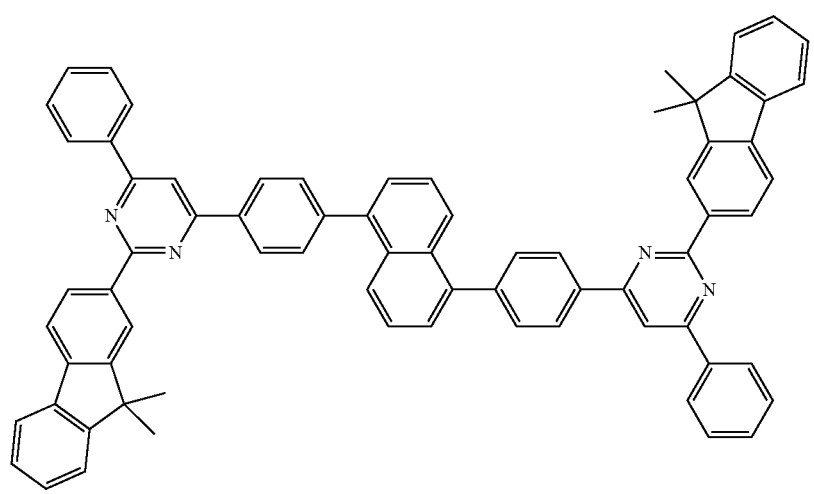

Chemical Formula 1-17
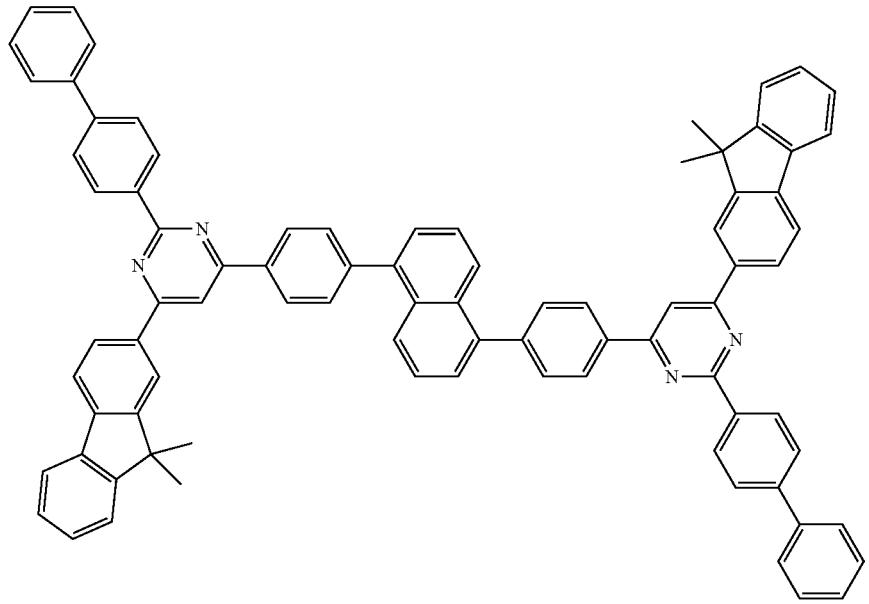
Chemical Formula 1-18
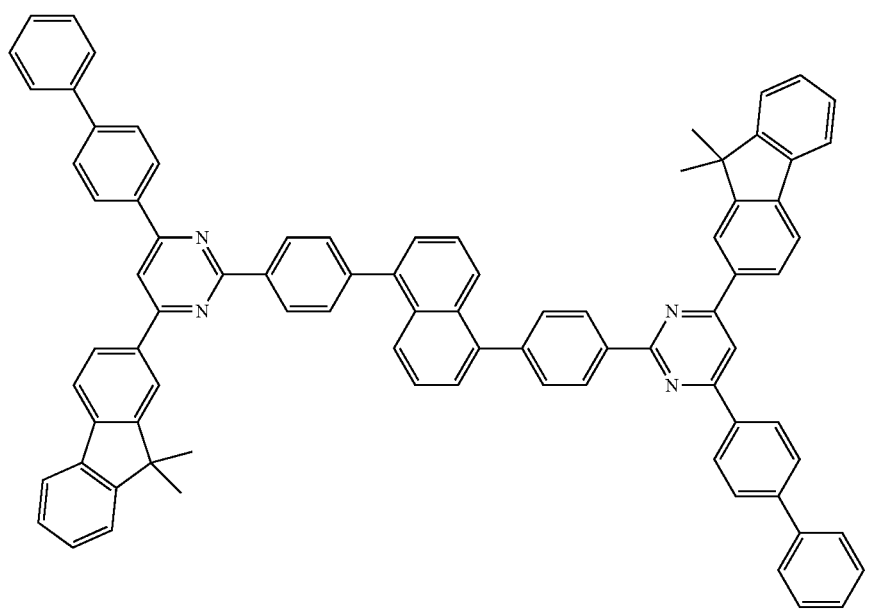

Chemical Formula 1-19
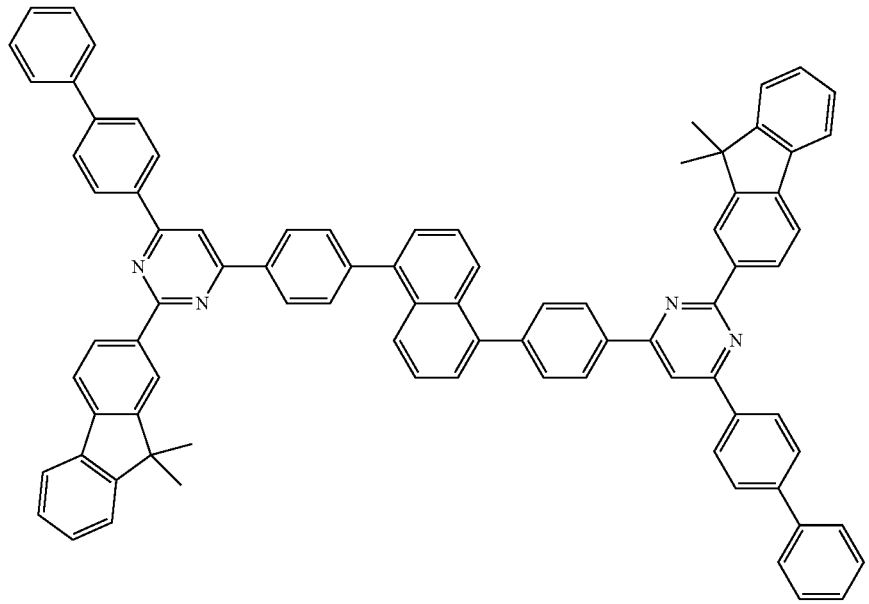
Chemical Formula 1-20
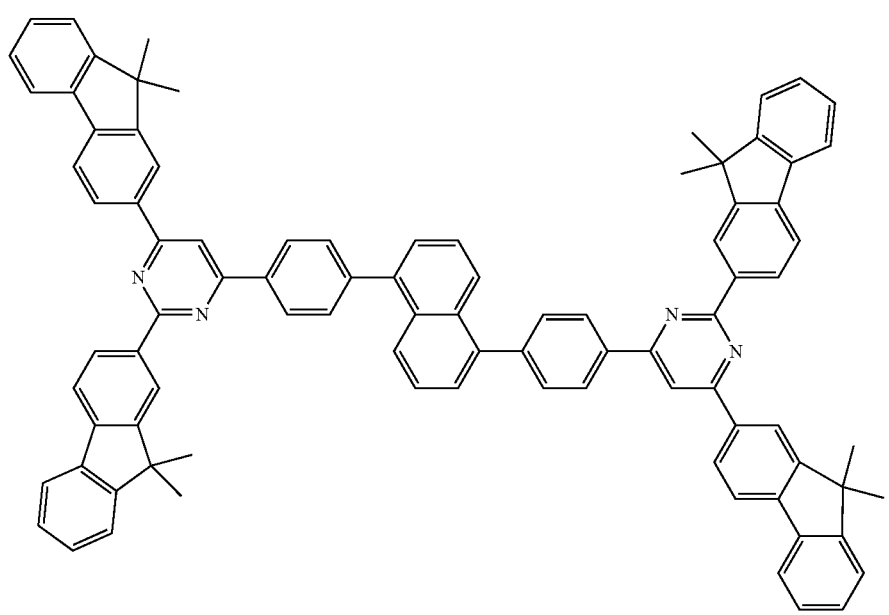

Chemical Formula 1-21
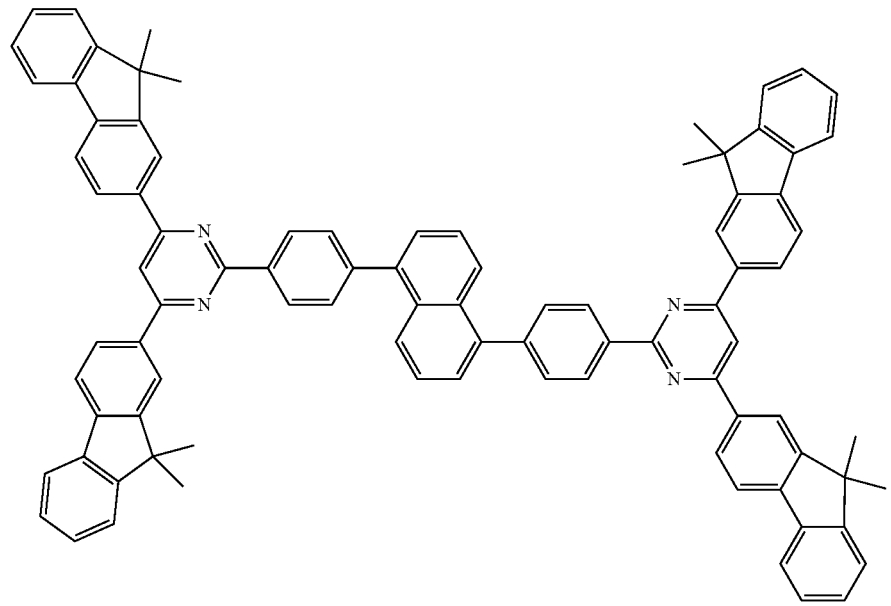
Chemical Formula 1-22
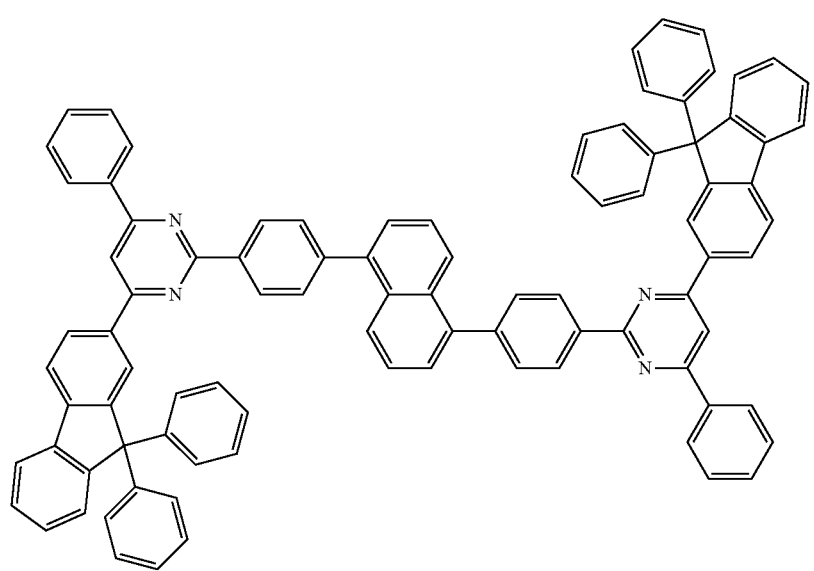

Chemical Formula 1-23
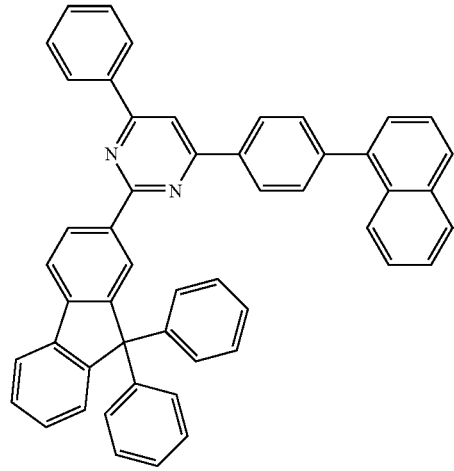
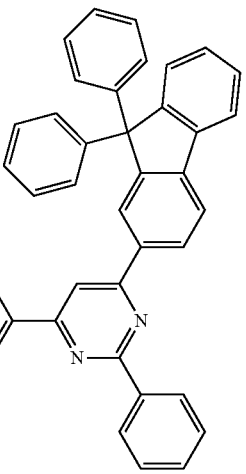
Chemical Formula 1-24
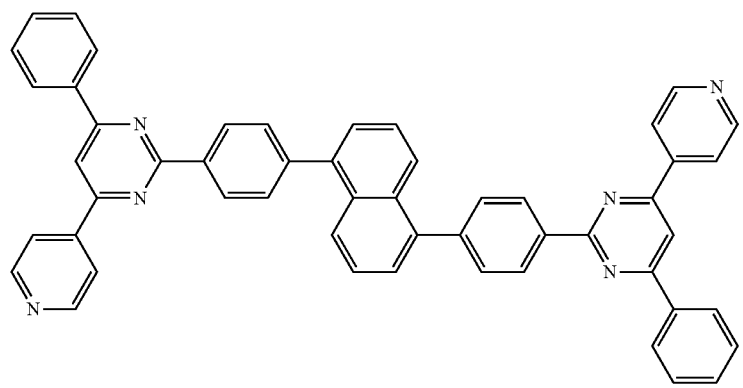
Chemical Formula 1-25
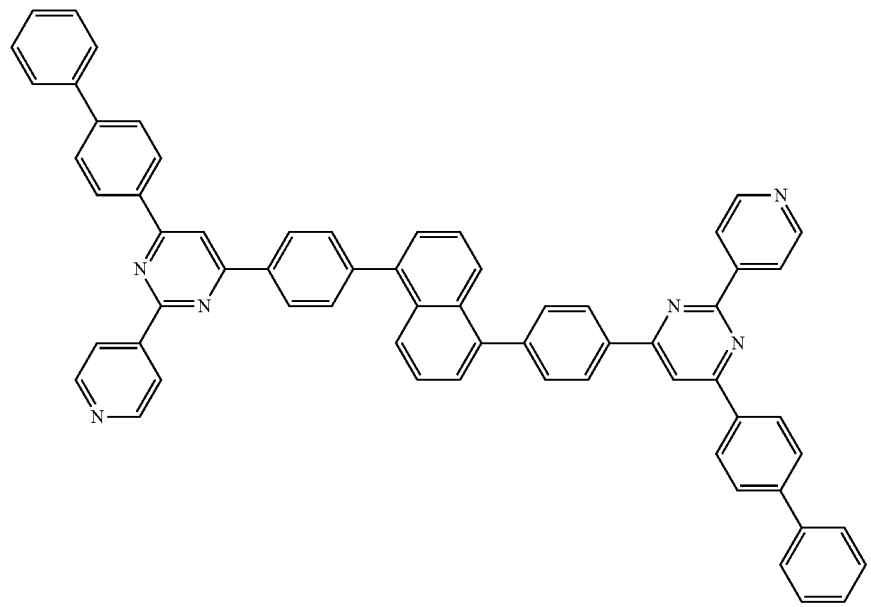

Chemical Formula 1-26
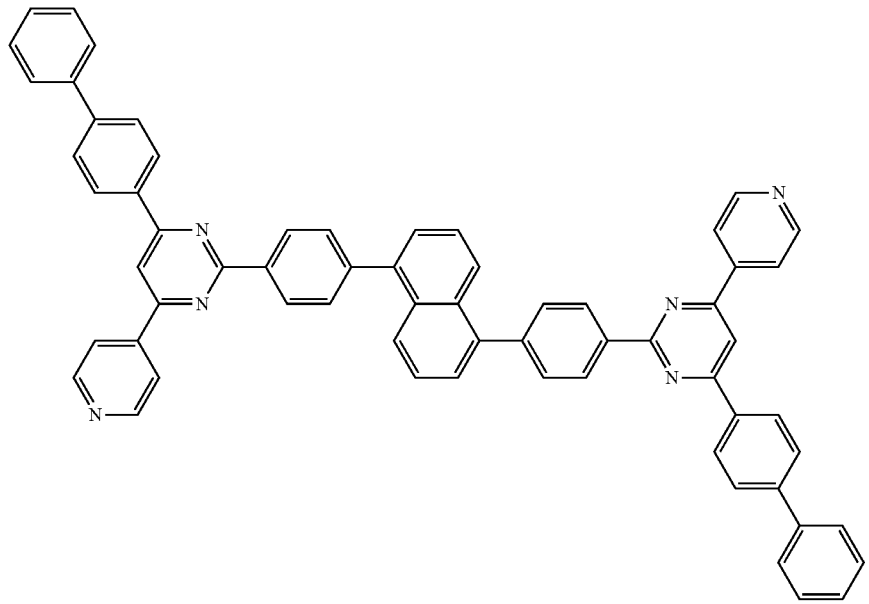
Chemical Formula 1-27
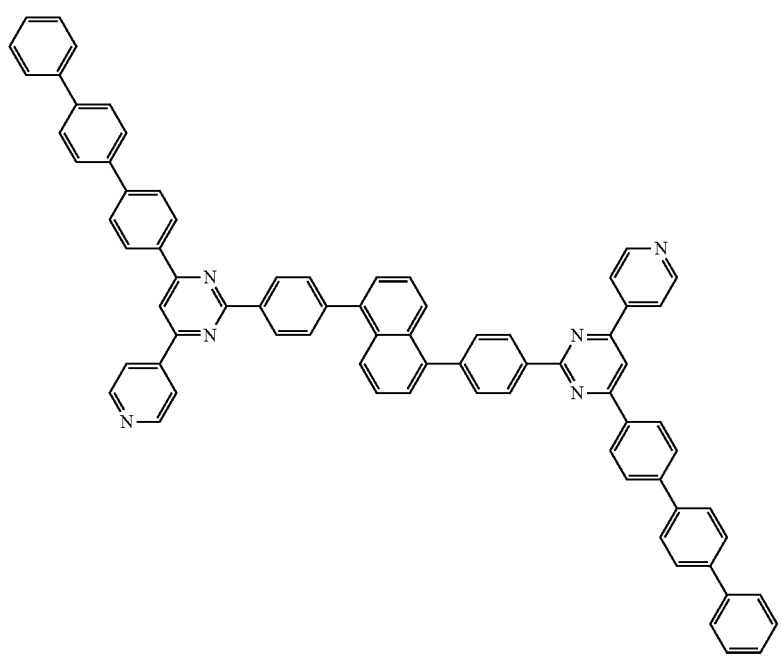

Chemical Formula 1-28
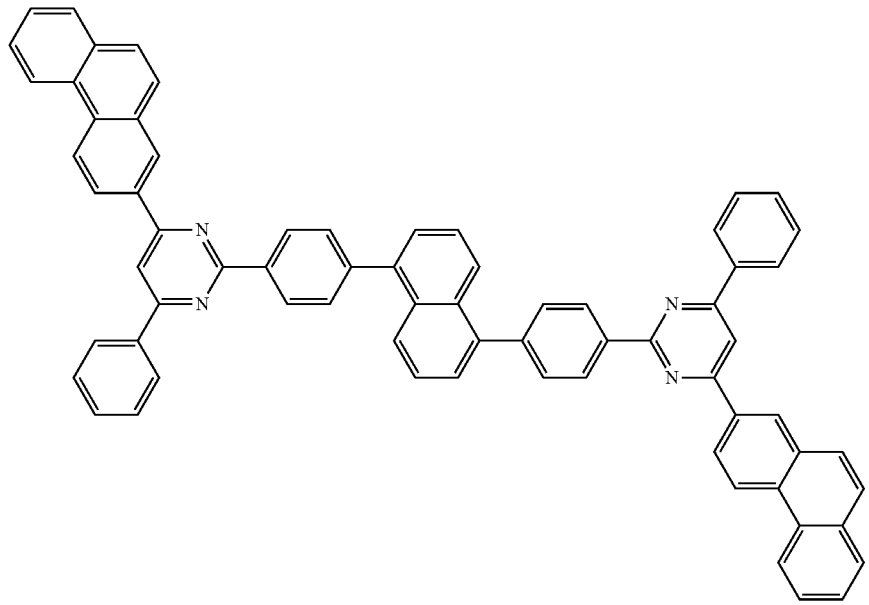
Chemical Formula 1-29
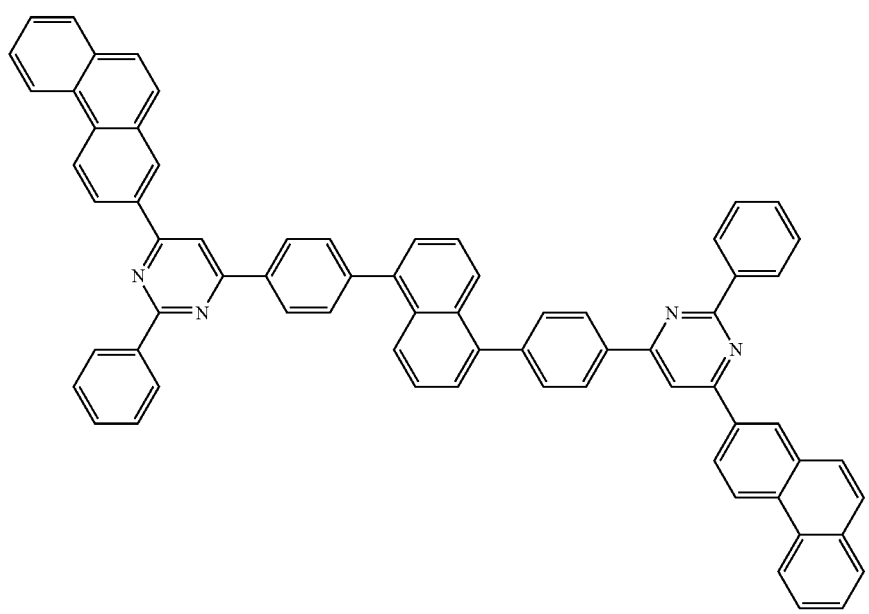

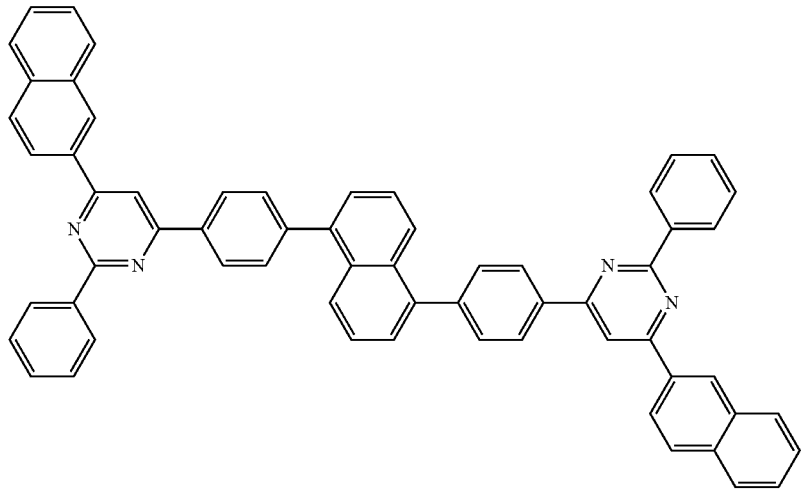
Chemical Formula 1-30
Chemical Formula 1-31
Chemical Formula 1-32

Chemical Formula 1-33
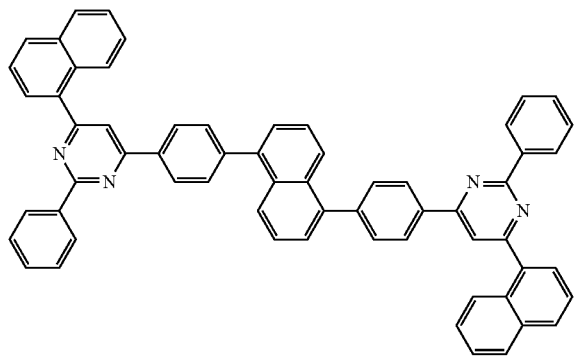
Chemical Formula 1-34
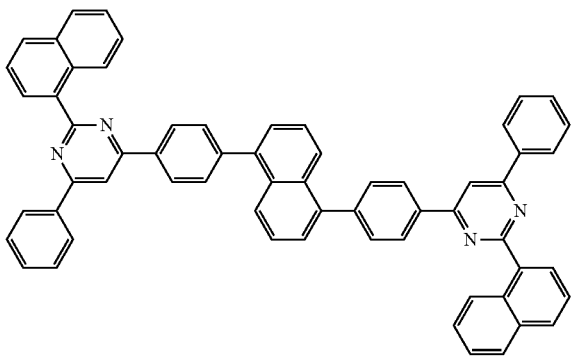
Chemical Formula 1-35
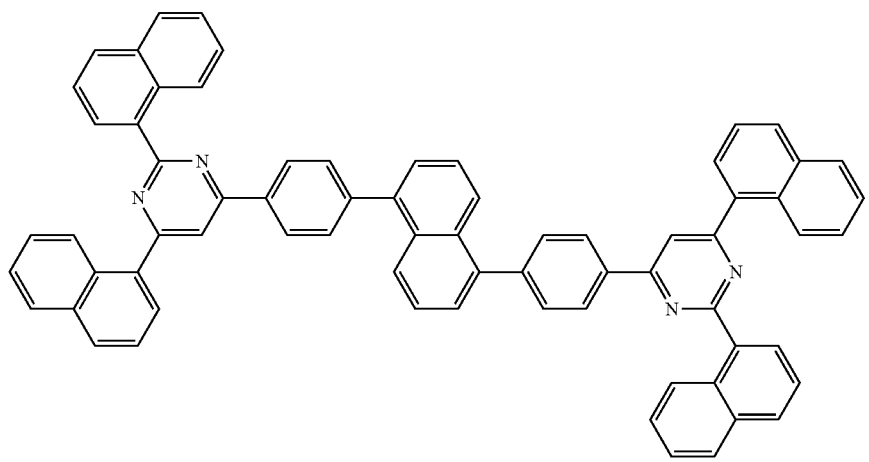
Chemical Formula 1-36
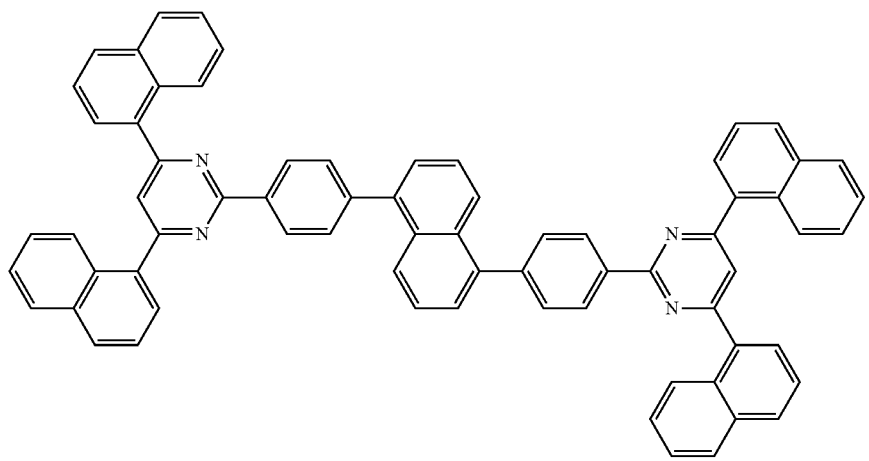

Chemical Formula 1-37
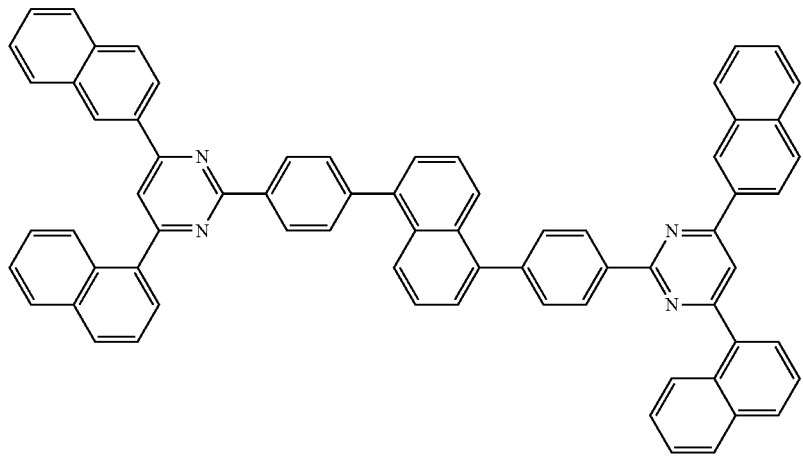
Chemical Formula 1-38
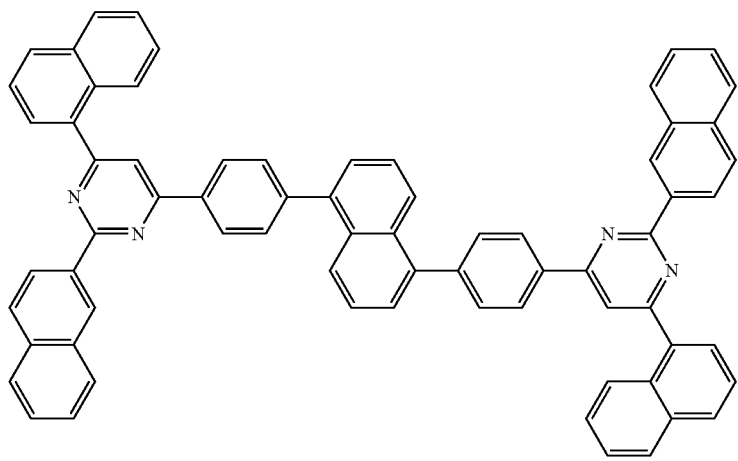
Chemical Formula 1-39
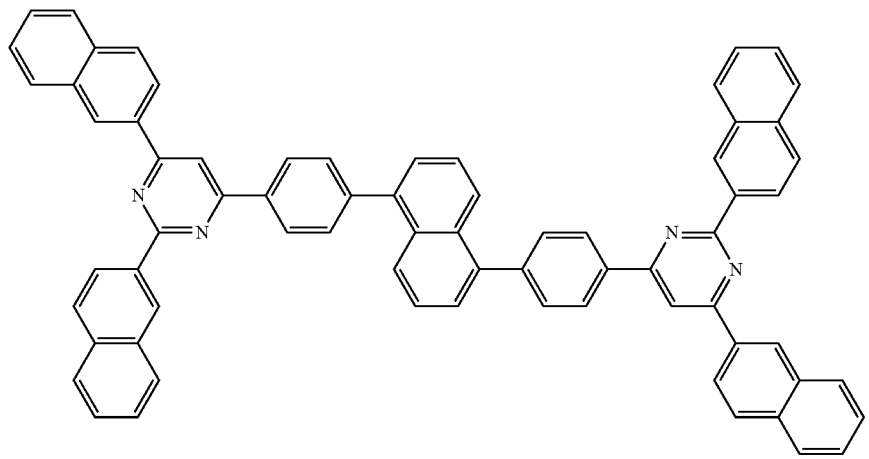

-continued
Chemical Formula 1-40
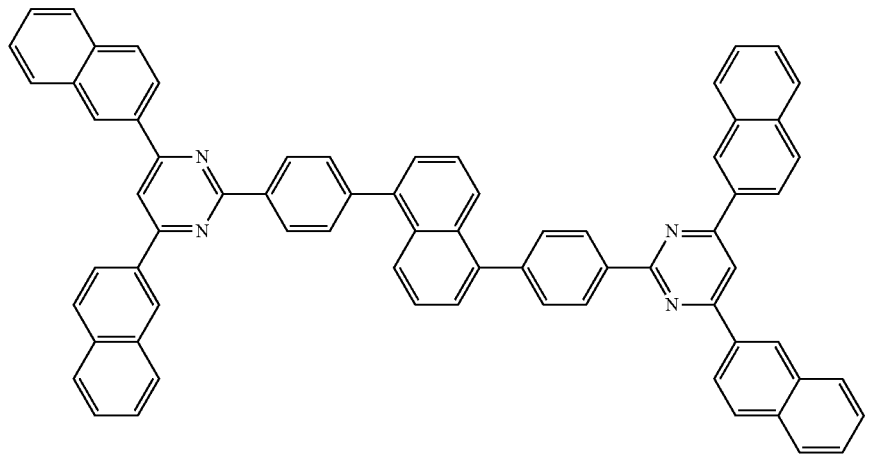
Chemical Formula 1-41
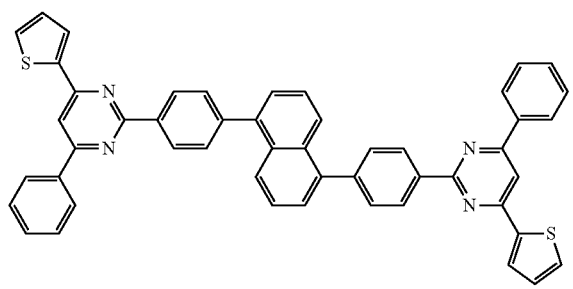
Chemical Formula 1-42
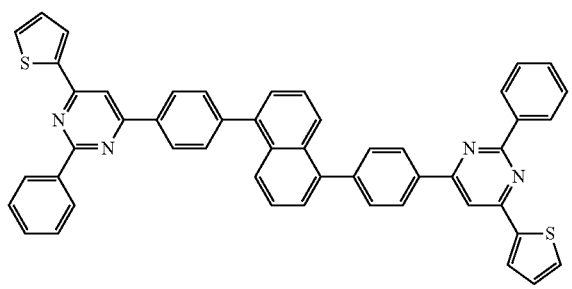
Chemical Formula 1-43
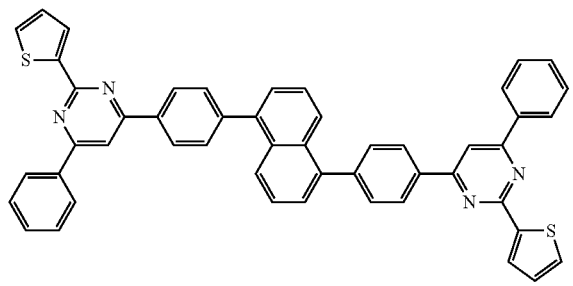
Chemical Formula 1-44
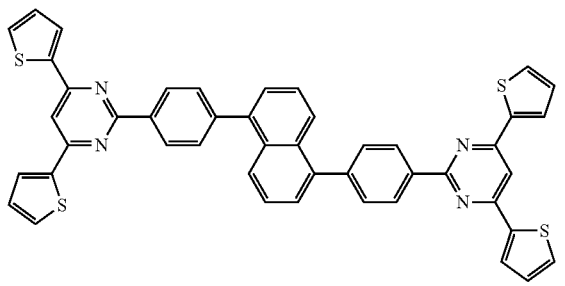
Chemical Formula 1-45
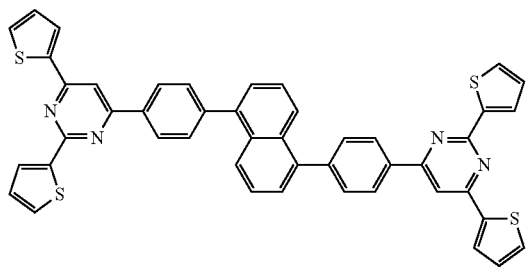
Chemical Formula 1-46
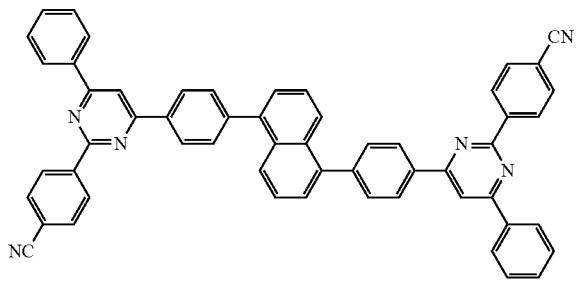

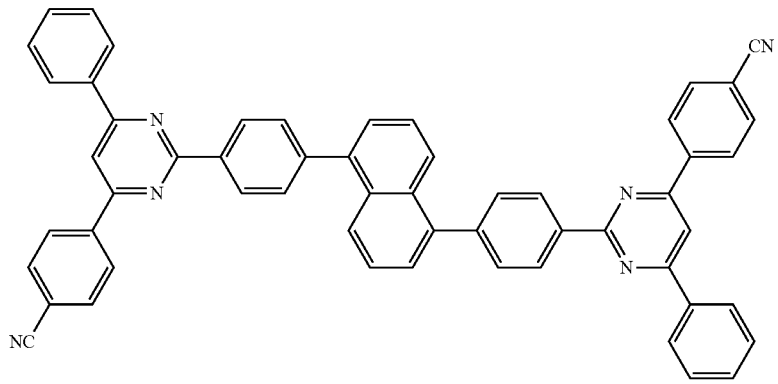
Chemical Formula 1-47
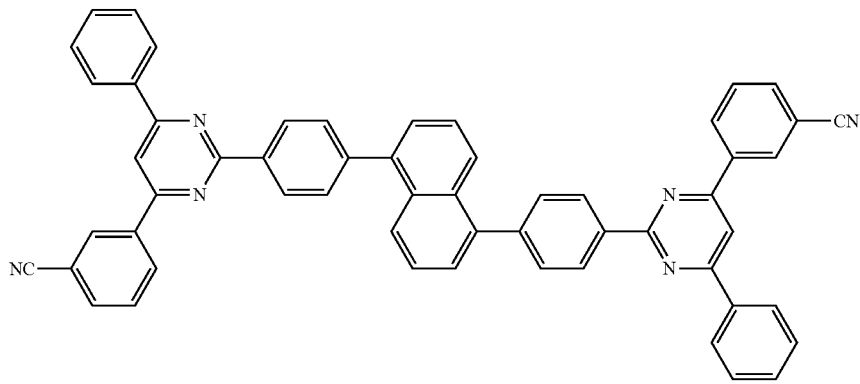
Chemical Formula 1-48
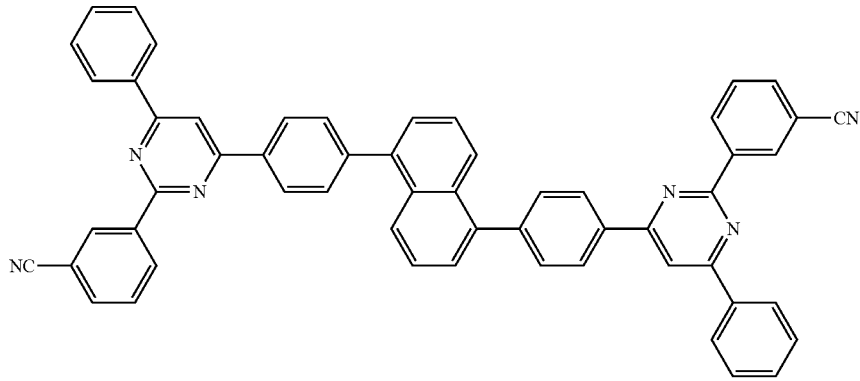
Chemical Formula 1-49
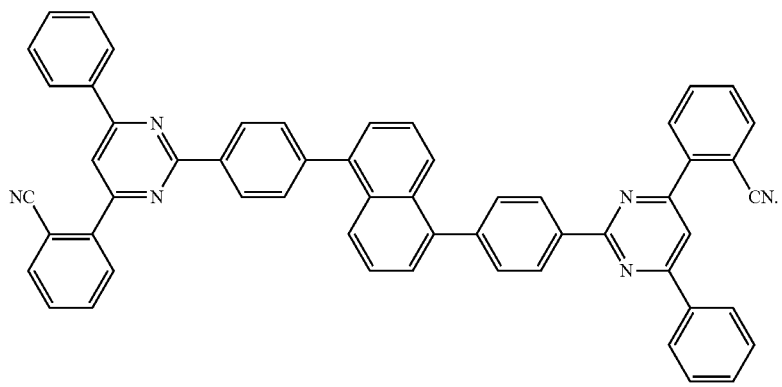
Chemical Formula 1-50

3. The hetero-cyclic compound of claim 1, wherein the compound represented by Chemical Formula 1 is represented by any one of the following Chemical Formulas 2-1 to 2-50:
Chemical Formula 2-1
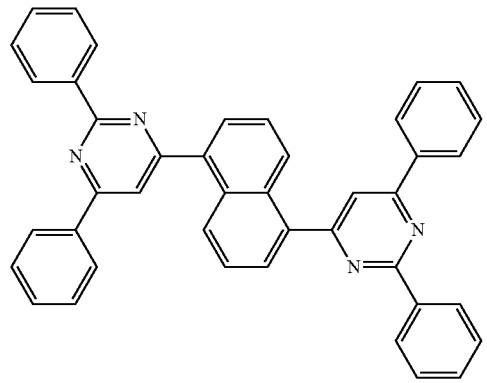
Chemical Formula 2-2
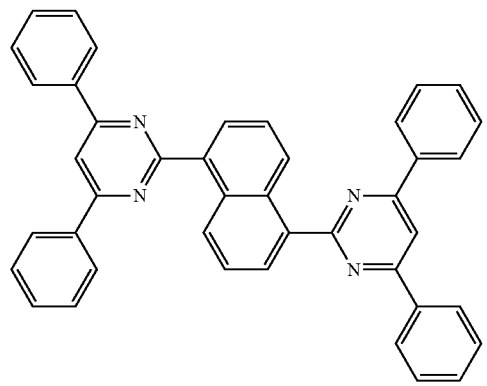
Chemical Formula 2-3
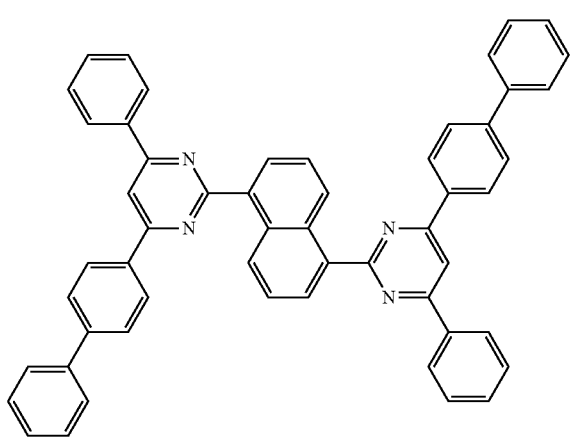
-continued
Chemical Formula 2-4
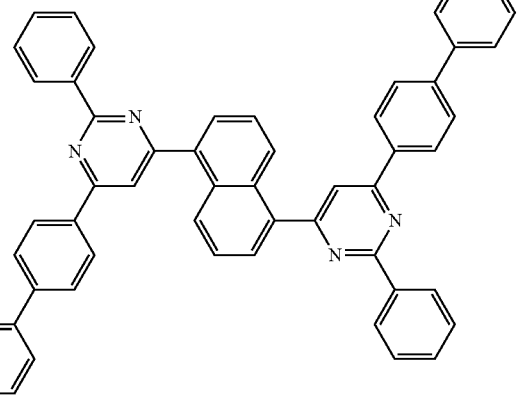
Chemical Formula 2-5
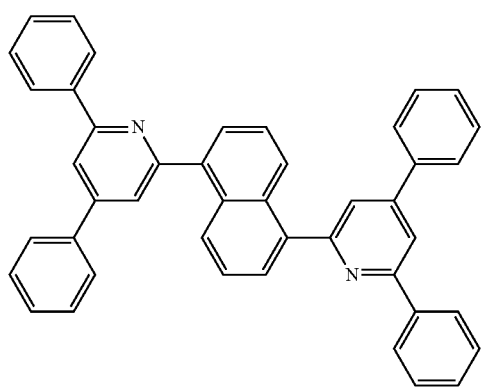
Chemical Formula 2-6
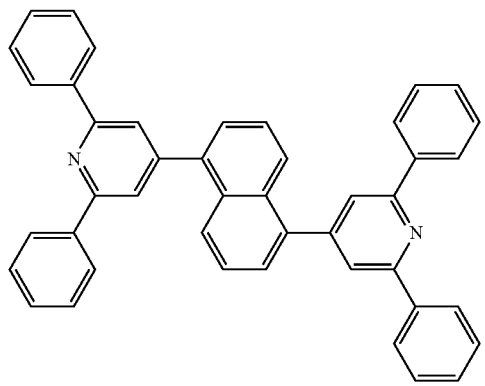

Chemical Formula 2-7
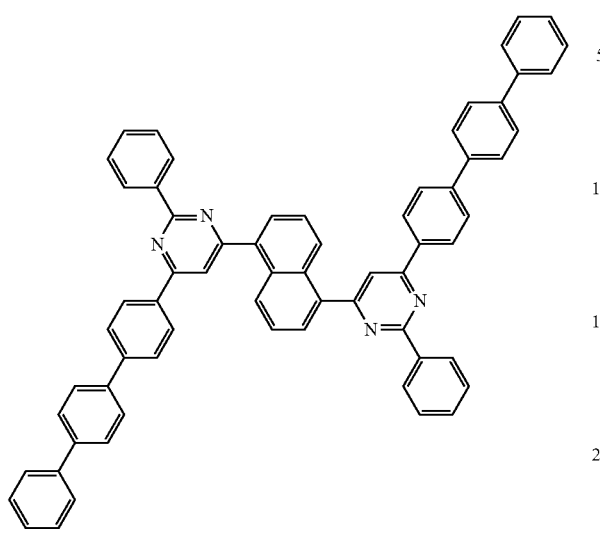
Chemical Formula 2-8
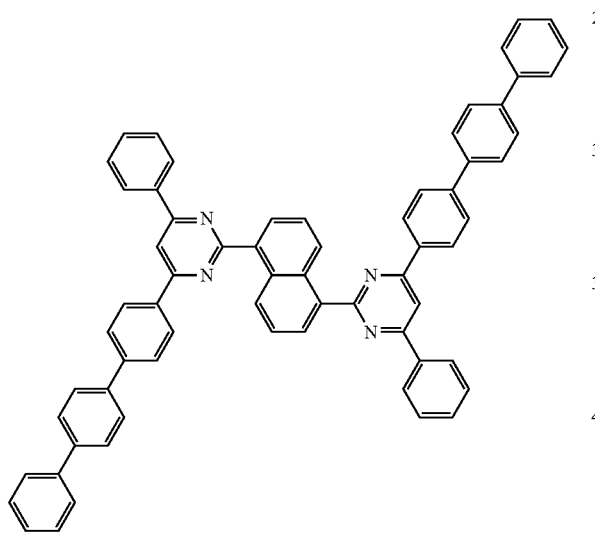
Chemical Formula 2-9
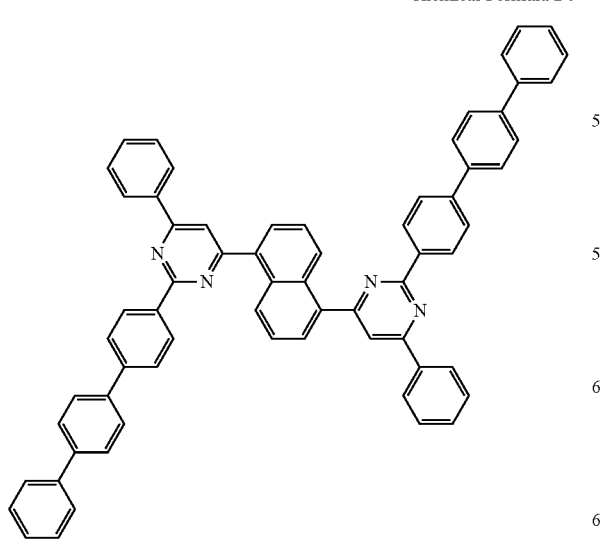
Chemical Formula 2-10
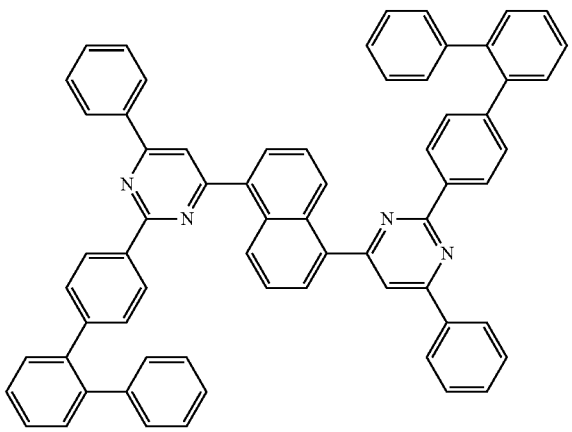
Chemical Formula 2-11
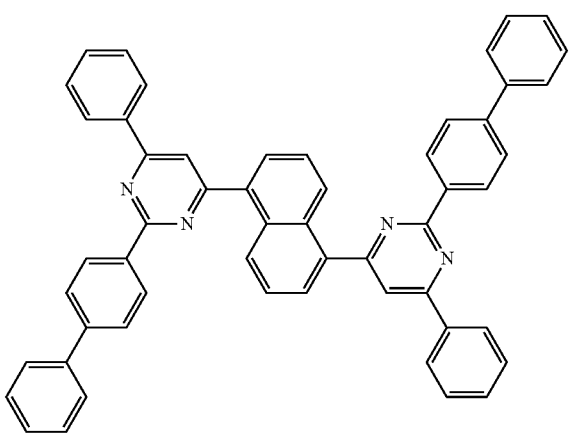
Chemical Formula 2-12
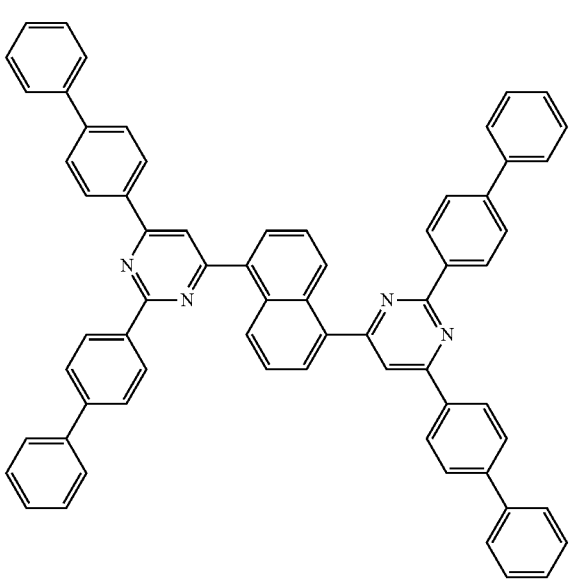

Chemical Formula 2-13
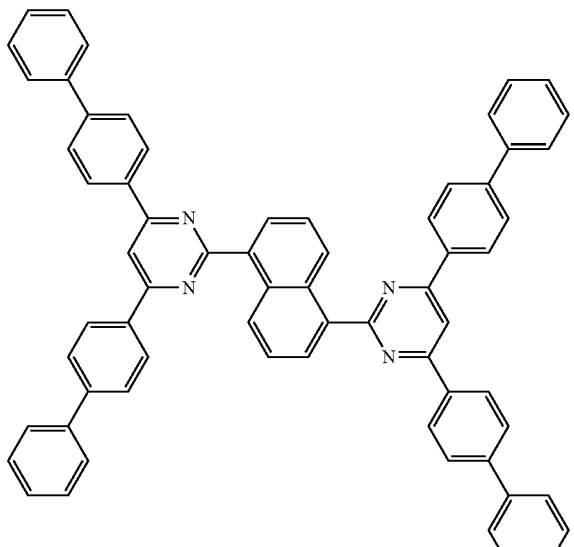
Chemical Formula 2-14
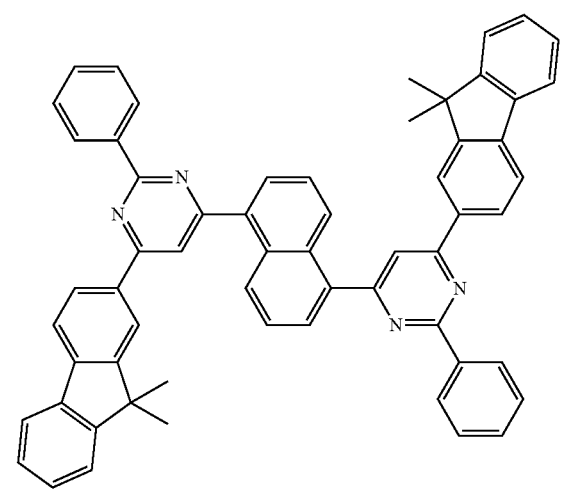
Chemical Formula 2-15
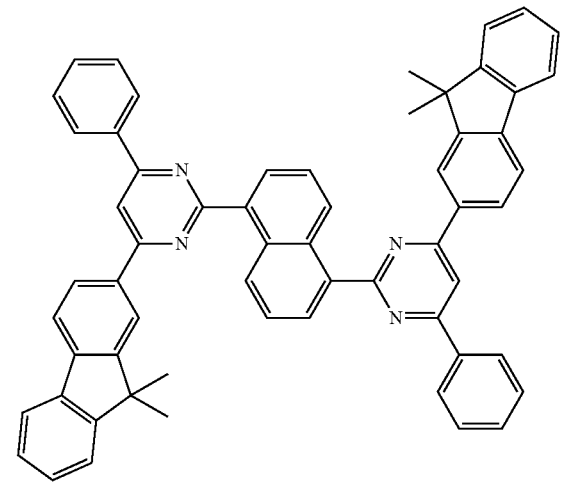
Chemical Formula 2-16
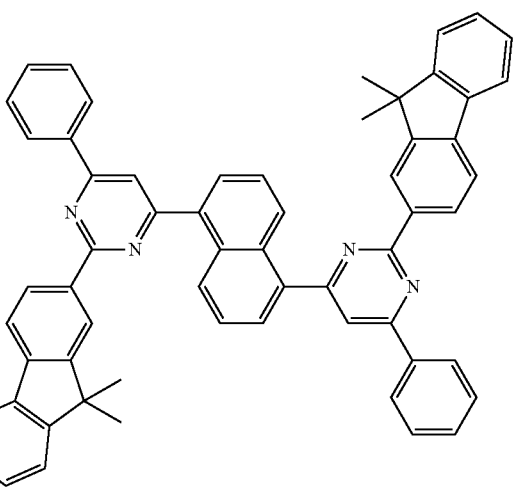
Chemical Formula 2-17
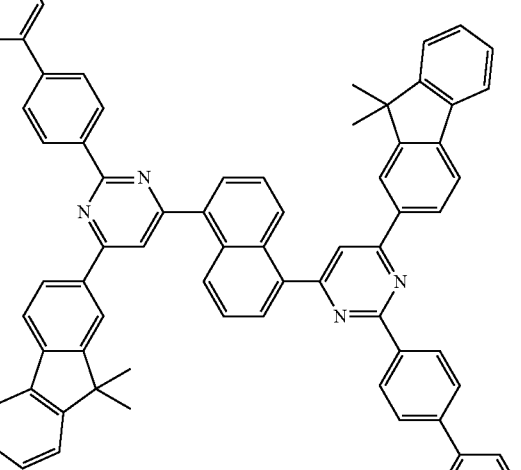

Chemical Formula 2-18
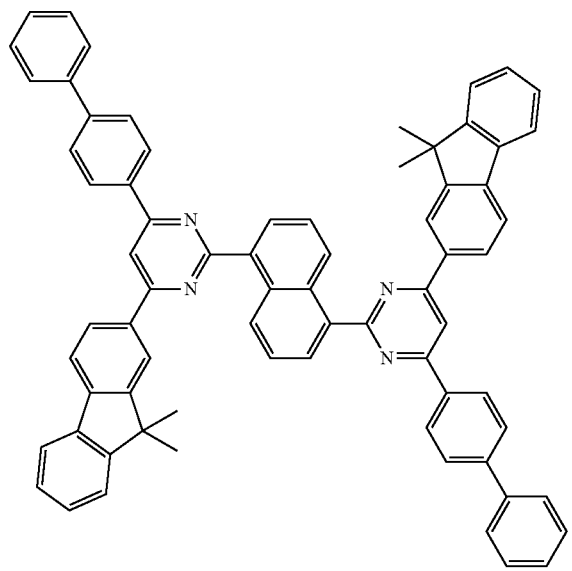
Chemical Formula 2-19
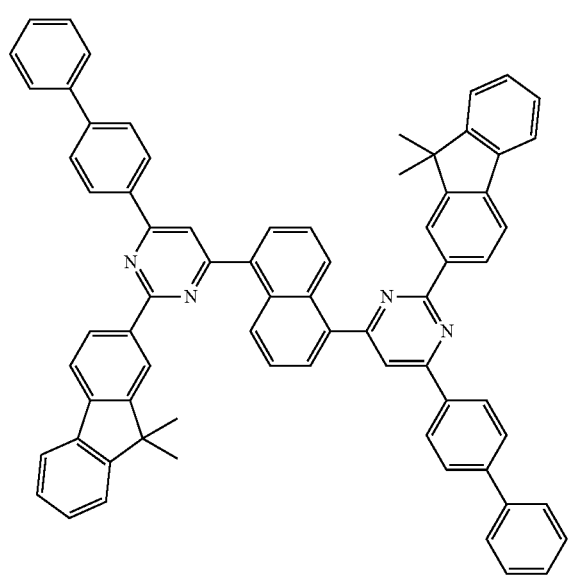
Chemical Formula 2-20
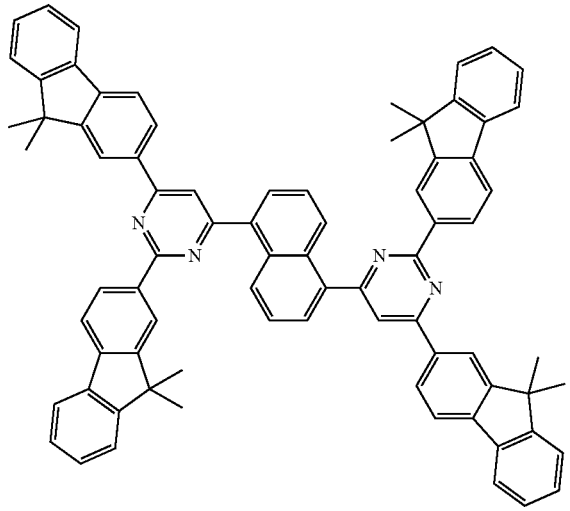
Chemical Formula 2-21
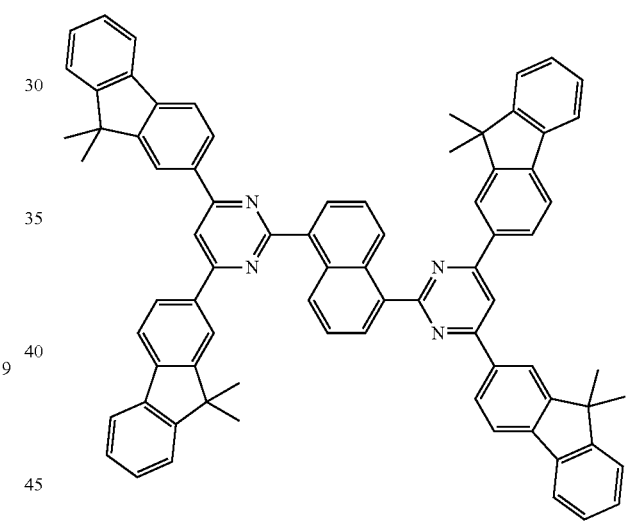
Chemical Formula 2-22
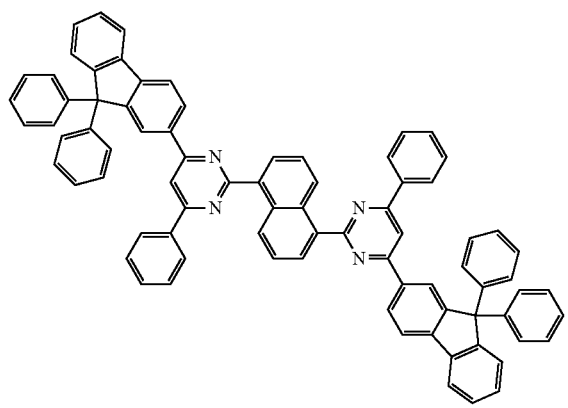

Chemical Formula 2-23
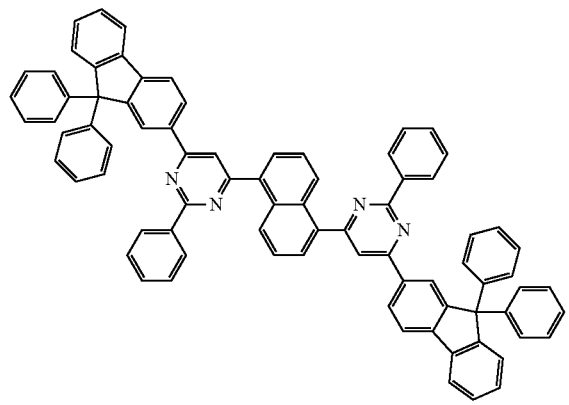
Chemical Formula 2-24
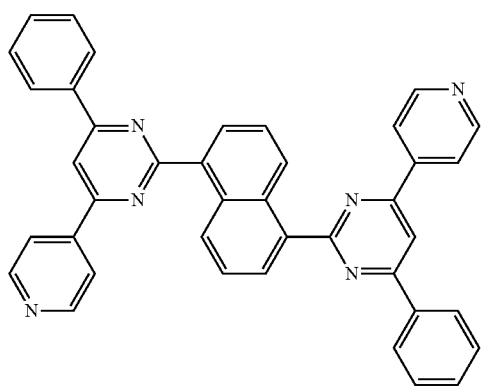
Chemical Formula 2-25
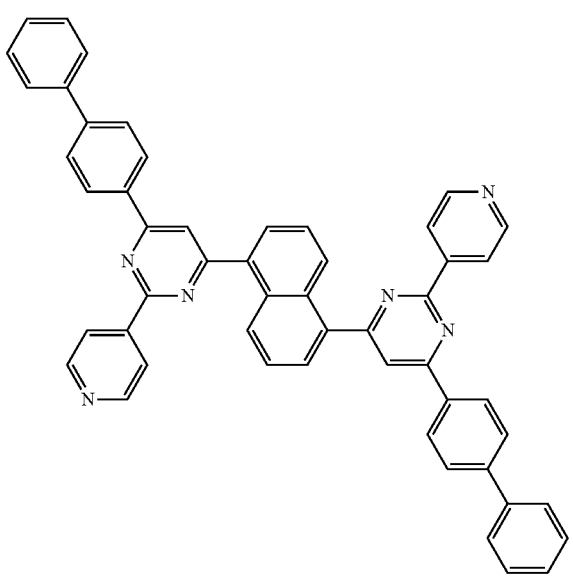
Chemical Formula 2-26
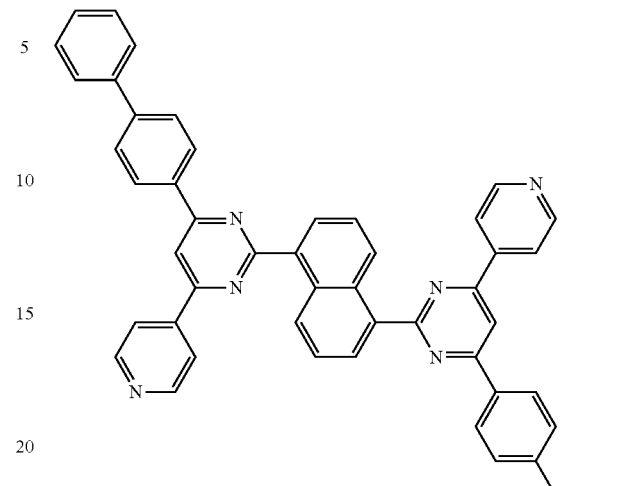
Chemical Formula 2-27
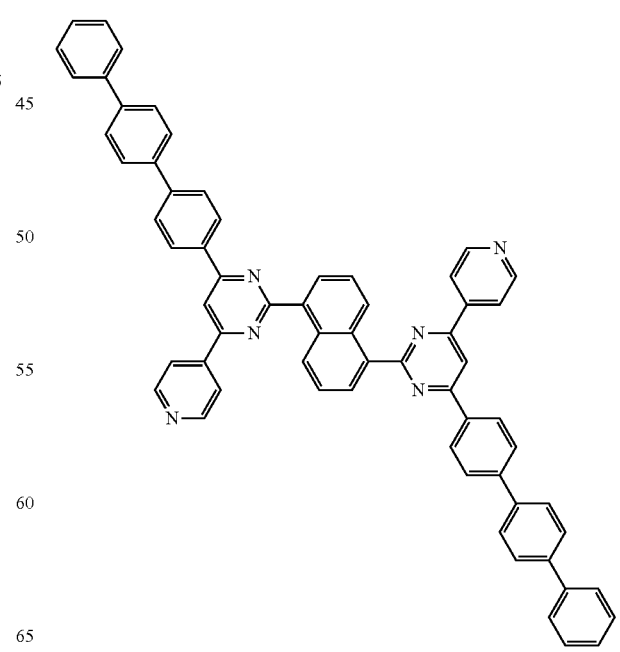

Chemical Formula 2-28
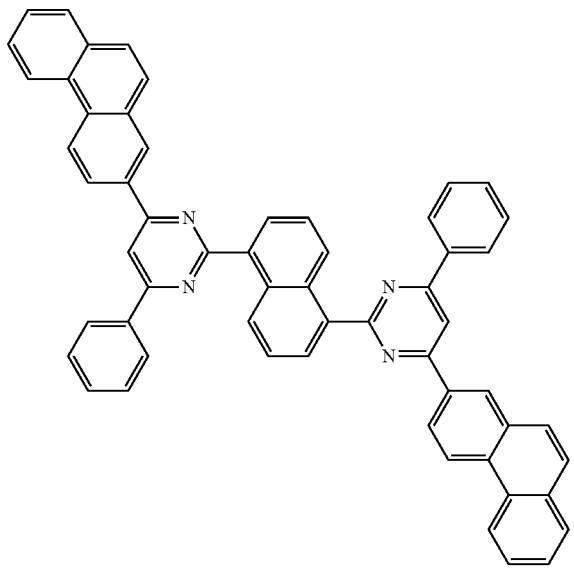
Chemical Formula 2-30
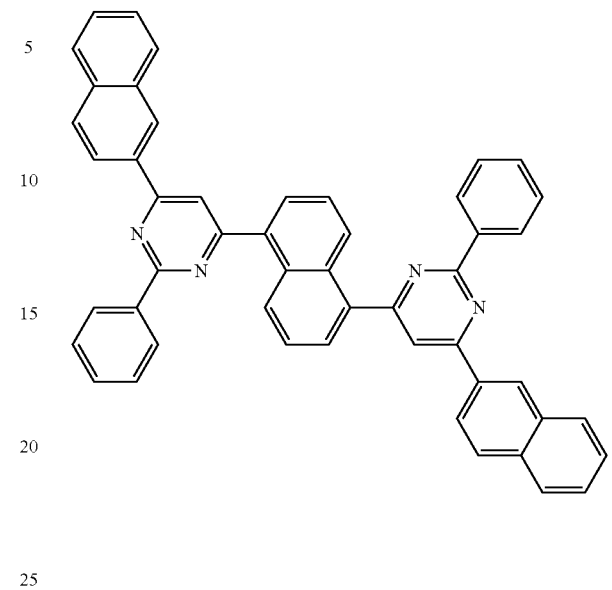
Chemical Formula 2-31
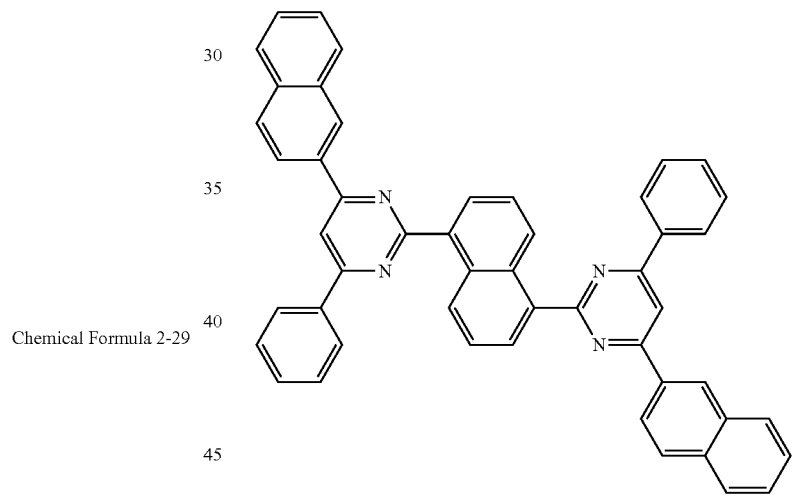
Chemical Formula 2-29
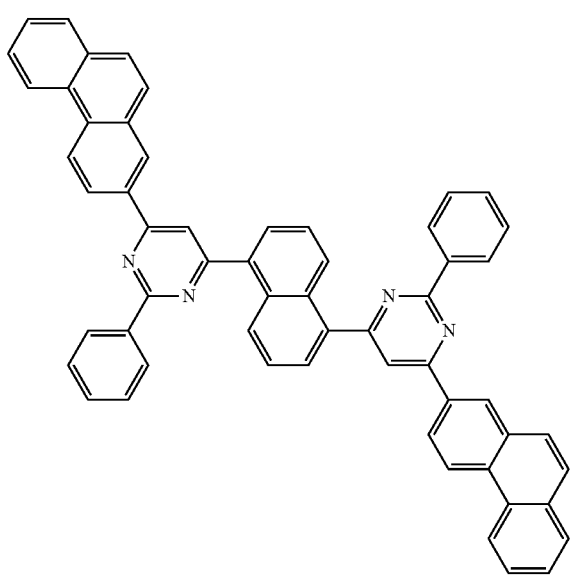
Chemical Formula 2-32
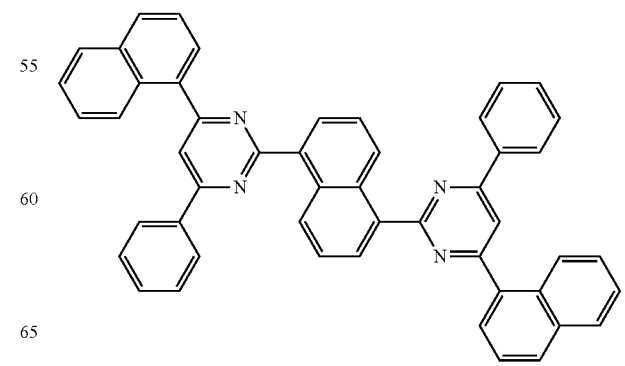

Chemical Formula 2-33
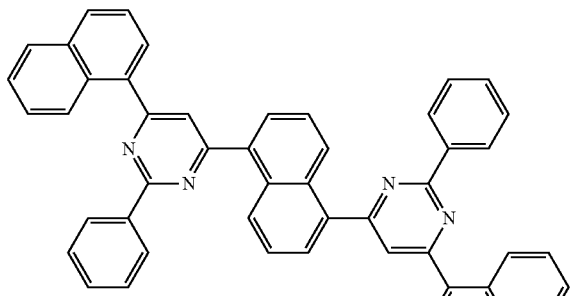
Chemical Formula 2-34
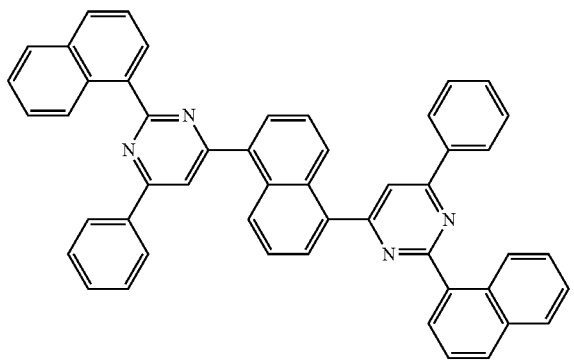
Chemical Formula 2-35
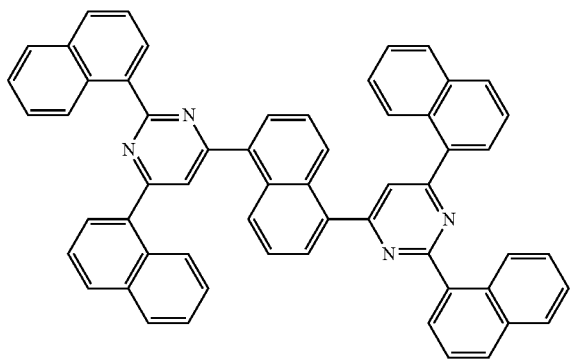
Chemical Formula 2-36
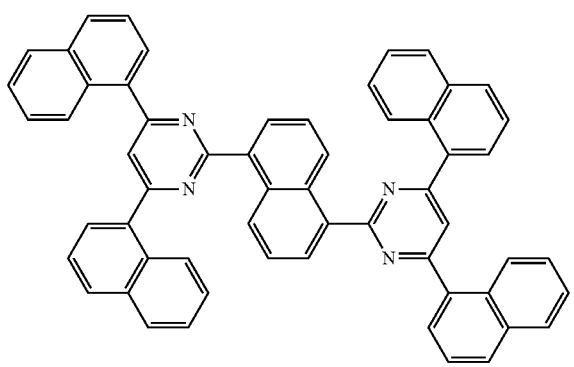
Chemical Formula 2-37
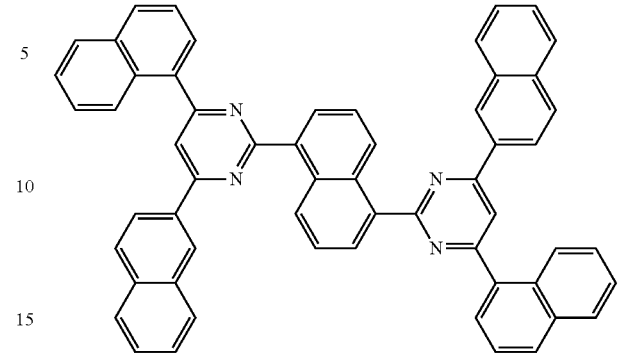
Chemical Formula 2-38
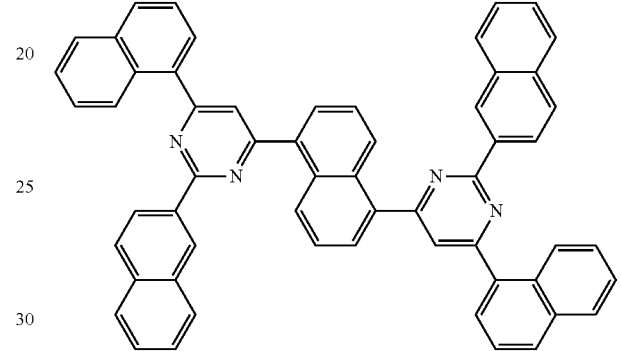
Chemical Formula 2-39
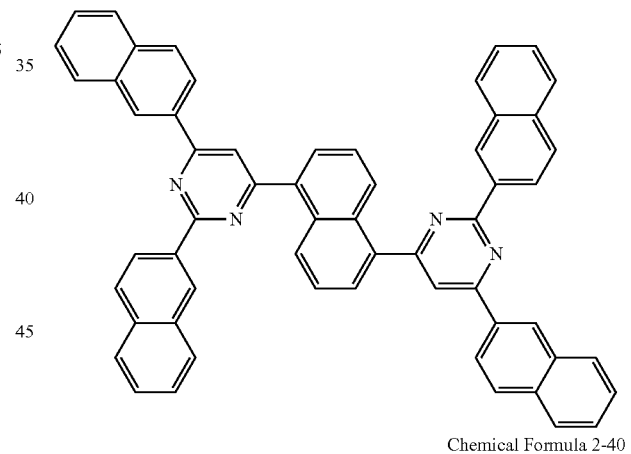
Chemical Formula 2-40
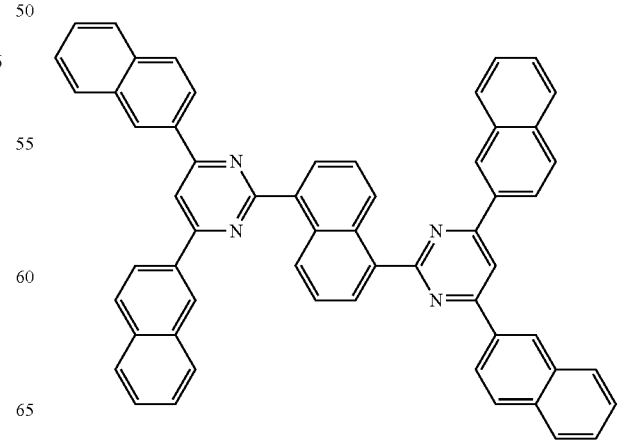

Chemical Formula 2-41
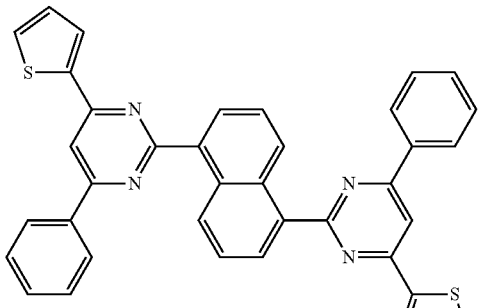
Chemical Formula 2-42
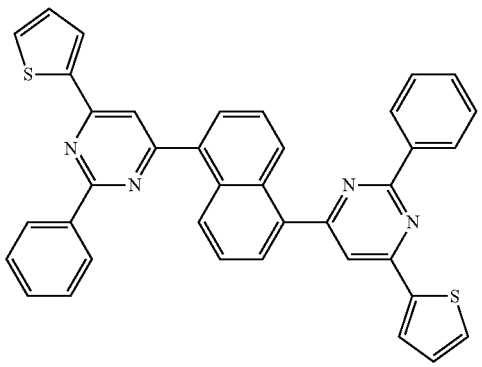
Chemical Formula 2-43
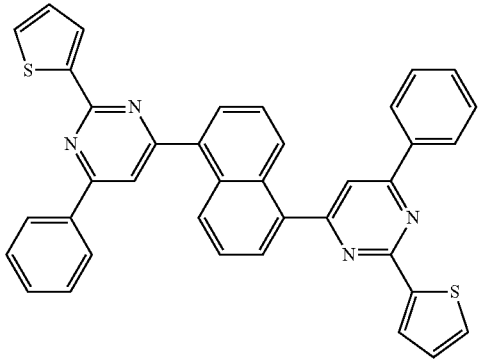
Chemical Formula 2-44
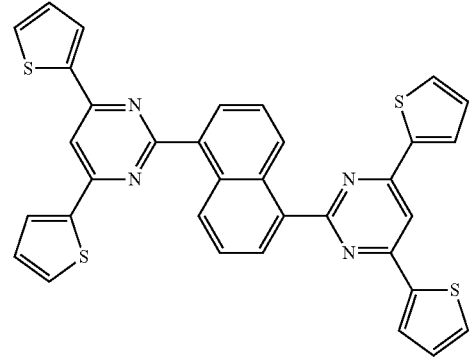
Chemical Formula 2-45
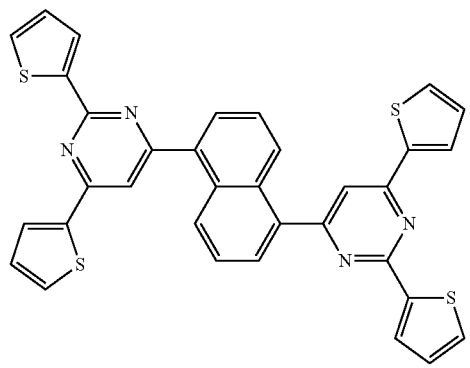
Chemical Formula 2-46
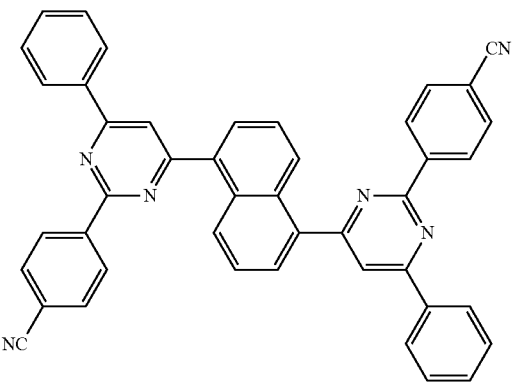
Chemical Formula 2-47
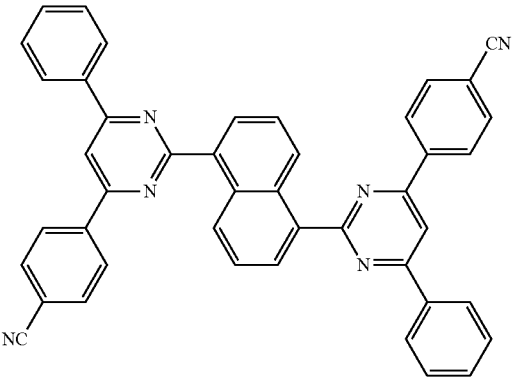
Chemical Formula 2-48
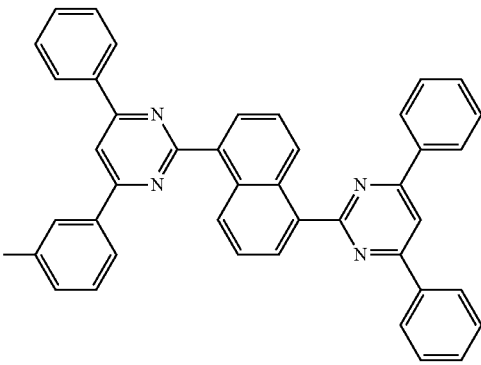

-continued

Chemical Formula 2-49

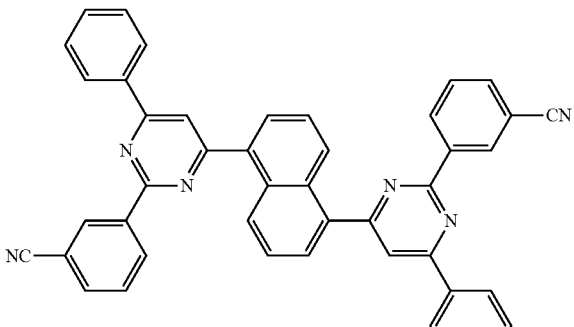

Chemical Formula 2-50

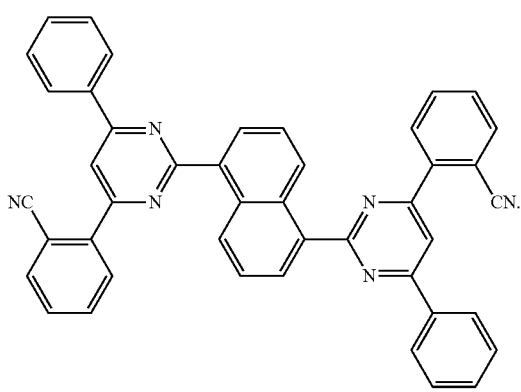

4. An organic light emitting device comprising:
a first electrode;
a second electrode provided to face the first electrode; and
one or more organic material layers including a light emitting layer provided between the first electrode and the second electrode,
wherein one or more layers of the organic material layers include the hetero-cyclic compound according to claim 1.

5. The organic light emitting device of claim 4, wherein the organic material layer includes a hole injection layer or a hole transport layer, and the hole injection layer or the hole transport layer includes the hetero-cyclic compound.

6. The organic light emitting device of claim 4, wherein the light emitting layer includes the hetero-cyclic compound as a host of the light emitting layer.

7. The organic light emitting device of claim 4, wherein the organic material layer includes an electron transport layer or an electron injection layer, and the electron transport layer or the electron injection layer includes the hetero-cyclic compound.

8. The organic light emitting device of claim 4, wherein the organic material layer including the hetero-cyclic compound includes the hetero-cyclic compound as a host, and includes another organic compound, a metal, or a metal compound as a dopant.

9. The organic light emitting device of claim 4, further comprising:
one layer or two or more layers selected from the group consisting of a hole injection layer, a hole transport layer, an electron transport layer, an electron injection layer, an electron blocking layer, and a hole blocking layer.

10. An organic light emitting device comprising:
a first electrode;
a second electrode provided to face the first electrode;
a light emitting layer provided between the first electrode and the second electrode; and
two or more organic material layers provided between the light emitting layer and the first electrode or between the light emitting layer and the second electrode,
wherein at least one of the two or more organic material layers includes the hetero-cyclic compound according to claim 1, and the two or more organic material layers include two or more selected from the group consisting of an electron transport layer, an electron injection layer, a layer simultaneously transporting and injecting electrons, and a hole blocking layer.

11. An organic light emitting device comprising:
a first electrode;
a second electrode provided to face the first electrode; and
one or more organic material layers including a light emitting layer provided between the first electrode and the second electrode,
wherein one or more layers of the organic material layers include the hetero-cyclic compound according to claim 2.

12. An organic light emitting device comprising:
a first electrode;
a second electrode provided to face the first electrode; and
one or more organic material layers including a light emitting layer provided between the first electrode and the second electrode,
wherein one or more layers of the organic material layers include the hetero-cyclic compound according to claim 3.

13. An organic light emitting device comprising:
a first electrode;
a second electrode provided to face the first electrode;
a light emitting layer provided between the first electrode and the second electrode; and
two or more organic material layers provided between the light emitting layer and the first electrode or between the light emitting layer and the second electrode,
wherein at least one of the two or more organic material layers includes the hetero-cyclic compound according to claim 2, and the two or more organic material layers include two or more selected from the group consisting of an electron transport layer, an electron injection layer, a layer simultaneously transporting and injecting electrons, and a hole blocking layer.

14. An organic light emitting device comprising:
a first electrode;
a second electrode provided to face the first electrode;
a light emitting layer provided between the first electrode and the second electrode; and
two or more organic material layers provided between the light emitting layer and the first electrode or between the light emitting layer and the second electrode,
wherein at least one of the two or more organic material layers includes the hetero-cyclic compound according to claim 3, and the two or more organic material layers include two or more selected from the group consisting of an electron transport layer, an electron injection layer, a layer simultaneously transporting and injecting electrons, and a hole blocking layer.

* * * * *